(12) United States Patent
Scharenberg

(10) Patent No.: US 7,063,959 B1
(45) Date of Patent: Jun. 20, 2006

(54) COMPOSITIONS OF THE SOC/CRAC CALCIUM CHANNEL PROTEIN FAMILY

(75) Inventor: Andrew Scharenberg, Seattle, WA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 09/869,486

(22) PCT Filed: Dec. 20, 1999

(86) PCT No.: PCT/US99/29996

§ 371 (c)(1),
(2), (4) Date: Jan. 4, 2002

(87) PCT Pub. No.: WO00/40614

PCT Pub. Date: Jul. 13, 2000

Related U.S. Application Data

(60) Provisional application No. 60/140,415, filed on Jun. 22, 1999, provisional application No. 60/120,018, filed on Jan. 29, 1999, provisional application No. 60/114,220, filed on Dec. 30, 1998.

(51) Int. Cl.
*C12P 21/06* (2006.01)
*A61K 38/17* (2006.01)
*C07K 1/00* (2006.01)
*C07H 21/04* (2006.01)
*C07H 21/02* (2006.01)

(52) U.S. Cl. .................. 435/69.1; 530/350; 536/23.1; 536/23.5; 514/12; 514/2

(58) Field of Classification Search ............... 536/23.1, 536/23.5; 530/350; 435/69.1, 320.1; 514/2, 514/44
See application file for complete search history.

(56) References Cited

U.S. PATENT DOCUMENTS

| | | | |
|---|---|---|---|
| 5,399,346 | A | 3/1995 | Anderson et al. |
| 5,580,723 | A | 12/1996 | Wells |
| 5,670,488 | A | 9/1997 | Gregory et al. |
| 5,672,344 | A | 9/1997 | Kelley et al. |
| 6,194,152 | B1 | 2/2001 | Laus et al. |

FOREIGN PATENT DOCUMENTS

| | | |
|---|---|---|
| WO | WO 95/00654 | 1/1995 |
| WO | WO 98/15657 | 4/1998 |
| WO | WO 98/37093 | 8/1998 |
| WO | WO 99/09166 | 2/1999 |
| WO | WO 99/09199 | 2/1999 |

OTHER PUBLICATIONS

Welsh, 1999, Current Opinion in Mol. Therapeutics, 1 (4), pp. 464-470.*
Roth et al., 1999, Ann. Rev. Biomed. Eng., 01, pp. 265-297.*
Caterina, M.J. et al., The capsaicin receptor: a heat-activated ion channel in the pain pathway [see comments], Nature 389: 816-24, 1997.
Garcia, R.L. et al., Differential expression of mammalian TRP homologues across tissues and cell lines, Biochemical and Biophysical Research Communications, 239(1): 279-283, 1997.
GenBank Accession No. AA261842 zs17h10.r1 NCI_CGAP_GCB1 Homo sapiens cDNA clone IMAGE:685507 5', mRNA sequence, Jan. 31, 1997.
GenBank Accession No. AA313170 EST18457 Liver, subtracted (abundant clones) I Homo sapiens cDNA 5' end, mRNA sequence, Apr. 19, 1997.
GenBank Accession No. AA370110 EST81669 Prostate gland I Homo sapiens cDNA 5' end, mRNA sequence, Apr. 21, 1997.
GenBank Accession No. AA419407 zu99b09.s1 NCI_CGAP_GCB1 Homo sapiens cDNA clone IMAGE:746105 3', mRNA sequence, May 12, 1997.
GenBank Accession No. AA419592 zu99b09.r1 NCI_CGAP_GCB1 Homo sapiens cDNA clone IMAGE:746105 5', mRNA sequence, May 12, 1997.
GenBank Accession No. AA493512 ng75e04.s1 NCI_CGAP_Pr6 Homo sapiens cDNA clone IMAGE:940638, mRNA sequence, Mar. 10, 1997.
GenBank Accession No. AA523749 ni64ell.s1 NCI_CGAP_Pr12 Homo sapiens cDNA clone IMAGE:981644 mRNA sequence, Jul. 19, 1997.
GenBank Accession No. AA551759 nf99c01.s1 NCI_CGAP_Co3 Homo sapiens cDNA clone IMAGE:928032 3', mRNA sequence, Aug. 11, 1997.
GenBank Accession No. AA592910 nn01f07.s1 NCI_CGAP_Co9 Homo sapiens cDNA clone IMAGE:1076485 3', mRNA sequence, Sep. 12, 1997.
GenBank Accession No. AA654650 nt76b07.s1 NCI_CGAP_Pr3 Homo sapiens cDNA clone IMAGE:1204405, mRNA sequence, Nov. 4, 1997.
GenBank Accession No. AA708532 zl63d12.s1 Soares_pregnant_uterus_NbHPU Homo sapiens cDNA clone IMAGE:506615 3', mRNA sequence, Dec. 24, 1997.
GenBank Accession No. AA809355 ob70f05. s1 NCI_CGAP_GCB1 Homo sapiens cDNA clone IMAGE:1336737 3', mRNA Sequence, Feb. 16, 1998.

(Continued)

*Primary Examiner*—Olga N. Chemyshev
(74) *Attorney, Agent, or Firm*—Wolf, Greenfield & Sacks, P.C.

(57) ABSTRACT

Nucleic acids encoding SOC/CRAC calcium channel polypeptides, including fragments and biologically functional variants thereof and encoded polypeptides are provided. The nucleic acids and polypeptides disclosed herein are useful as therapeutic and diagnostic agents. Agents that selectively bind to the foregoing polypeptides and genes also are provided.

6 Claims, 1 Drawing Sheet

OTHER PUBLICATIONS

GenBank Accession No. AA932133 om90h09.s1 NCI_CGAP_Kid3 Homo sapiens cDNA clone IMAGE:1554497 3', mRNA sequence, Apr. 13, 1998.

GenBank Accession No. AB001535 Homo sapiens mRNA, complete cds, Nov. 30, 1998.

GenBank Accession No. AC005538 Homo sapiens BAC clone RP11-332L11 from 2, complete sequence, Sep. 30, 2000.

GenBank Accession No. AF071787 Homo sapiens melastatin 1 (MLSN1) mRNA, complete cds, Nov. 26, 1998.

GenBank Accession No. AI050262 ub28d10.r1 Soares 2NbMT Mus musculus cDNA clone IMAGE:1379059 5' mRNA sequence, Jul. 10, 1998.

GenBank Accession No. AI098310 vy82g03.r1 Stratagene mouse macrophage (#937306) Mus musculus cDNA clone IMAGE:1312756 5' similar to WP:C05C12.3 CE02966 ; mRNA sequence, Aug. 20, 1998.

GenBank Accession No. AI226731 uj15a05.y1 Sugano mouse kidney mkia Mus musculus cDNA clone IMAGE:1908080 5' similar to TR:Q93971 Q93971 Hypothetical Protein T01H8.5 In Chromosome I ;, mRNA sequence, Oct. 29, 1998.

GenBank Accession No. AI670079 wc11f05.x1 NCI_CGAP_Pr28 Homo sapiens cDNA clone IMAGE:2314881 3', mRNA sequence, May 14, 1999.

GenBank Accession No. AI671853 wb34g04.x1 NCI_CGAP_GC6 Homo sapiens cDNA clone IMAGE:2307606 3', mRNA sequence, May 18, 1999.

GenBank Accession No. CAA92726 C. elegans GTL-1 protein (corresponding sequence C05C12.3) [Caenorhabditis elegans], Jan. 14, 2003.

GenBank Accession No. CAB00861 C. elegans GTL-2 protein (corresponding sequence F54D1.5) [Caenorhabditis elegans], Jan. 14, 2003.

GenBank Accession No. CAB05572 C. elegans GON-2 protein (corresponding sequence T01H8.5) [Caenorgabditis elegans] Jan. 14, 2003.

GenBank Accession No. D86107 Homo sapiens gene for HC21EXc132, exon, Jul. 4, 1997.

GenBank Accession No. H18835 ym45d10.r1 Soares infant brain 1NIB Homo sapiens cDNA clone IMAGE:51262 5', mRNA sequence, Jun. 29, 1995.

GenBank Accession No. N31660 yx69b04.r1 Soares melanocyte 2NbHM Homo sapiens cDNA clone IMAGE:266959 5', mRNA sequence, Jan. 10, 1996.

GenBank Accession No. R47363 Hf014-r Adult heart, Clontech Homo sapiens cDNA clone f014-r, mRNA sequence May 16, 1995.

GenBank Accession No. U16856 Dictyostelium discoideum myosin heavy chain kinase A (MHCK A) mRNA, complete cds, May 11, 1995.

GenBank Accession No. U93850 Homo sapiens elongation factor-2 kinase mRNA, complete cds, May 25, 1997.

GenBank Accession No. Z68333 Caenorhabditis elegans cosmid C05C12, complete sequence, Dec. 10, 1999.

GenBank Accession No. Z77132 Caenorhabditis elegans cosmid F54D1, complete sequence, Dec. 15, 1999.

GenBank Accession No. Z83117 Caenorbabditis elegans cosmid M04C7, complete sequence, Dec. 14, 1999.

Grynkiewicz, G. et al., A new generation of Ca2+ indicators with greatly improved fluorescence properties, J. Biol Chem 260: 3440-50, 1985.

Hoth, M. et al., Depletion of intracellular calcium stores activates a calcium current in mast cells, Nature, 355: 353-355, 1992.

Hunter, J.J. et al., Chromosomal Localization and Genomic Characterization of the Mouse Melastatin Gene (Mlsn1), Genomics 54: 116-123, 1998.

Kiselyov, K. et al., Functional interaction between InsP3 receptors and store-operated Htrp3 channels, Nature 396: 478-82, 1998.

Mathes, C., et al., Calcium release activated calcium current ($I_{CRAC}$) is a direct target for sphingosine, J Biol Chem 273(39):25020-25030, 1998.

Nagamine, K. et al., Molecular Cloning of a Novel Putative Ca2+ Channel Protein (TPRC7) Highly Expressed in Brian, Genomics 54: 124-131, 1998.

Neher, E., Ion channels for communication between and within cells, Science, 256: 498-502, 1992.

Obukhov, A.G. et al., Direct activation of trp1 cation channels by G-alpha-11 subunits, EMBO Journal, 15(21): 5833-5838, 1996.

Poenie, M. et al., Fura-2:a powerful new tool for measuring and imaging [Ca2+]i in single cells, Prog Clin Biol Res 210: 53-56, 1986.

Preuss, K.-D. et al., Expression and characterization of a trp1 homolog from rat, Biochemical and Biophysical Research Communications, 240(1): 167-172, 1997.

Putney, J.W. Jr., Type 3 inositol 1,4,5-trisphosphate receptor and capacitative calcium entry, Cell Calcium 21(3): 257-261, 1997.

Ryazanov A.G. et al., Identification of a new class of protein kinases represented by eukaryotic elongation factor-2 kinase, Proc Natl Acad Sci USA, 94(10): 4884-4889 1997.

Sainio, K. et al., Antisense inhibition of low-affinity nerve growth factor receptor in kidney cultures: power and pitfalls Cell Mol. Neurobiol. 14(5): 439-457, 1994.

Scharenberg, A.M. et al., Reconstitution of interactions between tyrosine kinases and the high affinity IgE receptor which are controlled by receptor clustering, EMBO J, 14(14):3385-3394, 1995.

Scharenberg, A.M. et al., MLSN-1/SOC-1 defines a widely expressed Ca2+/cation channel family involved in Ca2+ homeostasis and store-operated Ca2+ signaling, J. Gen. Phys 114(1):14a, 1999.

Sinkins, W.G. et al., Functional expression of TrpC1: A human homologue of the *Drosophila Trp* channel. Biochemical Journal, 331(1): 331-339, 1998.

Wes, P.D. et al., TRPC1, a human homolog of a *Drosophila* store-operated channel. Proc. Natl. Acad. Sci. USA, 92(21): 9652-9656, 1995.

Wulfing, C. et al., Visualizing the dynamics of T cell activation; Intracellular adhesion molecule 1 migrates rapidly to the T cell/B cell interface and acts to sustain calcium levels. Proc. Natl. Acad. Sci. USA, 95: 6302-6307, 1998.

Zhu, X. et al., Molecular cloning of a widely expressed human homologue for the *Drosophila* trp gene, FEBS LETTERS, 373(3): 193-198, 1995.

Zhu, X. et al., Trp, A novel mammalian gene family essential for agonist-activated capacitative Ca2+ entry, Cell, 85(5): 661-671, 1996.

* cited by examiner

US 7,063,959 B1

COMPOSITIONS OF THE SOC/CRAC CALCIUM CHANNEL PROTEIN FAMILY

RELATED APPLICATIONS

This application claims the benefit under 35 U.S.C. §120 or 35 U.S.C. §365(c) of PCT International application PCT/US99/29996 designating the United States of America, and filed Dec. 20, 1999, of which this application is a national stage filing under 35 U.S.C. §371, was published under PCT Article 21(2) in English.

Application number PCT/US99/29996 claims the benefit under 35 U.S.C. § 119(e) of U.S. provisional application 60/114,220, filed Dec. 30, 1998; 60/120,018, filed Jan. 29, 1999; and 60/140,415, filed Jun. 22, 1999.

FIELD OF THE INVENTION

This invention relates to nucleic acids coding for a novel family of calcium channel polypeptides, the encoded polypeptides, unique fragments of the foregoing, and methods of making and using same.

BACKGROUND OF THE INVENTION

Calcium channels are membrane-spanning, multi-subunit proteins that facilitate the controlled transport ("flux") of $Ca^{2+}$ ions into and out of cells. Cells throughout the animal kingdom, and at least some bacterial, fungal and plant cells, possess one or more types of calcium channels. In general, "excitable" cells, such as neurons of the central nervous system, peripheral nerve cells, and muscle cells, including those of skeletal muscles, cardiac muscles, and venous and arterial smooth muscles, possess voltage-dependent calcium channels. In a voltage-dependent calcium channel, the transport of $Ca^{2+}$ ions into and out of the cells requires a certain minimal level of depolarization (the difference in potential between the inside of the cell bearing the channel and the extracellular environment) with the rate of $Ca^{2+}$ cell flux dependent on the difference in potential. In "non-excitable" cells, calcium influx is thought to occur predominantly in response to stimuli which cause the release of calcium from intracellular stores. This process, termed store operated calcium influx, is not well understood.

Characterization of a particular type of calcium channel by analysis of whole cells is complicated by the presence of mixed populations of different types of calcium channels in the majority of cells. Although single-channel recording methods can be used to examine individual calcium channels, such analysis does not reveal information related to the molecular structure or biochemical composition of the channel. Furthermore, in this type of analysis, the channel is isolated from other cellular constituents that might be important for the channel's natural functions and pharmacological interactions. To study the calcium channel structure-function relationship, large amounts of pure channel protein are needed. However, acquiring large amounts of pure protein is difficult in view of the complex nature of these multisubunit proteins, the varying concentrations of calcium channel proteins in tissue sources, the presence of mixed populations of calcium channel proteins in tissues, and the modifications of the native protein that can occur during the isolation procedure.

SUMMARY OF THE INVENTION

The invention is based on the identification of a novel family of calcium channel polypeptides and the molecular cloning and partial characterization of a novel member of this family that is expressed predominantly in human hematopoietic cells, liver, and kidney. This newly identified family of calcium channel polypeptides is designated, "SOC" or "CRAC" or "ICRAC", for Store Operated Channels or Calcium Release Activated Channels. Although not wishing to be bound to any particular theory or mechanism, it is believed that the SOC/CRAC calcium channel polypeptides are transmembrane polypeptides that modulate $Ca^{2+}$ flux "into" and "out of" a cell, for example, in certain instances they may be activated upon depletion of $Ca^{2+}$ from intracellular calcium stores, allowing $Ca^{2+}$ influx into the cell. Accordingly, the compositions disclosed herein are believed to be useful for modulating calcium transport into and out of such intracellular stores and for the treatment of disorders that are characterized by aberrant calcium transport into and out of such intracellular stores. In particular, we believe that the SOC/CRAC calcium channel polypeptides disclosed herein play an important role in the influx of extracellular calcium by mediating the refilling of intracellular calcium stores following their depletion. Accordingly, we believe that the compositions for expressing functional SOC/CRAC calcium channel polypeptides in cells, as disclosed herein, are useful for treating patients having conditions that are characterized by reduced extracellular calcium influx into their SOC/CRAC-expressing cells. Additionally, the compositions of the invention are useful for delivering therapeutic and/or imaging agents to cells which preferentially express SOC/CRAC calcium channel polypeptides and, in particular, for delivering such agents to hematopoietic cells, liver, heart, spleen, and kidney to modulate proliferation and growth of these cells. Moreover, in view of the importance of cellular calcium levels to cell viability, we believe that SOC-2/CRAC-1, SOC-3/CRAC-2, and SOC-4/CRAC-3 as disclosed herein, and/or other members of the SOC/CRAC family of calcium channel polypeptides, represent an ideal target for designing and/or identifying (e.g., from molecular libraries) small molecule inhibitors that block lymphocyte proliferation, as well as other binding agents that selectively bind to SOC/CRAC polypeptides to which drugs or toxins can be conjugated for delivery to SOC/CRAC polypeptide expressing cells.

The invention is based, in part, on the molecular cloning and sequence analysis of the novel SOC/CRAC calcium channel molecules disclosed herein (also referred to as a "SOC-2/CRAC-1 molecule," a "SOC-3/CRAC-2 molecule," and/or "SOC-4/CRAC-3 molecule") that are predominantly expressed in human hematopoietic cells, liver, spleen, heart, and kidney (SOC-2/CRAC-1), kidney and colon (SOC-3/CRAC-2), and prostate (SOC-4/CRAC-3 molecule). As used herein, a "SOC/CRAC molecule" embraces a "SOC/CRAC calcium channel nucleic acid" (or "SOC/CRAC nucleic acid") and a "SOC/CRAC calcium channel polypeptide" (or "SOC/CRAC polypeptide"). Homologs and alleles also are embraced within the meaning of a SOC/CRAC calcium channel molecule.

According to one aspect of the invention, isolated SOC/CRAC nucleic acids which code for one or more member(s) of the SOC/CRAC family of calcium channel polypeptides or unique fragments thereof are provided. The isolated nucleic acids refer to one or more of the following:

(a) nucleic acid molecules which hybridize under stringent conditions to a nucleic acid molecule selected from the group consisting of SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31, and which code for a SOC/CRAC polypeptide;

(b) deletions, additions and substitutions of (a) which code for a respective SOC/CRAC polypeptide;

(c) nucleic acid molecules that differ from the nucleic acid molecules of (a) or (b) in codon sequence due to the degeneracy of the genetic code, and (d) complements of (a), (b) or (c).

The invention in another aspect provides an isolated nucleic acid molecule selected from the group consisting of (a) a unique fragment of a nucleic acid molecule selected from the group consisting of SEQ ID NO:1, SEQ ID NO:3, SEQ ID NO:5, SEQ ID NO:7, SEQ ID NO:23, SEQ ID NO:25, SEQ ID NO:29, and SEQ ID NO:31, (b) complements of (a), provided that the unique fragment includes a sequence of contiguous nucleotides which is not identical to any sequence selected from a sequence group consisting of (1) sequences having the SEQ ID NOs or GenBank accession numbers of Table I, (2) complements of (1), and (3) fragments of (1) and (2).

According to yet another aspect of the invention, isolated SOC/CRAC polypeptides are provided. The isolated SOC/CRAC polypeptide molecules are encoded by one or more SOC/CRAC nucleic acid molecules of the invention. Preferably, the SOC/CRAC polypeptide contains one or more polypeptides selected from the group consisting of the polypeptides having SEQ ID NOs 2, 4, 6, 8, 24, 26, 28, 30, and 32. In other embodiments, the isolated polypeptide may be a fragment or variant of the foregoing SOC/CRAC polypeptide molecules of sufficient length to represent a sequence unique within the human genome, and identifying with a polypeptide that functions as a calcium channel, provided that the fragment excludes a sequence of contiguous amino acids identified in Table II, and/or excludes a sequence of contiguous amino acids encoded for by a nucleic acid sequence identified in Table I. In another embodiment, immunogenic fragments of the polypeptide molecules described above are provided.

According to another aspect of the invention, isolated SOC/CRAC binding agents (e.g., polypeptides) are provided which selectively bind to a SOC/CRAC molecule (e.g., a SOC/CRAC polypeptide encoded by the isolated nucleic acid molecules of the invention). Preferably, the isolated binding agents selectively bind to a polypeptide which comprises the sequence selected from the group consisting of SEQ ID NO:2, SEQ ID NO:4, SEQ ID NO:6, SEQ ID NO:8, SEQ ID NO:24, SEQ ID NO:26, SEQ ID NO:28, SEQ ID NO:30, and SEQ ID NO:32, or unique fragments thereof. In the preferred embodiments, the isolated binding polypeptides include antibodies and fragments of antibodies (e.g., Fab, F(ab)$_2$, Fd and antibody fragments which include a CDR3 region which binds selectively to a SOC/CRAC polypeptide). Preferably, the antibodies for human therapeutic applications are human antibodies.

According to another aspect of the invention, a pharmaceutical composition containing a pharmaceutically effective amount of an isolated SOC/CRAC nucleic acid, an isolated SOC/CRAC polypeptide, or an isolated SOC/CRAC binding polypeptide in a pharmaceutically acceptable carrier also is provided. The pharmaceutical compositions are useful in accordance with therapeutic methods disclosed herein.

According to yet another aspect of the invention, a method for isolating a SOC/CRAC molecule is provided. The method involves:

a) contacting a SOC/CRAC nucleic acid or a SOC/CRAC binding polypeptide with a sample that is believed to contain one or more SOC/CRAC molecules, under conditions to form a complex of the SOC/CRAC nucleic acid or the SOC/CRAC binding polypeptide and the SOC/CRAC molecule;

b) detecting the presence of the complex;

c) isolating the SOC/CRAC molecule from the complex; and d) determining whether the isolated SOC/CRAC molecule has SOC/CRAC calcium channel activity. As used herein "SOC/CRAC calcium channel activity" refers to the transport of $Ca^{2+}$ into and out of intracellular stores that is mediated by a SOC/CRAC polypeptide. In general, the SOC/CRAC calcium channel activity is initiated by a reduction or depletion of intracellular calcium stores.

In certain embodiments, the SOC/CRAC nucleic acid is a SOC-2/CRAC-1 nucleic acid (e.g., a nucleic acid having SEQ ID NO:27, or complements thereof); in certain other embodiments, the SOC/CRAC nucleic acid is a SOC-3/CRAC-2 nucleic acid (e.g., a nucleic acid having SEQ ID NO:29, or complements thereof); in further embodiments, the SOC/CRAC nucleic acid is a SOC-4/CRAC-3 nucleic acid (e.g., a nucleic acid having SEQ ID NO:31, or complements thereof). In yet other embodiments, the SOC/CRAC polypeptide is a SOC-2/CRAC-1 binding polypeptide (e.g., an antibody that selectively binds to a SOC-2/CRAC-1 polypeptide). In yet further embodiments, the SOC/CRAC polypeptide is a SOC-3/CRAC-2 binding polypeptide (e.g., an antibody that selectively binds to a SOC-3/CRAC-2 polypeptide). In some embodiments, the SOC/CRAC polypeptide is a SOC-4/CRAC-3 binding polypeptide (e.g., an antibody that selectively binds to a SOC-4/CRAC-3 polypeptide). In the preferred embodiments, the isolated binding polypeptides include antibodies and fragments of antibodies (e.g., Fab, F(ab)$_2$, Fd and antibody fragments which include a CDR3 region which binds selectively to a SOC-2/CRAC-1, to a SOC-3/CRAC-2, and/or to a SOC-4/CRAC-3 polypeptide). Preferably the isolated binding polypeptides or other binding agents selectively bind to a single SOC/CRAC molecule, i.e., are capable of distinguishing between different members of the SOC/CRAC family. Accordingly, one or more SOC/CRAC binding agents can be contained in a single composition (e.g., a pharmaceutical composition) to identify multiple SOC/CRAC molecules in vivo or in vitro.

According to yet another aspect of the invention, a method for identifying agents useful in the modulation of SOC/CRAC calcium channel activity is provided. The method involves:

a) contacting a SOC/CRAC polypeptide with a candidate agent suspected of modulating SOC/CRAC calcium channel activity, under conditions sufficient to allow the candidate agent to interact selectively with (e.g. bind to) the SOC/CRAC polypeptide;

b) detecting a $Ca^{2+}$ concentration of step (b) associated with the SOC/CRAC calcium channel activity of the SOC/CRAC polypeptide in the presence of the candidate agent; and c) comparing the $Ca^{2+}$ concentration of step (b) with a control $Ca^{2+}$ concentration of a SOC/CRAC polypeptide in the absence of the candidate agent to determine whether the candidate agent modulates (increases or decreases) SOC/CRAC calcium channel activity.

According to another aspect of the invention, a method for identifying agents useful in the modulation of a SOC/CRAC polypeptide kinase activity is provided. The method involves:

a) contacting a SOC/CRAC polypeptide with kinase activity with a candidate agent suspected of modulating SOC/CRAC kinase activity, under conditions sufficient to allow the candidate agent to interact with the SOC/CRAC polypeptide and modulate its kinase activity;

b) detecting a kinase activity associated with the SOC/CRAC polypeptide in the presence of the candidate agent; and c) comparing the kinase activity of step (b) with a control kinase activity of a SOC/CRAC polypeptide in the absence of the candidate agent to determine whether the candidate agent modulates (increases or decreases) SOC/CRAC kinase activity. In some embodiments the SOC/CRAC polypeptide comprises amino acids 999–1180 of the SOC-2/CRAC-1 polypeptide (SEQ ID NO:24), or a fragment thereof that retains the kinase activity.

According to yet another aspect of the invention, a method for determining the level of expression of a SOC/CRAC polypeptide in a subject is provided. The method involves:

a) measuring the expression of a SOC/CRAC polypeptide in a test sample, and b) comparing the measured expression of the SOC/CRAC polypeptide in the test sample to the expression of a SOC/CRAC polypeptide in a control containing a known level of expression to determine the level of SOC/CRAC expression in the subject. Expression is defined as SOC/CRAC mRNA expression or SOC/CRAC polypeptide expression. Various methods can be used to measure expression. The preferred embodiments of the invention utilize PCR and Northern blotting for measuring mRNA expression, and monoclonal or polyclonal SOC/CRAC antisera as reagents for measuring SOC/CRAC polypeptide expression. In preferred embodiments, the SOC/CRAC molecule (nucleic acid and/or polypeptide) is SOC-2/CRAC-1. In other preferred embodiments, the SOC/CRAC molecule is SOC-3/CRAC-2. In yet further preferred embodiments, the SOC/CRAC molecule is SOC-4/CRAC-3. In certain embodiments, the test samples include biopsy samples and biological fluids such as blood. The method is useful, e.g., for assessing the presence or absence or stage of a proliferative disorder in a subject.

The invention also contemplates kits comprising a package including assays for SOC/CRAC epitopes, SOC/CRAC nucleic acids, and instructions, and optionally related materials such as controls, for example, a number, color chart, or an epitope of the expression product of the foregoing isolated nucleic acid molecules of the invention for comparing, for example, the level of SOC/CRAC polypeptides or SOC/CRAC nucleic acid forms (wild-type or mutant) in a test sample to the level in a control sample having a known amount of a SOC/CRAC nucleic acid or SOC/CRAC polypeptide. This comparison can be used to assess in a subject a risk of developing a cancer or the progression of a cancer. The kits may also include assays for other known genes, and expression products thereof, associated with, for example, proliferative disorders (e.g., BRCA, p53, etc.). In a preferred embodiment, the kit comprises a package containing: (a) a binding agent that selectively binds to an isolated nucleic acid of the invention or an expression product thereof to obtain a measured test value, (b) a control containing a known amount of a SOC/CRAC nucleic acid or a SOC/CRAC polypeptide to obtain a measured control value, and (c) instructions for comparing the measured test value to the measured control value to determine the amount of SOC/CRAC nucleic acid or expression product thereof in a sample.

The invention provides isolated nucleic acid molecules, unique fragments thereof, expression vectors containing the foregoing, and host cells containing the foregoing. The invention also provides isolated binding polypeptides and binding agents which bind such polypeptides, including antibodies, and pharmaceutical compositions containing any of the compositions of the invention. The foregoing can be used, inter alia, in the diagnosis or treatment of conditions characterized by the aberrant expression levels and/or the presence of mutant forms of a SOC/CRAC nucleic acid or polypeptide. The invention also provides methods for identifying agents that alter the function of the SOC/CRAC polypeptide.

These and other aspects of the invention, as well as various advantages and utilities, will be more apparent with reference to the detailed description of the preferred embodiments.

BRIEF DESCRIPTION OF THE SEQUENCES

SEQ ID NO:1 is a partial nucleotide sequence of the human SOC-2/CRAC-1 cDNA.

SEQ ID NO:2 is the predicted amino acid sequence of the translation product of human SOC-2/CRAC-1 cDNA (SEQ ID NO:1).

SEQ ID NO:3 is a partial nucleotide sequence of the human SOC-2/CRAC-1 cDNA.

SEQ ID NO:4 is the predicted amino acid sequence of the translation product of human SOC-2/CRAC-1 cDNA (SEQ ID NO:3).

SEQ ID NO:5 is a partial nucleotide sequence of the human SOC-2/CRAC-1 cDNA.

SEQ ID NO:6 is the predicted amino acid sequence of the translation product of human SOC-2/CRAC-1 cDNA (SEQ ID NO:5).

SEQ ID NO:7 is a partial nucleotide sequence of the mouse homologue (mSOC-2/CRAC-1) of the human SOC-2/CRAC-1 cDNA.

SEQ ID NO:8 is the predicted amino acid sequence of the translation product of the mSOC-2/CRAC-1 cDNA (SEQ ID NO:7).

SEQ ID NO:9 is the nucleotide sequence of the mouse MLSN-1 (SOC-1) cDNA.

SEQ ID NO:10 is the predicted amino acid sequence of the translation product of the mouse MLSN-1 (SOC-1) cDNA (SEQ ID NO:9).

SEQ ID NO:11 is the nucleotide sequence of a human calcium channel cDNA with GenBank Acc. no.: AB001535.

SEQ ID NO:12 is the predicted amino acid sequence of the translation product of the human calcium channel cDNA with GenBank Acc. no.: AB001535 (SEQ ID NO:11).

SEQ ID NO:13 is the amino acid sequence of a *C. Elegans* polypeptide at the c05c12.3 locus.

SEQ ID NO:14 is the amino acid sequence of a *C. Elegans* polypeptide at the F54D1 locus.

SEQ ID NO:15 is the amino acid sequence of a *C. Elegans* polypeptide at the t01H8 locus.

SEQ ID NO:16 is the nucleotide sequence of a mouse kidney cDNA with GenBank Acc. no.: AI226731.

SEQ ID NO:17 is the predicted amino acid sequence of the translation product of the mouse kidney cDNA with GenBank Acc. no.: AI226731 (SEQ ID NO:16).

SEQ ID NO:18 is the nucleotide sequence of a human brain cDNA with GenBank Acc. no.: H18835.

SEQ ID NO:19 is the predicted amino acid sequence of the translation product of the human brain cDNA with GenBank Acc. no.: H18835 (SEQ ID NO:18).

SEQ ID NO:20 is the nucleotide sequence of the human EST with GenBank Acc. no.: AA419592.

SEQ ID NO:21 is the nucleotide sequence of the human EST with GenBank Acc. no.: AA419407.

SEQ ID NO:22 is the nucleotide sequence of the mouse EST with GenBank Acc. no.: AI098310.

SEQ ID NO:23 is a partial nucleotide sequence of the human SOC-2/CRAC-1 cDNA that contains the SOC-2/CRAC-1 sequences of SEQ ID NO:1, SEQ ID NO:3, and SEQ ID NO:5.

SEQ ID NO:24 is the predicted amino acid sequence of the translation product of human SOC-2/CRAC-1 cDNA (SEQ ID NO:23).

SEQ ID NO:25 is a partial nucleotide sequence of the human SOC-3/CRAC-2 cDNA.

SEQ ID NO:26 is the predicted amino acid sequence of the translation product of human SOC-3/CRAC-2 cDNA (SEQ ID NO:25).

SEQ ID NO:27 is the full nucleotide sequence of the human SOC-2/CRAC-1 cDNA.

SEQ ID NO:28 is the predicted amino acid sequence of the translation product of human SOC-2/CRAC-1 cDNA (SEQ ID NO:27).

SEQ ID NO:29 is the full nucleotide sequence of the human SOC-3/CRAC-2 cDNA.

SEQ ID NO:30 is the predicted amino acid sequence of the translation product of human SOC-3/CRAC-2 cDNA (SEQ ID NO:29).

SEQ ID NO:31 is the full nucleotide sequence of the human SOC-4/CRAC-3 cDNA.

SEQ ID NO:32 is the predicted amino acid sequence of the translation product of human SOC-4/CRAC-3 cDNA (SEQ ID NO:31).

DETAILED DESCRIPTION OF THE INVENTION

Figure 1:
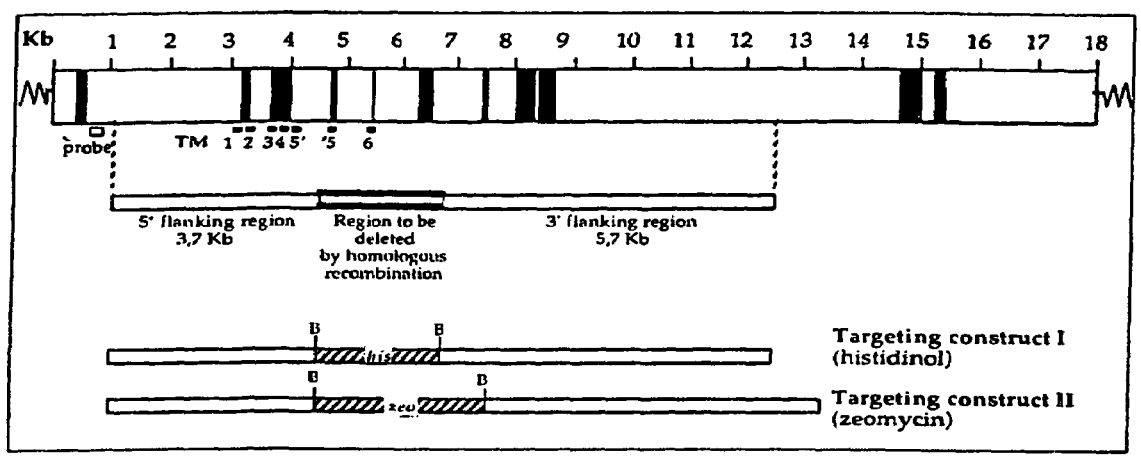
FIG. 1 is a schematic depicting the intron/exon organization of the chicken SOC-2/CRAC-1 genomic sequence, as well as the putative transmembrane (TM) domains, and the targeting constructs utilized in the knockout experiments.

One aspect of the invention involves the partial cloning of cDNAs encoding members of a novel family of calcium channel polypeptides, referred to herein as "SOC/CRAC" (designated "SOC" or "CRAC" or "ICRAC", for Store Operated Channels or Calcium Release Activated Channels, or CECH). Although not intending to be bound to any particular mechanism or theory, we believe that a SOC/CRAC family member is a transmembrane calcium channel that modulates $Ca^{2+}$ flux "into" and "out of" a cell; in certain instances it may be activated upon depletion of $Ca^{2+}$ from intracellular calcium stores, allowing $Ca^{2+}$ influx into the cell.

The first three isolated SOC/CRAC members disclosed herein, define a new family of calcium channels which is distinct from previously described calcium channels, such as voltage gated calcium channels, ryanodine receptor/inositol-1,4,5-triphosphate receptor channels, and Transient Receptor Potential (TRP) channels. The SOC/CRAC family of calcium channels exhibits high selectivity (with a $P_{Ca}/P_{Na}$ ratio near 1000), a unitary conductance below the detection level of the patch clamp method (the conductance estimated at approximately 0.2 picosiemens), and are subject to inhibition by high intracellular calcium levels. Although not intending to be bound to any particular mechanism or theory, we believe that SOC/CRAC calcium channels are responsible for the majority of, for example, calcium entry which occurs when intracellular calcium stores are depleted, and that SOC/CRAC currents are important for initiating various types of calcium-dependent processes. Thus, we believe that SOC/CRAC calcium channels play an important role in cellular calcium homeostasis by, e.g., modulating the supply of calcium to refill intracellular stores when depleted.

The isolated full-length sequence of a representative, first member of the SOC/CRAC family, human SOC/CRAC nucleic acid (cDNA), SOC-2/CRAC-1, is represented as the nucleic acid of SEQ ID NO:27. This nucleic acid sequence codes for the SOC-2/CRAC-1 polypeptide with the predicted amino acid sequence disclosed herein as SEQ ID NO:28. A. homologous mouse cDNA sequence (>90% identity to the human at the nucleotide level) is represented as the nucleic acid of SEQ ID NO:7, and codes for a unique fragment of a mouse SOC-2/CRAC-1 polypeptide having the predicted, partial amino acid sequence represented as SEQ ID NO:8. Analysis of the SOC-2/CRAC-1 partial sequence by comparison to nucleic acid and protein databases show that SOC-2/CRAC-1 shares a limited homology to mouse MLSN-1 (SOC-1, SEQ ID NOs: 9 and 10). Limited homology is also shared between SOC-2/CRAC-1 and three *C. Elegans* polypeptides (SEQ ID NOs:13, 14, and 15). We further believe that SOC-2/CRAC-1 plays a role in the regulation of cellular $Ca^{2+}$ fluxing and, in particular, lymphocyte $Ca^{2+}$ fluxing.

A second member of the human SOC/CRAC family of calcium channels, SOC-3/CRAC-2, is represented as the nucleic acid of SEQ ID NO:29, and codes for the human SOC-3/CRAC-2 polypeptide having the predicted amino acid sequence represented as SEQ ID NO:30 (this molecule may also be referred to as CECH2). SOC-3/CRAC-2 is predominantly expressed in human hematopoietic cells (including peripheral blood lymphocytes, liver, bone marrow, spleen, thymus, lymph nodes, heart, and kidney. Expression can also be detected (at lesser levels) in brain, skeletal muscle colon, small intestine, placenta, lung, and cells (cell lines) such as HL-60, HeLa, K562, MOLT-4, SW480, A459, and G361.

A third member of the human SOC/CRAC family of calcium channels, SOC-4/CRAC-3, is represented as the nucleic acid of SEQ ID NO:31, and codes for the human SOC-4/CRAC-3 polypeptide having the predicted amino acid sequence represented as SEQ ID NO:32 (this molecule may also be referred to as CECH6). It specifically expressed in the prostate gland/cells.

As used herein, a SOC/CRAC calcium channel nucleic acid (also referred to herein as a "SOC/CRAC nucleic acid") refers to a nucleic acid molecule which: (1) hybridizes under stringent conditions to one or more of the nucleic acids having the sequences of SEQ ID NOs 7, 27, 29, and/or 31 (sequences of the mouse and human SOC-2/CRAC-1, human SOC-3/CRAC-2, and human SOC-4/CRAC-3 nucleic acids), and (2) codes for a SOC-2/CRAC-1, a SOC-3/CRAC-2 or a SOC-4/CRAC-3 calcium channel polypeptide, respectively, or unique fragments of said SOC-2/CRAC-1, SOC-3/CRAC-2, or SOC-4/CRAC-3 polypeptide.

As used herein, a SOC/CRAC calcium channel polypeptide (also referred to herein as a "SOC/CRAC polypeptide") refers to a polypeptide that is coded for by a SOC-2/CRAC-1, a SOC-3/CRAC-2, and/or a SOC-4/CRAC-3 nucleic acid. Preferably, the above-identified SOC/CRAC polypeptides mediate transport of calcium into and out of a cell.

SOC/CRAC polypeptides also are useful as immunogenic molecules for the generation of binding polypeptides (e.g., antibodies) which bind selectively to SOC/CRAC (e.g., SOC-2/CRAC-1, SOC-3/CRAC-2, and/or SOC-4/CRAC-3) polypeptides. Such antibodies can be used in diagnostic assays to identify and/or quantify the presence of a SOC/CRAC polypeptide in a sample, such as a biological fluid or biopsy sample. SOC/CRAC polypeptides further embrace functionally equivalent fragments, variants, and analogs of the preferred SOC/CRAC polypeptides, provided that the fragments, variants, and analogs also are useful in mediating calcium transport into and out of intracellular calcium stores.

As used herein, "SOC/CRAC calcium channel activity" refers to $Ca^{2+}$ transport ("$Ca^{2+}$ fluxing") across the plasma membrane that is mediated by a SOC/CRAC calcium channel polypeptide. The SOC/CRAC calcium channel polypeptide typically has one or more of the following properties: high selectivity, a unitary conductance below the detection level of the patch clamp method, and are subject to inhibition by high intracellular calcium levels. Such activity can be easily detected using standard methodology well known in the art. See, e.g., the Examples and Neher, E., "Ion channels for communication between and within cells", *Science,* 1992; 256:498–502; and Hoth, M., and Penner, R., "Depletion of intracellular calcium stores activates a calcium current in mast cells", *Nature,* 1992; 355 (6358): 353–6.

According to one aspect of the invention, isolated nucleic acid molecules which code for one or more member(s) of the SOC/CRAC family of calcium channel polypeptides are provided. The isolated nucleic acid molecules are selected from the following groups:

(a) nucleic acid molecules which hybridize under stringent conditions to one or more nucleic acid molecules selected from the group consisting of SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31, and which code for a SOC/CRAC polypeptide;

(b) deletions, additions and substitutions of (a) which code for a respective SOC/CRAC polypeptide;

(c) nucleic acid molecules that differ from the nucleic acid molecules of (a) or (b) in codon sequence due to the degeneracy of the genetic code, and (d) complements of (a), (b) or (c).

In certain embodiments, the isolated nucleic acid molecule comprises one or more of nucleotides 1–1212 of SEQ ID NO:1; nucleotides 1–739 of SEQ ID NO:3; nucleotides 1–1579 of SEQ ID NO:5; nucleotides 1–5117 of SEQ ID NO:23; the mouse homolog for SOC-2/CRAC-1 corresponding to SEQ ID NO:7; nucleotides 1–2180 of SEQ ID NO:25; nucleotides 382–5976 of SEQ ID NO:27; nucleotides 73–3714 of SEQ ID NO:29; and nucleotides 23–3434 of SEQ ID NO:31. In yet other embodiments, the isolated nucleic acid molecule comprises a molecule which encodes a polypeptide having one or more sequences selected from the group consisting of SEQ ID NO:2, SEQ ID NO:4, SEQ ID NO:6, SEQ ID NO:8, SEQ ID NO:24, SEQ ID NO:26, SEQ ID NO:28, SEQ ID NO:30, and SEQ ID NO:32.

According to yet another aspect of the invention, an isolated nucleic acid molecule is provided which is selected from the group consisting of:

(a) a unique fragment of a nucleic acid molecule selected from the group consisting of SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31, (of sufficient length to represent a sequence unique within the human genome); and (b) complements of (a), provided that the unique fragment includes a sequence of contiguous nucleotides which is not identical to a sequence in the prior art as represented by the sequence group consisting of: (1) sequences having the SEQ ID NOs or GenBank accession numbers of Table I, (2) complements of (1), and (3) fragments of (1) and (2).

In some embodiments, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In other embodiments, the unique fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect of the invention, expression vectors and host cells containing (e.g., transformed or transfected with) expression vectors comprising the nucleic acid molecules disclosed herein operably linked to a promoter are provided. In certain preferred embodiments, the host cells are eukaryotic cells.

The isolated nucleic acid molecules disclosed herein have various utilities, including their use as probes and primers to identify additional members of the SOC/CRAC family of calcium channels, as diagnostic reagents for identifying the presence of SOC/CRAC polypeptides in biological or other samples, and as agents for generating SOC/CRAC binding polypeptides (e.g., antibodies) that can be used as reagents in diagnostic and therapeutic assays to identify the presence, absence, and/or amounts of a SOC/CRAC nucleic acid or polypeptide in a biological or other sample.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulatable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art.

As used herein with respect to polypeptides (discussed below), the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Homologs and alleles of the SOC/CRAC nucleic acids of the invention can be identified by conventional techniques. Thus, an aspect of the invention is those nucleic acid sequences which code for SOC/CRAC polypeptides and which hybridize to a nucleic acid molecules selected from a group consisting of the nucleic acid of SEQ ID NO: 1, the nucleic acid of SEQ ID NO:3, the nucleic acid of SEQ ID NO:5, the nucleic acid of SEQ ID NO:7, the nucleic acid of SEQ ID NO:23, the nucleic acid of SEQ ID NO:25, the nucleic acid of SEQ ID NO:27, the nucleic acid of SEQ ID NO:29, and the nucleic acid of SEQ ID NO:31, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of the SOC/CRAC nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1, SEQ ID NO:3, SEQ ID NO:5, SEQ ID NO:7, SEQ ID NO:23, SEQ ID NO:25, SEQ ID NO:27, SEQ ID NO:29, and/or SEQ ID NO:31, and SEQ ID NO:2, SEQ ID NO:4, SEQ ID NO:6, SEQ ID NO:8, SEQ ID NO:24, SEQ ID NO:26, SEQ ID NO:28, SEQ ID NO:30, and/or SEQ ID NO:32, respectively. In some instances sequences will share at least 50% nucleotide identity and/or at least 65% amino acid identity and in still other instances sequences will share at least 60% nucleotide identity and/or at least 75% amino acid identity. The homology can be calculated using various, publicly available software tools developed by NCBI (Bethesda, Md.) that can be obtained through the internet (ncbi.nlm.nih.gov/pub/). Exemplary tools include the BLAST system available at ncbi.nlm.nih.gov. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for SOC/CRAC related genes, such as homologs and alleles of SOC-2/CRAC-1 and/or SOC-3/CRAC-2, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the expression of the SOC/CRAC gene is prominent in certain human tissues (e.g., SOC-2/CRAC-1: lymphoid tissue/heart, SOC-3/CRAC-2: kidney/colon, SOC-4/CRAC-3: prostate), and given the teachings herein of partial human SOC/CRAC cDNA clones, full-length and other mammalian sequences corresponding to the human SOC/CRAC partial nucleic acid sequences can be isolated from, for example, a cDNA library prepared from one or more of the tissues in which SOC-2/CRAC-1 expression is prominent, SOC-3/CRAC-2 is prominent, and/or SOC-4/CRAC-3 expression is prominent, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating SOC/CRAC polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of an isolated nucleic acid molecule selected from the group consisting of SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31. A unique fragment is one that is a 'signature' for the larger nucleic acid. For example, the unique fragment is long enough to assure that its precise sequence is not found in molecules within the human genome outside of the SOC/CRAC nucleic acids defined above (and human alleles). Those of ordinary skill in the art may apply no more than routine procedures to determine if a fragment is unique within the human genome.

Unique fragments, however, exclude fragments completely composed of the nucleotide sequences of any of GenBank accession numbers and SEQ ID NOs listed in Table I (SEQ ID NO:9, AB001535, AI226731, H18835, AA419592, AA261842, AA419407, AI098310, AA592910, D86107, AF071787, Z77132, Z83117, Z68333, AA708532, AA551759, AA932133, R47363, N31660, AC005538, AA654650, AA370110, AA313170, AA493512, AI670079, AI671853, AC005538, AA654650, AA370110, AA313170, AA493512, AI670079, AI671853), or other previously published sequences as of the filing date of this application.

A fragment which is completely composed of the sequence described in the foregoing GenBank deposits and SEQ ID NO:9, is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the SOC/CRAC polypeptides, useful, for example, in the preparation of antibodies, immunoassays or therapeutic applications. Unique fragments further can be used as antisense molecules to inhibit the expression of SOC/CRAC nucleic acids and polypeptides, respectively.

As will be recognized by those skilled in the art, the size of the unique fragment will depend upon its conservancy in the genetic code. Thus, some regions of SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31, and complements thereof, will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 1212, or SEQ ID NO:3 beginning at nucleotide 1 and ending at nucleotide 739, or SEQ ID NO:5 beginning at nucleotide 1 and ending at nucleotide 1579, or SEQ ID NO:7 beginning at nucleotide 1 and ending at nucleotide 3532, or SEQ ID NO:23 beginning at nucleotide 1 and ending at nucleotide 5117, SEQ ID NO:25 beginning at nucleotide 1 and ending at nucleotide 2180, SEQ ID NO:27 beginning at nucleotide 1 and ending at nucleotide 7419, or SEQ ID NO:29 beginning at nucleotide 1 and ending at nucleotide 4061, or SEQ ID NO:31 beginning at nucleotide 1 and ending at nucleotide 4646, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a SOC/CRAC polypeptide, to decrease SOC/CRAC calcium channel activity. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, SEQ ID NO:3, SEQ ID NO:5, SEQ ID NO:7, SEQ ID NO:23, SEQ ID NO:25, SEQ ID NO:27, SEQ ID NO:29, and SEQ ID NO:31, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nat. Med. 1(11):1116–1118, 1995). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439–457, 1994) and at which proteins are not expected to bind. Finally, although, SEQ ID No:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1, SEQ ID NO:3, SEQ ID NO:5, SEQ ID NO:7, SEQ ID NO:23, SEQ ID NO:25, in SEQ ID NO:27, SEQ ID NO:29, and SEQ ID NO:31. Similarly, antisense to allelic or homologous SOC/CRAC cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding SOC/CRAC polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for SOC/CRAC proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E. coli and eukaryotic cells such as mouse, hamster, pig, goat, primate, yeast, xenopous, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

According to yet another aspect of the invention, isolated SOC/CRAC polypeptides are provided. Preferably, the isolated SOC/CRAC polypeptides are encoded by the isolated SOC/CRAC nucleic acid molecules disclosed herein. More preferably, the isolated SOC/CRAC polypeptides of the invention are encoded by the nucleic acid molecules having SEQ ID Nos. 1, 3, 5, 7, 23, 25, 27, 29, and 31. In yet other embodiments, the isolated SOC/CRAC polypeptides of the invention have an amino acid sequence selected from the group consisting of SEQ ID Nos. 2, 4, 6, 8, 24, 26, 28, 30 and 32. Preferably, the isolated SOC/CRAC polypeptides are of sufficient length to represent a sequence unique within the human genome. Thus, the preferred embodiments include a sequence of contiguous amino acids which is not identical to a prior art sequence as represented by the sequence group consisting of the contiguous amino acids identified in Table II (SEQ ID NO:10, SEQ ID NO:13, SEQ ID NO:14, SEQ ID NO:15, SEQ ID NO:17, SEQ ID NO:19 and GenBank Acc. Nos. AB001535, AA592910, D86107, AF071787, Z77132, Z83117, Z68333, AA708532, AA551759, AA932133, R47363, N31660, NP003298, CAB00861, NP002411, CAA92726, CAB05572).

In certain embodiments, the isolated SOC/CRAC polypeptides are immunogenic and can be used to generate binding polypeptides (e.g., antibodies) for use in diagnostic and therapeutic applications. Such binding polypeptides also are useful for detecting the presence, absence, and/or amounts of a SOC/CRAC nucleic acid or polypeptide in a sample such as a biological fluid or biopsy sample. Preferably, the SOC/CRAC polypeptides that are useful for generating binding polypeptides are unique polypeptides and, therefore, binding of the antibody to a SOC/CRAC polypeptide in a sample is selective for the SOC/CRAC polypeptide.

Expression vectors containing all the necessary elements for expression are commercially available and known to those skilled in the art. See, e.g., Sambrook et al., *Molecular Cloning: A Laboratory Manual*, Second Edition Cold Spring Harbor Laboratory Press, 1989. Cells are genetically engineered by the introduction into the cells of heterologous DNA (RNA) encoding a SOC/CRAC polypeptide or fragment or variant thereof. The heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, SOC/CRAC cDNA sequence containing expression vectors, to transfect host cells and cell lines, by these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The invention also permits the construction of SOC/CRAC gene "knock-outs" in cells and in animals, providing materials for studying certain aspects of SOC/CRAC calcium channel activity.

The invention also provides isolated polypeptides (including whole proteins and partial proteins), encoded by the foregoing SOC/CRAC nucleic acids, and include the polypeptides of SEQ ID NO:2, 4, 6, 8, 24, 26, 28, 30, 32, and unique fragments thereof. Such polypeptides are useful, for example, to regulate calcium transport-mediated cell growth, differentiation and proliferation, to generate antibodies, as components of immunoassays, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of a SOC/CRAC polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2, SEQ ID NO:4, SEQ ID NO:6, SEQ ID NO:8, SEQ ID NO:24, SEQ ID NO:26, SEQ ID NO:28, SEQ ID NO:30, and/or SEQ ID NO:32, will require longer segments to be unique while others will require only short segments, typically between 5 and 12 amino acids (e.g. 5, 6, 7, 8, 9, 10, 11 and 12 amino acids long or more, including each integer up to the full length, >1,000 amino acids long). Virtually any segment of SEQ ID NO:2, SEQ ID NO:4, SEQ ID NO:6, SEQ ID NO:8, SEQ ID NO:24, SEQ ID NO:26, SEQ ID NO:28, SEQ ID NO:30, and/or SEQ ID NO:32, excluding the ones that share identity with it (the polypeptides identified in Table II—SEQ ID NO:10, SEQ ID NO:13, SEQ ID NO:14, SEQ ID NO:15, SEQ ID NO:17, SEQ ID NO:19, and GenBank Acc. Nos. AB001535, AA592910, D86107, AF071787, Z77132, Z83117, Z68333, AA708532, AA551759, AA932133, R47363, N31660, NP003298, CAB00861, NP002411, CAA92726, CAB05572) that is 9 or more amino acids in length will be unique.

Unique fragments of a polypeptide preferably are those fragments which retain a distinct functional capability of the polypeptide. Functional capabilities which can be retained in a unique fragment of a polypeptide include $Ca^{2+}$ fluxing, high selectivity, a unitary conductance below the detection level of the patch clamp method, and/or and are subject to inhibition by high intracellular calcium levels.

One important aspect of a unique fragment is its ability to act as a signature for identifying the polypeptide. Optionally, another aspect of a unique fragment is its ability to provide an immune response in an animal. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the SOC/CRAC polypeptides described above. As used herein, a "variant" of a SOC/CRAC polypeptide is a polypeptide which contains one or more modifications to the primary amino acid sequence of a SOC/CRAC polypeptide. Modifications which create a SOC/CRAC polypeptide variant are typically made to the nucleic acid which encodes the SOC/CRAC polypeptide, and can include deletions, point mutations, truncations, amino acid substitutions and addition of amino acids or non-amino acid moieties to: 1) reduce or eliminate a calcium channel activity of a SOC/CRAC polypeptide; 2) enhance a property of a SOC/CRAC polypeptide, such as protein stability in an expression system or the stability of protein—protein binding; 3) provide a novel activity or property to a SOC/CRAC polypeptide, such as addition of an antigenic epitope or addition of a detectable moiety; or 4) to provide equivalent or better binding to a SOC/CRAC polypeptide receptor or other molecule. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the SOC/CRAC amino acid sequence. One of skill in the art will be familiar with methods for predicting the effect on protein conformation of a change in protein sequence, and can thus "design" a variant SOC/CRAC polypeptide according to known methods. One example of such a method is described by Dahiyat and Mayo in *Science* 278:82–87, 1997, whereby proteins can be designed de novo. The method can be applied to a known protein to vary only a portion of the polypeptide sequence. By applying the computational methods of Dahiyat and Mayo, specific variants of a SOC/CRAC calcium channel polypeptide can be proposed and tested to determine whether the variant retains a desired conformation.

Variants can include SOC/CRAC polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a SOC/CRAC polypeptide by eliminating proteolysis by proteases in an expression system (e.g., dibasic amino acid residues in yeast expression systems in which KEX2 protease activity is present).

Mutations of a nucleic acid which encodes a SOC/CRAC polypeptide preferably preserve the amino acid reading frame of the coding sequence and, preferably, do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant SOC/CRAC polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a SOC/CRAC gene or cDNA clone to enhance expression of the polypeptide.

The skilled artisan will realize that conservative amino acid substitutions may be made in SOC/CRAC polypeptides to provide functionally equivalent variants of the foregoing polypeptides, i.e, the variants retain the functional capabilities of the SOC/CRAC polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning. A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the SOC/CRAC polypeptides include conservative amino acid substitutions of SEQ ID NO:2, SEQ ID NO:4, SEQ ID NO:6, SEQ ID NO:8, SEQ ID NO:24, SEQ ID NO:26, SEQ ID NO:28, SEQ ID NO:30, and/or SEQ ID NO:32. Conservative substitutions of amino acids include substitutions made amongst amino acids within the following groups: (a) M, I, L, V; (b) F, Y, W; (c) K, R, H; (d) A, G; (e) St T; (f) Q, N; and (g) E, D.

Thus functionally equivalent variants of SOC/CRAC polypeptides, i.e., variants of SOC/CRAC polypeptides which retain the function of the natural SOC/CRAC polypeptides, are contemplated by the invention. Conservative amino-acid substitutions in the amino acid sequence of SOC/CRAC polypeptides to produce functionally equivalent variants of SOC/CRAC polypeptides typically are made by alteration of a nucleic acid encoding SOC/CRAC polypeptides (e.g., SEQ ID NOs:1, 3, 5, 7, 23, 25, 27, 29, 31). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a SOC/CRAC polypeptide. The activity of functionally equivalent fragments of SOC/CRAC polypeptides can be tested by cloning the gene encoding the altered SOC/CRAC polypeptide into a bacterial or mammalian expression vector, introducing the vector into an appropriate host cell, expressing the altered SOC/CRAC polypeptide, and testing for a functional capability of the SOC/CRAC polypeptides as disclosed herein (e.g., SOC/CRAC calcium channel activity).

The invention as described herein has a number of uses, some of which are described elsewhere herein. First, the invention permits isolation of SOC/CRAC polypeptides, including the isolation of the complete SOC/CRAC polypeptide. A variety of methodologies well-known to the skilled practitioner can be utilized to obtain isolated SOC/ CRAC molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of SOC/CRAC mRNA in cell-free extracts such as the reticulocyte lysate system also may be used to produce SOC/CRAC polypeptides. Those skilled in the art also can readily follow known methods for isolating SOC/CRAC polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from SOC/ CRAC polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative inactive SOC/CRAC calcium channel which interacts normally with the cell membrane but which does not mediate calcium transport can reduce calcium transport in a cell. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. See, e.g., U.S. Pat. No. 5,580,723 and Sambrook et al., 1989, *Molecular Cloning: A Laboratory Manual*, Second Edition, Cold Spring Harbor Laboratory Press. The skilled artisan then can test the population of mutagenized polypeptides for diminution in a selected and/or for retention of such an activity. Other similar methods for creating and testing dominant negative variants of a protein will be apparent to one of ordinary skill in the art.

According to another aspect, the invention provides a method for isolating a SOC/CRAC molecule having SOC/ CRAC calcium channel activity. The method involves contacting a binding molecule that is a SOC/CRAC nucleic acid or a SOC/CRAC binding polypeptide with a sample containing one or more SOC/CRAC molecules under conditions that allow such binding (see earlier discussion) to form a complex, detecting the presence of the complex, isolating the SOC/CRAC molecule from the complex, and determining whether the isolated SOC/CRAC molecule has SOC/ CRAC calcium channel activity. Thus, the invention is useful for identifying and isolating full length complementary (cDNA) or genomic nucleic acids encoding SOC/ CRAC polypeptides having SOC/CRAC calcium channel activity. Identification and isolation of such nucleic acids and polypeptides may be accomplished by hybridizing/ binding, under appropriate conditions well known in the art, libraries and/or restriction enzyme-digested human nucleic acids, with a labeled SOC/CRAC molecular probe. As used herein, a "label" includes molecules that are incorporated into, for example, a SOC/CRAC molecule (nucleic acid or peptide), that can be directly or indirectly detected. A wide variety of detectable labels are well known in the art that can be used, and include labels that provide direct detection (e.g., radioactivity, luminescence, optical or electron density, etc), or indirect detection (e.g., epitope tag such as the FLAG epitope, enzyme tag such as horseseradish peroxidase, etc.). The label may be bound to a SOC/CRAC binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradioactive energy transfers, etc. or indirectly detected with antibody conjugates, strepavidin-biotin conjugates, etc. Methods for detecting the labels are well known in the art. Once a library clone or hybridizing fragment is identified in the hybridization/binding reaction, it can be further isolated by employing standard isolation/cloning techniques known to those of skill in the art. See, generally, Sambrook et al., 1989, *Molecular Cloning: A Laboratory Manual*, 2nd Edition, Cold Spring Harbor Laboratory Press. In addition, nucleic acid amplification techniques well known in the art, may also be used to locate splice variants of calcium channel (or calcium channel subunits) with SOC/CRAC calcium channel activity. Size and sequence determinations of the amplification products can reveal splice variants.

The foregoing isolated nucleic acids and polypeptides may then be compared to the nucleic acids and polypeptides of the present invention in order to identify homogeneity or divergence of the sequences, and be further characterized functionally to determine whether they belong to a family of molecules with SOC/CRAC calcium channel activity (for methodology see under the Examples section).

The isolation of the SOC/CRAC cDNA and/or partial sequences thereof also makes it possible for the artisan to diagnose a disorder characterized by an aberrant expression of SOC/CRAC. These methods involve determining expression of the SOC/CRAC gene, and/or SOC/CRAC polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the SOC/CRAC protein.

The invention also embraces isolated peptide binding agents which, for example, can be antibodies or fragments of antibodies ("binding polypeptides"), having the ability to selectively bind to SOC/CRAC polypeptides. Antibodies include polyclonal and monoclonal antibodies, prepared according to conventional methodology. In certain embodiments, the invention excludes binding agents (e.g., antibodies) that bind to the polypeptides encoded by the nucleic acids of SEQ ID NOs:10, 12, 13, 14, 15, 17, and 19.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves binding polypeptides of numerous size and type that bind selectively to SOC/CRAC polypeptides, and complexes containing SOC/CRAC polypeptides. These binding polypeptides also may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the SOC/CRAC polypeptide or a complex containing a SOC/CRAC polypeptide. This process can be repeated through several cycles of reselection of phage that bind to the SOC/CRAC polypeptide or complex. Repeated rounds lead to enrichment of phage bearing particular sequences. DNA sequence analysis can be conducted to identify the sequences of the expressed polypeptides. The minimal linear portion of the sequence that binds to the SOC/CRAC polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the SOC/CRAC polypeptides. Thus, the SOC/CRAC polypeptides of the invention, or a fragment thereof, or complexes of SOC/CRAC can be used to screen peptide libraries, including phage display libraries, to identify and select peptide binding polypeptides that selectively bind to the SOC/CRAC polypeptides of the invention. Such molecules can be used, as described, for screening assays, for purification protocols, for interfering directly with the functioning of SOC/CRAC and for other purposes that will be apparent to those of ordinary skill in the art.

A SOC/CRAC polypeptide, or a fragment thereof, also can be used to isolate naturally occurring, polypeptide binding partners which may associate with the SOC/CRAC polypeptide in the membrane of a cell. Isolation of binding partners may be performed according to well-known methods. For example, isolated SOC/CRAC polypeptides can be attached to a substrate, and then a solution suspected of containing an SOC/CRAC binding partner may be applied to the substrate. If the binding partner for SOC/CRAC polypeptides is present in the solution, then it will bind to the substrate-bound SOC/CRAC polypeptide. The binding partner then may be isolated. Other proteins which are binding partners for SOC/CRAC, may be isolated by similar methods without undue experimentation.

The invention also provides novel kits which could be used to measure the levels of the nucleic acids of the invention, expression products of the invention or anti-SOC/CRAC antibodies. In the case of nucleic acid detection, pairs of primers for amplifying SOC/CRAC nucleic acids can be included. The preferred kits would include controls such as known amounts of nucleic acid probes, SOC/CRAC epitopes (such as SOC/CRAC expression products) or anti-SOC/CRAC antibodies, as well as instructions or other printed material. In certain embodiments the printed material can characterize risk of developing a disorder that is characterized by aberrant SOC/CRAC polypeptide expression based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with a SOC/CRAC polypeptide and a container containing labeled anti-human IgG antibodies. A well of the plate is contacted with, for example, serum, washed and then contacted with the anti-IgG antibody. The label is then detected. A kit embodying features of the present invention is comprised of the following major elements: packaging an agent of the invention, a control agent, and instructions. Packaging is a box-like structure for holding a vial (or number of vials) containing an agent of the invention, a vial (or number of vials) containing a control agent, and instructions. Individuals skilled in the art can readily modify packaging to suit individual needs.

Another aspect of the invention is a method for determining the level of SOC/CRAC expression in a subject. As used herein, a subject is a human, non-human primate, cow, horse, pig, sheep, goat, dog, cat or rodent. In all embodiments, human subjects are preferred. Expression is defined either as SOC/CRAC mRNA expression or SOC/CRAC polypeptide expression. Various methods can be used to measure expression. Preferred embodiments of the invention include PCR and Northern blotting for measuring mRNA expression, and monoclonal or polyclonal SOC/CRAC antisera as reagents to measure SOC/CRAC polypeptide expression. In certain embodiments, test samples such as biopsy samples, and biological fluids such as blood, are used as test samples. SOC/CRAC expression in a test sample of a subject is compared to SOC/CRAC expression in control sample to, e.g., assess the presence or absence or stage of a proliferative disorder (e.g., a lymphocyte proliferative disorder) in a subject.

SOC/CRAC polypeptides preferably are produced recombinantly, although such polypeptides may be isolated from biological extracts. Recombinantly produced SOC/CRAC polypeptides include chimeric proteins comprising a fusion of a SOC/CRAC protein with another polypeptide, e.g., a polypeptide capable of providing or enhancing protein—protein binding, sequence specific nucleic acid binding (such as GAL4), enhancing stability of the SOC/CRAC polypeptide under assay conditions, or providing a detectable moiety, such as green fluorescent protein. A polypeptide fused to a SOC/CRAC polypeptide or fragment may also provide means of readily detecting the fusion protein, e.g., by immunological recognition or by fluorescent labeling.

The invention is also useful in the generation of transgenic non-human animals. As used herein, "transgenic non-human animals" includes non-human animals having one or more exogenous nucleic acid molecules incorporated in germ line cells and/or somatic cells. Thus the transgenic animal include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to SOC/CRAC nucleic acid molecules to increase expression of SOC/CRAC in a regulated or conditional manner. Trans-acting negative regulators of SOC/CRAC calcium channel activity or expression also can be operably linked to a conditional promoter as described above. Such trans-acting regulators include antisense SOC/CRAC nucleic acids molecules, nucleic acid molecules which encode dominant negative SOC/CRAC molecules, ribozyme molecules specific for SOC/CRAC nucleic acids, and the like. The transgenic non-human animals are useful in experiments directed toward testing biochemical or physiological effects of diagnostics or therapeutics for conditions characterized by increased or decreased SOC/CRAC expression. Other uses will be apparent to one of ordinary skill in the art.

The invention further provides efficient methods of identifying agents or lead compounds for agents active at the level of a SOC/CRAC polypeptide (e.g., a SOC/CRAC polypeptide) or SOC/CRAC fragment dependent cellular function. In particular, such functions include interaction with other polypeptides or fragments thereof, and selective binding to certain molecules (e.g., agonists and antagonists). Generally, the screening methods involve assaying for compounds which interfere with SOC/CRAC calcium channel activity, although compounds which enhance SOC/CRAC calcium channel activity also can be assayed using the screening methods. Such methods are adaptable to automated, high throughput screening of compounds. The target therapeutic indications for pharmacological agents detected by the screening methods are limited only in that the target cellular function be subject to modulation by alteration of the formation of a complex comprising a SOC/CRAC polypeptide or fragment thereof and one or more SOC/CRAC binding targets. Target indications include cellular processes modulated by SOC/CRAC such as $Ca^{2+}$ fluxing, and affected by SOC/CRAC ability to form complexes with other molecules and polypeptides as, for example, may be present in the cell membrane.

A wide variety of assays for pharmacological agents are provided, including, expression assays, labeled in vitro protein—protein binding assays, electrophoretic mobility shift assays, immunoassays, cell-based assays such as calcium transport assays, etc. For example, two-hybrid screens are used to rapidly examine the effect of transfected nucleic acids on the intracellular binding of SOC/CRAC or SOC/CRAC fragments to specific intracellular targets (e.g. a tyrosine kinase). The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a SOC/CRAC polypeptide fused to a GAL4 DNA binding domain and a nucleic acid encoding a reporter gene operably linked to a gene expression regulatory region, such as one or more GAL4 binding sites. Activation of reporter gene transcription occurs when the SOC/CRAC and reporter fusion polypeptides bind such as to enable transcription of the reporter gene. Agents which modulate a SOC/CRAC polypeptide mediated cell function are then detected through a change in the expression of reporter gene. Methods for determining changes in the expression of a reporter gene are known in the art.

In an expression system, for example, a SOC/CRAC polypeptide is attached to a membrane, the membrane preferably separating two fluid environments and being otherwise not permeable to $Ca^{2+}$. Such separation is preferred so that a change in $Ca^{2+}$ concentration on either side of the membrane is mediated only through the attached SOC/CRAC polypeptide. Preferably, a SOC/CRAC polypeptide is expressed in an intact cell and is present on the cell-membrane (as in physiologic conditions). The cell expressing the SOC/CRAC polypeptide is preferably a eukaryotic cell, and the SOC/CRAC polypeptide is preferably recombinantly expressed, although cells naturally expressing a SOC/CRAC polypeptide may also be used. Synthetic membranes, however, containing SOC/CRAC polypeptides may also be used. See, e.g., K. Kiselyov, et al., Functional interaction between InsP3 receptors and store-operated Htrp3 channels, *Nature* 396, 478–82 (1998).

The cell expressing the SOC/CRAC polypeptide is incubated under conditions which, in the absence of the candidate agent, permit calcium flux into the cell and allow detection of a reference calcium concentration. For example, depletion of intracellular calcium stores with thapsigargin or other agents (Putney, J. W. Jr., in *Capacitative Calcium Entry*, R.G. Landes Co. and Chapman & Hall, 1997) would produce a given level of SOC/CRAC channel activation and a given reference calcium concentration. Detection of a decrease in the foregoing activities (i.e., a decrease in the intracellular calcium concentration) relative to the reference calcium concentration indicates that the candidate agent is a lead compound for an agent to inhibit SOC/CRAC calcium channel activity. Preferred SOC/CRAC polypeptides include the polypeptides of claim 15.

SOC/CRAC fragments used in the methods, when not produced by a transfected nucleic acid are added to an assay mixture as an isolated polypeptide. SOC/CRAC polypeptides preferably are produced recombinantly, although such polypeptides may be isolated from biological extracts or chemically synthesized. Recombinantly produced SOC/CRAC polypeptides include chimeric proteins comprising a fusion of a SOC/CRAC protein with another polypeptide, e.g., a polypeptide capable of providing or enhancing protein—protein binding, sequence specific nucleic acid binding (such as GAL4), enhancing stability of the SOC/CRAC polypeptide under assay conditions, or providing a detectable moiety, such as green fluorescent protein or Flag epitope.

The assay mixture is comprised of a SOC/CRAC polypeptide binding target (candidate agent) capable of interacting with a SOC/CRAC polypeptide. While natural SOC/CRAC binding targets may be used, it is frequently preferred to use portions (e.g., peptides or nucleic acid fragments) or analogs (i.e., agents which mimic the SOC/CRAC binding properties of the natural binding target for purposes of the assay) of the SOC/CRAC binding target so long as the portion or analog provides binding affinity and avidity to the SOC/CRAC polypeptide (or fragment thereof) measurable in the assay.

The assay mixture also comprises a candidate agent (binding target, e.g., agonist/antagonist). Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known agents may be subjected to directed or random chemical modifications such as acylation, alkylation, esterification, amidification, etc. to produce structural analogs of the agents. Non-SOC/CRAC calcium channel agonists and antagonists, for example, include agents such as dihydropyridines (DHPs), phenylalkylamines, omega conotoxin (omega.-CgTx) and pyrazonoylguanidines.

A variety of other reagents also can be included in the mixture. These include reagents such as salts, buffers, neutral proteins (e.g., albumin), detergents, etc. which may be used to facilitate optimal protein—protein, protein-nucleic acid, and/or protein/membrane component binding association. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate agent, the SOC/CRAC polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the SOC/CRAC polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of SOC/CRAC polypeptide interacting with a target molecule typically encodes a directly or indirectly detectable product, e.g., β-galactosidase activity, luciferase activity, and the like. For cell-free binding assays, one of the components usually comprises, or is coupled to, a detectable label. A wide variety of labels can be used, such as those that provide direct detection (e.g., radioactivity, luminescence, optical or electron density, etc.) or indirect detection (e.g., epitope tag such as the FLAG epitope, enzyme tag such as horseseradish peroxidase, etc.). The label may be bound to a SOC/CRAC binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

Of particular importance in any of the foregoing assays and binding studies is the use of a specific sequence motif identified in the SOC-2/CRAC-1 polypeptide sequence as a kinase catalytic domain. According to the invention, amino acids 999–1180 of the SOC-2/CRAC-1 polypeptide (SEQ ID NO:24) (or a fragment thereof), show a localized homology with the catalytic domains of eukaryotic elongation factor-2 kinase (eEF-2 kinase, GenBank Acc. no. U93850) and *Dictyostelium* myocin heavy chain kinase A (MHCK A, GenBank Acc. no. U16856), as disclosed in Ryazanov AG, et al., *Proc Natl Acad Sci USA*, 1997, 94(10):4884–4889. Therefore, according to the invention, a method for identifying agents useful in the modulation of SOC/CRAC polypeptide kinase activity is provided. The method involves contacting a SOC/CRAC polypeptide with kinase activity, that includes, for example, amino acids 999–1180 of the SOC-2/CRAC-1 polypeptide (SEQ ID NO:24) with a candidate agent suspected of modulating SOC/CRAC kinase activity, under conditions sufficient to allow the candidate agent to interact with the SOC/CRAC polypeptide and modulate its kinase activity; detecting a kinase activity associated with the SOC/CRAC polypeptide in the presence of the candidate agent; and comparing the kinase activity in the previous step with a control kinase activity of a SOC/CRAC polypeptide in the absence of the candidate agent to determine whether the candidate agent modulates (increases or decreases) SOC/CRAC kinase activity. Other controls for kinase activity can also be performed at the same time, for example, by utilizing eEF-2 kinase and/or *Dictyostelium* MHC Kinase A, in a similar manner to the SOC/CRAC member. Methods for performing such kinase activity assays are well known in the art.

The invention thus provides SOC/CRAC-specific binding agents, methods of identifying and making such agents, and their use in diagnosis, therapy and pharmaceutical development. For example, SOC/CRAC-specific agents are useful in a variety of diagnostic and therapeutic applications, especially where disease or disease prognosis is associated with altered SOC/CRAC and SOC/CRAC calcium channel fluxing characteristics. Novel SOC/CRAC-specific binding agents include SOC/CRAC-specific antibodies and other natural intracellular and extracellular binding agents identified with assays such as two hybrid screens, and non-natural intracellular and extracellular binding agents identified in screens of chemical libraries and the like.

In general, the specificity of SOC/CRAC binding to a specific molecule is determined by binding equilibrium constants. Targets which are capable of selectively binding a SOC/CRAC polypeptide preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate SOC/CRAC-specific binding. Cell based assays include one, two and three hybrid screens, assays in which SOC/CRAC-mediated transcription is inhibited or increased, etc. Cell free assays include SOC/CRAC-protein binding assays, immunoassays, etc. Other assays useful for screening agents which bind SOC/CRAC polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention. See, e.g., U.S. Pat. No. 5,670,488, entitled "Adenovirus Vector for Gene Therapy", issued to Gregory et al., and U.S. Pat. No. 5,672,344, entitled "Viral-Mediated Gene Transfer System", issued to Kelley et al.

The invention will be more fully understood by reference to the following examples. These examples, however, are merely intended to illustrate the embodiments of the invention and are not to be construed to limit the scope of the invention.

EXAMPLES

As an initial approach to identifying SOC/CRAC channels, we considered publicly available data and hypothesized that the following characteristics are likely to be exhibited by SOC/CRAC calcium channels: i) SOC/CRAC calcium channels would be integral membrane proteins related (probably distantly) to one of the known calcium channel families (e.g. voltage gated, ligand gated, Trp), and therefore should have a pore region formed by a tetramer of 6–7 transmembrane (TM) regions; ii) high calcium selectivity was likely to come at the price of complexity, and therefore these were likely to be large proteins; iii) the high calcium selectivity of this type of channel was likely to be useful and, therefore, highly conserved; and iv) these channels should be expressed in one or more types of lymphocytes, since ICRAC is best defined in those cell types. Since the full genome of the nematode *C. elegans* is nearing completion, and IP3-dependent calcium signals have recently been shown to be required for one or more aspects of *C. elegans* development, we took the set of proteins encoded by this genome (at the time this search was initiated WORMPEP14 was the available predicted protein set) and began searching for proteins which fit the criteria above. This search began by proceeding in alphabetical order through WORMPEP14 and arbitrarily excluding all proteins below approximately 1000 amino acids in size, followed by focusing on remaining proteins with clear TM spanning regions similar to those of other calcium channels. We stopped this screen on encountering a protein designated C05C12.3, a predicted protein of 1816 amino acids (SEQ ID NO:13). C05C12.3 was noteable because its central pore region had some sequence similarity to but was clearly distinct from members of the Trp family of calcium channels, and the hydrophobicity plot of this region showed a characteristically wide spacing between the fifth and sixth TM regions for the amino acid residues which are thought to line the channel pore region and mediate the calcium selectivity of the channels. In addition, it lacked any ankyrin repeats in the region amino-terminal to its pore region, further distinguishing it from other Trp family proteins.

We then used C05C12.3 for BLAST alignment screening of the rest of the *C. elegans* genome and also mammalian databases for homologous proteins, revealing two other *C. elegans* homologues (SEQ ID NO:14 and SEQ ID NO:15), and also a recently cloned mammalian protein named melastatin-1 (MLSN-1/SOC-1, SEQ ID NOs:9 and 10, and GenBank Acc. No. AF071787). Using these sequences, we subsequently performed an exhaustive screening of publicly accessible EST databases in search of lymphocyte homologues, but were unsuccessful in detecting any homologous transcripts in any lymphocyte lines. Since MLSN-1 (SEQ ID NOs:9 and 10) was expressed exclusively in melanocytes and retina by Northern blot hybridization and by EST database searching, there was no evidence that this type of channel was expressed in the type of cell in which ICRAC-like currents were best defined. Subsequent BLAST searches picked up mouse EST sequence A1098310 (SEQ ID NO:22) from a monocyte cell line. The I.M.A.G.E. consortium clone containing the above-identified EST was then purchased from ATCC (clone ID. 1312756, Manassas, Va.) and was further characterized. Using other portions of this sequence in EST searches, we subsequently picked up similar sequences in human B-cells (SEQ ID NOs:20 and 21), and other cell types as well (SEQ ID NOs: 11, 12, 16, 17, 18, and 19). Most of these sequences were subsequently identified to be part of the 3'-UTR or of the carboxy terminal region of the proteins, which are not readily identifiable as Trp channels, providing an explanation for the art's inability to detect any type of Trp related transcripts in lymphocytes. Partial sequences from the 5' and/or 3' ends of the above identified clones were then used to screen leukocyte and kidney cDNA libraries to extend the original sequences more toward the 5' and/or 3' ends.

In view of the foregoing, it was concluded that channels of this type were expressed in many types of lymphocytes, and therefore were members of a new family of SOC/CRAC calcium channels.

Experimental Procedures

Screening of the cDNA Libraries

Leukocyte and kidney cDNA libraries from Life Technologies (Gaithersburg, Md.) were screened using the Gene Trapper II methodology (Life Technologies) according to manufacturer's recommendation, using the inserts of I.M.A.G.E. clone ID nos. 1312756 and 1076485 from ATCC (Manassas, Va.), under stringent hybridization conditions. Using standard methodology (*Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York), individual cDNA clones were subjected to 3–4 rounds of amplification and purification under the same hybridization conditions.

After excision from the vector and subcloning of inserts into the plasmid forms, several clones were sequenced by the Beth Israel Deaconess Medical Center's Automated Sequencing Facility. Molecular biological techniques such as restriction enzyme treatment, subcloning, DNA extraction, bacterial culture and purification of DNA fragments were performed according to methods well known in the art. Computer analyses of protein and DNA sequences was done using "Assemblylign" (Oxford Molecular, Cambell, Calif.). Multiple alignments of the SOC/CRAC family members were produced using the CLUSTAL facility of the MacVector program. Restriction endonucleases, expression vectors, and modifying enzymes were purchased from commercial sources (Gibco-BRL). Sequencing vectors for DNA were purchased from Stratagene (La Jolla, Calif.).

Once the first members of what appeared to be a novel family of calcium channel receptors were identified and characterized, additional BLAST alignments were performed with the newly characterized nucleic acid sequences. An initial match was with genomic DNA fragment NH0332L11 (Genbank Acc. No. AC005538). Using this genomic sequence, promers were designed and a number of cDNA libraries was surveyed by PCR. A prostate specific message was identified and characterized, leading to the isolation and characterization of SOC-4/CRAC-3 (SEQ ID NOs: 31 and 32).

Functional Assays

Transient Expression of SOC/CRAC

In our initial transient expression experiments, we expressed or expect to express a SOC/CRAC molecule transiently in RBL-2H3 mast cells, Jurkat T cells, and A20 B-lymphocytes using both electroporation and vaccinia virus-driven expression, and measured the calcium influx produced by depletion of intracellular calcium stores with thapsigargin. Each of the foregoing techniques is well known to those of ordinary skill in the art and can be performed using various methods (see, e.g., Current Methods in Molecular Biology, eds. Ausubal, F. M., et al. 1987, Green Publishers and Wiley Interscience, N.Y., N.Y.). Exemplary methods are described herein.

Depletion of intracellular calcium stores is accomplished by treating the cells with 1 micromolar thapsigargin; alternative agents which function to deplete intracellular stores are described in by Putney, J. W. Jr., in *Capacitative Calcium Entry*, R.G. Landes Co. and Chapman & Hall, 1997 and include, for example, ionomycin, cyclopiazonic acid, and DBHQ.

Calcium influx is determined by measuring cytoplasmic calcium as indicated using the fura-2 fluorescent calcium indicator (see, e.g., G. Grynkiewicz, M. Poenie, R. Y. Tsien, A new generation of Ca2+ indicators with greatly improved fluorescence properties, *J. Biol Chem* 260, 3440–50 (1985), and M. Poenie, R. Tsien, Fura-2: a powerful new tool for measuring and imaging [Ca2+]i in single cells, *Prog Clin Biol Res* 210, 53–6 (1986)).

Patch Clamp Analysis and Determining Selectivity of SOC/CRAC

Patch clamp analysis of cells injected with SOC/CRAC cRNA is performed by using the general patch technique as described in Neher, E., "Ion channels for communication between and within cells", *Science*, 1992; 256:498–502. Specific techniques for applying the patch clamp analysis to RBL cells are described in Hoth, M., and Penner, R., "Depletion of intracellular calcium stores activates a calcium current in mast cells", *Nature*, 1992; 355:3535–355. Additional protocols for applying the patch clamp technique to other cell types are described in Putney, J. W. Jr., in *Capacitative Calcium Entry*, R.G. Landes Co. and Chapman & Hall, 1997

An exemplary protocol for patch clamp analysis of SOC/CRAC molecule expressed in RBL-2H3 mast cells using a recombinant vaccinia virus is as follows. The currents elicited by store depletion are determined using the whole cell configuration (Neher, E., *Science* 1992; 256:498–502). Currents in SOC/CRAC expressing cells are compared to currents in control cells expressing an irrelevant protein or a classic Trp family calcium channel known as VR1 (M. J. Caterina, et al., The capsaicin receptor: a heat-activated ion channel in the pain pathway [see comments], *Nature* 389, 816–24 (1997)) in order to assess the contribution of SOC/CRAC expression. In addition, the magnitude of whole cell currents in the presence of extracellular calcium (10 mM), barium (10 mM), or magnesium (10 mM) are compared to determine the relative permeability of the channels to each of these ions (Hoth, M., and Penner, R., *Nature*, 1992; 355:3535–355) and, thereby, determine the ionic selectivity.

Pharmacologic Behavior of SOC/CRAC

For analysis of the pharmacologic behavior of a SOC/CRAC molecule, a SOC/CRAC molecule is expressed in RBL-2H3 mast cells using a recombinant vaccinia virus, and the degree of calcium influx elicited by store depletion is monitored using a bulk spectrofluorimeter or a fluorescence microscope and the calcium sensitive dye fura-2 (G. Grynkiewicz, M. Poenie, R. Y. Tsien, A new generation of $Ca^{2+}$ indicators with greatly improved fluorescence properties, *J Biol Chem* 260, 3440–50 (1985) and M. Poenie, R. Tsien, Fura-2: a powerful new tool for measuring and imaging [Ca2+]i in single cells, *Prog Clin Biol Res* 210, 53–6 (1986)). The level of cytoplasmic calcium in SOC/CRAC expressing cells is compared to the level achieved in control cells expressing an irrelevant protein or a classic Trp. family calcium channels known as VR1 (M. J. Caterina, et al., The capsaicin receptor: a heat-activated ion channel in the pain pathway [see comments], *Nature* 389, 816–24 (1997)). These cells then are pre-incubated with the desired pharmacologic reagent, and again the response to store depletion is monitored. Comparison of the effect of depleting stores in SOC/CRAC expressing cells relative to controls in the presence or absence of the pharmacologic reagent is used to assess the ability of that reagent to modulate SOC/CRAC activity. Sphingosine is an exemplary molecule that can be used as pharmacologic reagents for pharmacologic characterization of SOC/CRAC calcium channels. See, e.g., Mathes, C., et al., Calcium release activated calcium current as a direct target for sphingosine, *J Biol Chem* 273(39): 25020–25030 (1998). Other non-specific calcium channel inhibitors that can be used for this purpose include SKR96365 (Calbiochem) and Lanthanum.

Bulk Calcium Assays

Bulk calcium assays can be performed in a PTI Deltascan bulk spectrofluorometer using fura-2 as described in Scharenberg A M, et al., *EMBO J,* 1995, 14(14):3385–94.

Gene Targeting

The method (and reagents) described by Buerstedde μM et al, (*Cell,* 1991, October 4;67(1):179–88), was used to generate "knockouts" in cells. Briefly, part of the chicken SOC-2/CRAC-1 genomic sequence coding for the transmembrane region was cloned utilizing the human sequence as the probe in a chicken library screen. Chicken SOC-2/CRAC-1 clones were isolated and characterized using standard methodology. The putative exon and domain arrangement of the chicken SOC-2/CRAC-1, is depicted in FIG. 1. The exons coding for TM5 (pore region) and TM6, were replaced with promoter/antibiotic cassettes (see FIG. 1). These targeting vectors were then used to target (and replace) the endogenous gene in DT-40 cells (chicken B lymphocyte cells).

Results

Example 1

Transient Expression of SOC/CRAC

In the above-identified cell lines and using both of the foregoing expression techniques, SOC/CRAC expression enhances thapsigargin-dependent influx. In addition, SOC/CRAC expression also enhances the amount of intracellular calcium stores. That this effect is likely due to SOC/CRAC acting as a plasma membrane calcium channel can be confirmed by producing an in-frame carboxy-terminal translational fusion with green fluorescent protein followed by confocal microscopy, revealing that SOC/CRAC is expressed predominantly as a plasma membrane calcium channel.

Example 2

Patch Clamp Analysis

The biophysical characteristics of SOC/CRAC enhanced currents when expressed in *Xenopus* oocytes are determined. SOC/CRAC cRNA injection is able to enhance thapsigargin-dependent whole cell currents. In addition. SOC/CRAC does not alter the reversal potential of these currents and the determination of the $P_{ca}/P_{Na}$ ratio shows that SOC/CRAC channels are highly calcium selective.

Example 3

Pharmacologic Behavior of SOC/CRAC

The pharmacologic behavior of SOC/CRAC is evaluated as described above. SOC/CRAC-enhanced influx is inhibited by sphingosine in a manner that is substantially the same as that of endogenous thapsigargin-dependent calcium influx.

Example 4

Gene Targeting

Transfection of DT-40 cells with the foregoing targeting vectors, selection for antibiotic resistance, and screening, is collectively refered to, herein, as a round of targeting. For the first round of targeting SOC-2/CRAC-1, 18/24 clones with homologous recombination of the targeting construct into one of the endogenous SOC-2/CRAC-1 alleles were obtained. On the second round of targeting (in order to target the second allele and therefore generate a homozygous SOC-2/CRAC-1 mutant cell), 0/48 clones were obtained. These results indicate that a "null" SOC-2/CRAC-1 mutation is detrimental to DT-40 cells, and that SOC-2/CRAC-1 is required for cell viability.

TABLE I

Nucleotide Sequences with homologies to SOC/CRAC nucleic acids

Sequences with SEQ ID NOs and GenBank accession numbers:

SEQ ID NO:9, AB001535, AI226731, H18835, AA419592, AA261842, AA419407, AA592910, D86107, AI098310, AF071787, Z77132, Z83117, Z68333, AA708532, AA551759, AA932133, R47363, N31660, AC005538, AA654650, AA370110, AA313170, AA493512, AI670079, AI671853.

TABLE II

Amino Acid Sequences with homologies to SOC/CRAC polypeptides

Sequences with SEQ ID NOs and GenBank accession numbers:

SEQ ID NO:10, SEQ ID NO:13, SEQ ID NO:14, SEQ ID NO:15, SEQ ID NO:17, SEQ ID NO:19, AB001535, AA592910, D86107, AF071787, Z77132, Z83117, Z68333, AA708532, AA551759, AA932133, R47363, N31660, NP003298, CAB00861, NP002411, CAA92726, CAB05572.

All references, patents, and patent documents disclosed herein are incorporated by reference herein in their entirety.

What is claimed is presented below and is followed by a Sequence Listing.

I claim:

1. An isolated nucleic acid molecule, comprising:

a nucleic acid sequence that encodes SEQ ID NO: 30, or a nucleic acid sequence that is fully complementary to the nucleic acid sequence that encodes SEQ ID NO: 30.

2. An isolated nucleic acid molecule comprising SEQ ID NO: 29, or a nucleic acid molecule that is fully complementary to the nucleic acid molecule comprising SEQ ID NO: 29.

3. An isolated polypeptide comprising the amino acid sequence of SEQ ID NO:30.

4. A pharmaceutical composition comprising:

an agent comprising the isolated polypeptide of claim 3, and a pharmaceutically acceptable carrier.

5. An isolated nucleic acid molecule comprising nucleotides 73–3714 of SEQ ID NO: 29, or a nucleic acid molecule that is fully complementary to the nucleic acid molecule comprising nucleotides 73–3714 of SEQ ID NO: 29.

6. An isolated nucleic acid molecule comprising SEQ ID NO: 25, or a nucleic acid molecule that is fully complementary to the nucleic acid molecule comprising SEQ ID NO: 25.

* * * * *

SEQUENCE LISTING

<160> NUMBER OF SEQ ID NOS: 32

<210> SEQ ID NO 1
<211> LENGTH: 1212
<212> TYPE: DNA

-continued

<213> ORGANISM: Homo sapiens

<400> SEQUENCE: 1

| | | | | | |
|---|---|---|---|---|---|
| gcacgaggca | aatttttgt | tagtacacca | tctcagccaa | gttgcaaaag | ccacttggaa | 60 |
| actggaacca | aagatcaaga | aactgtttgc | tctaaagcta | cagaaggaga | taatacagaa | 120 |
| tttggagcat | tgtaggaca | cagagatagc | atggatttac | agaggtttaa | agaaacatca | 180 |
| aacaagataa | aaatactatc | caataacaat | acttctgaaa | acactttgaa | acgagtgagt | 240 |
| tctcttgctg | gatttactga | ctgtcacaga | acttccattc | ctgttcattc | aaaacaagaa | 300 |
| aaaatcagta | gaaggccatc | taccgaagac | actcatgaag | tagattccaa | agcagcttta | 360 |
| ataccggttt | gtagatttca | actaaacaga | tatatattat | taaatacatt | aaactttttt | 420 |
| agataagatc | tacaaagtgg | tgatatttgg | gactatatca | aaaattcaaa | aaattttttc | 480 |
| ttaagaaaac | tgactttagc | atagtagcag | ttacagaaaa | gtttcttaca | gtgaatagtc | 540 |
| aggaatttta | aagaaaaatt | tatgcagaat | aaaggcagga | atctcttttt | gtttgaattg | 600 |
| aagctaatta | tatgaactca | tttccagcta | actgcgataa | tgattgattt | tgcaaattcc | 660 |
| ctttaaaagc | acacactgac | aagacaaaaa | gctcaggaaa | aggcagaaaa | attactcctt | 720 |
| tataatcaag | tattatatat | aagtcagtgc | tcataatttt | gctcaagaaa | atattgactt | 780 |
| acattcatat | atatctgttc | tggcatagag | agattatgtt | gttaaaatca | tgttattgaa | 840 |
| aaaagttatt | tcagtgggga | aagaggttag | ttaacaaaga | gattcacagt | aacaaatcct | 900 |
| cctttctgga | gggactcttc | ctgacccctga | gctgcacaac | tttgcaacaa | attaaagcct | 960 |
| aaccgaagat | gacctcacaa | tggcaattta | gaactcatgg | gagtcaactt | acataaacgg | 1020 |
| tatttgattt | ctgataagat | agtggaatta | ttggttatag | atgacaaaat | aagtatgttt | 1080 |
| aaagtgatga | tggacataaa | aaagttttaa | atataaaaca | tgagaaaaga | aggagatact | 1140 |
| attcaaaaag | actggcaaat | ttgaaaaact | agaaataaaa | aaaaaaaaaa | aaaatgagcg | 1200 |
| gccgcaagct | tt | | | | | 1212 |

<210> SEQ ID NO 2
<211> LENGTH: 141
<212> TYPE: PRT
<213> ORGANISM: Homo sapiens

<400> SEQUENCE: 2

Ala Arg Gly Lys Phe Phe Val Ser Thr Pro Ser Gln Pro Ser Cys Lys
1               5                   10                  15

Ser His Leu Glu Thr Gly Thr Lys Asp Gln Glu Thr Val Cys Ser Lys
            20                  25                  30

Ala Thr Glu Gly Asp Asn Thr Glu Phe Gly Ala Phe Val Gly His Arg
        35                  40                  45

Asp Ser Met Asp Leu Gln Arg Phe Lys Glu Thr Ser Asn Lys Ile Lys
    50                  55                  60

Ile Leu Ser Asn Asn Asn Thr Ser Glu Asn Thr Leu Lys Arg Val Ser
65                  70                  75                  80

Ser Leu Ala Gly Phe Thr Asp Cys His Arg Thr Ser Ile Pro Val His
                85                  90                  95

Ser Lys Gln Glu Lys Ile Ser Arg Arg Pro Ser Thr Glu Asp Thr His
            100                 105                 110

Glu Val Asp Ser Lys Ala Ala Leu Ile Pro Val Cys Arg Phe Gln Leu
        115                 120                 125

Asn Arg Tyr Ile Leu Leu Asn Thr Leu Asn Phe Phe Arg

-continued

```
    130              135              140
```

<210> SEQ ID NO 3
<211> LENGTH: 739
<212> TYPE: DNA
<213> ORGANISM: Homo sapiens
<220> FEATURE:
<221> NAME/KEY: Unsure
<222> LOCATION: (5)..(5)
<223> OTHER INFORMATION: a, or c, or g, or t
<220> FEATURE:
<221> NAME/KEY: Unsure
<222> LOCATION: (21)..(22)
<223> OTHER INFORMATION: a, or c, or g, or t
<220> FEATURE:
<221> NAME/KEY: Unsure
<222> LOCATION: (29)..(29)
<223> OTHER INFORMATION: a, or c, or g, or t

<400> SEQUENCE: 3

```
tcgantaggg gtcttccacc nncatactng gatgatggtt ggtgaagtct atgcatacga     60
aattgatgtg tgtgcaaacg attctgttat ccctcaaatc tgtggtcctg ggacgtggtt    120
gactccattt cttcaagcag tctacctctt tgwacagtat atcattatgg ttaatcttct    180
tattgcattt ytcaacaatg tgtatttaca agtgaaggca atttccaata ttgyatggaa    240
gtaccagcgt tatcatttta ttatggctta tcatgagaaa ccagttctgc ctcctccact    300
tatcattctt agccatatag tttctctgtt ttgctgcata tgtaagagaa gaaagaaaga    360
taagacttcc gatggaccaa aacttttctt aacagaagaa gatcaaaaga aacttcatga    420
ttttgaagag cagtgtgttg aaatgtattt caatgaaaaa gatgacaaat tcattctgg     480
gagtgaagag agaattcgtg tcacttttga aagagtggaa cagatgtgca ttcagattaa    540
agaagttgga gatccgtgtc aactacataa aaagatcatt acaatcatta gattctcaaa    600
ttggccattt gcaagatctt tcagccctga cggtagatac attaaaaaca ctcactggcc    660
aaaagcgtcg gaagctagca aagttcataa tgaaatcaca cgagaactga gcatttccaa    720
acacttggct caaaaccctt                                                739
```

<210> SEQ ID NO 4
<211> LENGTH: 235
<212> TYPE: PRT
<213> ORGANISM: Homo sapiens
<220> FEATURE:
<221> NAME/KEY: UNSURE
<222> LOCATION: (41)..(41)
<223> OTHER INFORMATION: any amino acid
<220> FEATURE:
<221> NAME/KEY: UNSURE
<222> LOCATION: (54)..(54)
<223> OTHER INFORMATION: any amino acid
<220> FEATURE:
<221> NAME/KEY: UNSURE
<222> LOCATION: (69)..(69)
<223> OTHER INFORMATION: any amino acid

<400> SEQUENCE: 4

```
Met Met Val Gly Glu Val Tyr Ala Tyr Glu Ile Asp Val Cys Ala Asn
1               5                   10                  15

Asp Ser Val Ile Pro Gln Ile Cys Gly Pro Gly Thr Trp Leu Thr Pro
            20                  25                  30

Phe Leu Gln Ala Val Tyr Leu Phe Xaa Gln Tyr Ile Ile Met Val Asn
        35                  40                  45

Leu Leu Ile Ala Phe Xaa Asn Asn Val Tyr Leu Gln Val Lys Ala Ile
    50                  55                  60
```

```
Ser Asn Ile Trp Xaa Lys Tyr Gln Arg Tyr His Phe Ile Met Ala Tyr
 65                  70                  75                  80

His Glu Lys Pro Val Leu Pro Pro Leu Ile Ile Leu Ser His Ile
                 85                  90                  95

Val Ser Leu Phe Cys Cys Ile Cys Lys Arg Arg Lys Lys Asp Lys Thr
                100                 105                 110

Ser Asp Gly Pro Lys Leu Phe Leu Thr Glu Glu Asp Gln Lys Lys Leu
                115                 120                 125

His Asp Phe Glu Glu Gln Cys Val Glu Met Tyr Phe Asn Glu Lys Asp
    130                 135                 140

Asp Lys Phe His Ser Gly Ser Glu Glu Arg Ile Arg Val Thr Phe Glu
145                 150                 155                 160

Arg Val Glu Gln Met Cys Ile Gln Ile Lys Glu Val Gly Asp Pro Cys
                165                 170                 175

Gln Leu His Lys Lys Ile Ile Thr Ile Ile Arg Phe Ser Asn Trp Pro
                180                 185                 190

Phe Ala Arg Ser Phe Ser Pro Asp Gly Arg Tyr Ile Lys Asn Thr His
            195                 200                 205

Trp Pro Lys Ala Ser Glu Ala Ser Lys Val His Asn Glu Ile Thr Arg
    210                 215                 220

Glu Leu Ser Ile Ser Lys His Leu Ala Gln Asn
225                 230                 235

<210> SEQ ID NO 5
<211> LENGTH: 1579
<212> TYPE: DNA
<213> ORGANISM: Homo sapiens
<220> FEATURE:
<221> NAME/KEY: Unsure
<222> LOCATION: (387)..(387)
<223> OTHER INFORMATION: a, or c, or g, or t
<220> FEATURE:
<221> NAME/KEY: Unsure
<222> LOCATION: (482)..(482)
<223> OTHER INFORMATION: a, or c, or g, or t

<400> SEQUENCE: 5
acgtcgcctg caggtaccgg tccggaattc ccgggtcgac ccacgcgtcc ggcatggtgt      60
tgtaaataca cttagctcct ctcttcctca aggtgatctt gaaagtaata atccttttca    120
ttgtaatatt ttaatgaaag atgacaaaga tccccagtgt aatatatttg gtcaagactt    180
acctgcagta ccccagagaa aagaatttaa ttttccagag gctggttcct cttctggtgc    240
cttattccca agtgctgttt cccctccaga actgcgacag agactacatg gggtagaact    300
cttaaaaata tttaataaaa atcaaaaatt aggcagttca tctactagca taccacatct    360
gtcatccsca csarscaaat tttttgntag tacaccatct cagccaagtt gcaaaagcca    420
cttggaaact ggaaccaaag atcaagaaac tgtttgctct aaagctacag aaggagataa    480
tncagaattt ggagcatttg taggacacag agatagcatg gatttacaga ggtttaaaga    540
aacatcaaac aagataaaaa tactatccaa taacaatact tctgaaaaca ctttgaaacg    600
agtgagttct cttgctggat ttactgactg tcacagaact tccattcctg ttcattcaaa    660
acaagaaaaa atcagtagaa ggccatctac cgaagacact catgaagtag attccaaagc    720
agctttaata ccggtttgta gatttcaact aaacagatat atattattaa atacattaaa    780 ctttttttaga taagatctac aaagtggtga tatttgggac tatatcaaaa attcaaaaaa    840 attttttctta agaaaactga ctttagcata gtagcagtta cagaaaagtt tcttacagtg    900
```

-continued

```
aatagtcagg aattttaaag aaaaatttat gcagaataaa ggcaggaatc tcttttgtt    960 tgaattgaag ctaattatat gaactcattt ccagctaact gcgataatga ttgattttgc  1020
aaattccctt taaagcaca cactgacaag acaaaaagct caggaaaagg cagaaaatt   1080 actcctttat aatcaagtat tatatataag tcagtgctca taattttgct caagaaaata  1140
ttgacttaca ttcatatata tctgttctgg catagagaga ttatgttgtt aaaatcatgt  1200
tattgaaaaa agttatttca gtggggaaag aggttagtta acaaagagat tcacagtaac  1260
aaatcctcct ttctggaggg actcttcctg accctgagct gcacaacttt gcaacaaatt  1320
aaagcctaac cgaagatgac ctcacaatgg caatttagaa ctcatgggag tcaacttaca  1380
taaacggtat ttgatttctg ataagatagt ggaattattg gttatagatg acaaataag   1440 tatgttaaa gtgatgatgg acataaaaaa gttttaaata taaaacatga gaaagaagg    1500 agatactatt caaaaagact ggcaaatttg aaaaactaga ataaaaaaa aaaaaaaaa    1560 atgagcggcc gcaagcttt                                              1579
```

<210> SEQ ID NO 6
<211> LENGTH: 243
<212> TYPE: PRT
<213> ORGANISM: Homo sapiens
<220> FEATURE:
<221> NAME/KEY: UNSURE
<222> LOCATION: (103)..(105)
<223> OTHER INFORMATION: any amino acid
<220> FEATURE:
<221> NAME/KEY: UNSURE
<222> LOCATION: (109)..(109)
<223> OTHER INFORMATION: any amino acid
<220> FEATURE:
<221> NAME/KEY: UNSURE
<222> LOCATION: (141)..(141)
<223> OTHER INFORMATION: any amino acid

<400> SEQUENCE: 6

```
Val Asn Thr Leu Ser Ser Ser Leu Pro Gln Gly Asp Leu Glu Ser Asn
 1               5                  10                  15

Asn Pro Phe His Cys Asn Ile Leu Met Lys Asp Asp Lys Asp Pro Gln
            20                  25                  30

Cys Asn Ile Phe Gly Gln Asp Leu Pro Ala Val Pro Gln Arg Lys Glu
        35                  40                  45

Phe Asn Phe Pro Glu Ala Gly Ser Ser Gly Ala Leu Phe Pro Ser
    50                  55                  60

Ala Val Ser Pro Pro Glu Leu Arg Gln Arg Leu His Gly Val Glu Leu
65                  70                  75                  80

Leu Lys Ile Phe Asn Lys Asn Gln Lys Leu Gly Ser Ser Ser Thr Ser
                85                  90                  95

Ile Pro His Leu Ser Ser Xaa Xaa Xaa Lys Phe Phe Xaa Ser Thr Pro
            100                 105                 110

Ser Gln Pro Ser Cys Lys Ser His Leu Glu Thr Gly Thr Lys Asp Gln
        115                 120                 125

Glu Thr Val Cys Ser Lys Ala Thr Glu Gly Asp Asn Xaa Glu Phe Gly
    130                 135                 140

Ala Phe Val Gly His Arg Asp Ser Met Asp Leu Gln Arg Phe Lys Glu
145                 150                 155                 160

Thr Ser Asn Lys Ile Lys Ile Leu Ser Asn Asn Thr Ser Glu Asn
                165                 170                 175

Thr Leu Lys Arg Val Ser Ser Leu Ala Gly Phe Thr Asp Cys His Arg
```

```
            180                 185                 190
Thr Ser Ile Pro Val His Ser Lys Gln Glu Lys Ile Ser Arg Arg Pro
        195                 200                 205

Ser Thr Glu Asp Thr His Glu Val Asp Ser Lys Ala Ala Leu Ile Pro
    210                 215                 220

Val Cys Arg Phe Gln Leu Asn Arg Tyr Ile Leu Leu Asn Thr Leu Asn
225                 230                 235                 240

Phe Phe Arg

<210> SEQ ID NO 7
<211> LENGTH: 3532
<212> TYPE: DNA
<213> ORGANISM: Mus musculus
<220> FEATURE:
<221> NAME/KEY: Unsure
<222> LOCATION: (2420)..(2420)
<223> OTHER INFORMATION: a, or c, or g, or t
<220> FEATURE:
<221> NAME/KEY: Unsure
<222> LOCATION: (2434)..(2434)
<223> OTHER INFORMATION: a, or c, or g, or t
<220> FEATURE:
<221> NAME/KEY: Unsure
<222> LOCATION: (2461)..(2461)
<223> OTHER INFORMATION: a, or c, or g, or t
<220> FEATURE:
<221> NAME/KEY: Unsure
<222> LOCATION: (2466)..(2466)
<223> OTHER INFORMATION: a, or c, or g, or t
<220> FEATURE:
<221> NAME/KEY: Unsure
<222> LOCATION: (2470)..(2470)
<223> OTHER INFORMATION: a, or c, or g, or t

<400> SEQUENCE: 7
attatggctt atcatgaaaa accagtcctg cctcctcctc ttatcatcct cagccatata      60
gtttcactgt tttgctgtgt atgcaaaaga agaaagaaag ataagacttc cgatgggcca     120
aaactttcct taacagaaga agatcaaaag aaactccatg attttgaaga gcagtgtgtt     180
gagatgtact tgatgagaa agatgacaaa ttcaattctg ggagtgaaga gagaatccgg      240
gtcacttttg aaagagtgga gcagatgagc attcagatta agaagttgg agatcgtgtc      300 aactacataa aaagatcatt acagtcttta gattctcaaa ttggtcatct gcaagatctc     360
tcagccctaa cagtagatac attgaaaaca cttacagccc agaaagcttc agaagctagt     420
aaagtgcaca atgagatcac acgagaattg agtatttcca acacttggc tcagaatctt      480 attgatgatg ttcctgtaag acctttgtgg gaagaaccta gtgctgtaaa cacactgagt     540
tcctctcttc ctcaaggtga tcgggaaagt aataatcctt ttctttgtaa tatttttatg     600
aaagatgaaa aagaccccca atataatctg tttggacaag atttgcccgt gatacccag      660 agaaaagaat tcaacattcc agaggctggt tcctcctgtg gtgccttatt cccaagtgct     720
gtttctcccc cagaattacg acagagacga catgggtag aaatgttaaa aatatttaat     780
aaaaatcaaa aattaggcag ttcacctaat agttcaccac atatgtcctc cccaccaacc     840
aaattttctg tgagtacccc atcccagcca gttgcaaaa gtcacttgga atccacaacc     900
aaagatcaag aacccatttt ctataaagct gcagaagggg ataacataga atttggagca     960
tttgtgggac acagagatag tatggactta cagaggttta agaaacatc aaacaaaata    1020 agagaactgt tatctaatga tactcctgaa acactctga acatgtggg tgctgctgga    1080 tatagtgaat gttgtaagac ttctacttct cttcactcgg tgcaagcaga aagctgtagt    1140
```

-continued

```
agaagagcgt cgacggaaga ctctccagaa gtcgattcta aagcagcttt gttaccggat   1200
tggttacgag atagaccatc aaacagagaa atgccatctg aaggaggaac attaaatggt   1260
cttgcttctc catttaagcc cgttttggat acaaattact attattcagc tgtggaaaga   1320
aataacctga tgaggttgtc acagagtatt cccttcgttc ctgtacctcc acgaggcgag   1380
cctgtcacag tgtaccgtct ggaggagagt tctcccagta tactgaataa cagcatgtct   1440
tcatggtctc agctaggcct ctgtgccaaa attgagtttt aagtaaaga ggaaatggaa    1500
ggtggtttac gaagagcagt caaagtgctg tgtacctggt cagagcacga tatcctgaag   1560
tcagggcatc tctatatcat taagtcattt cttcctgagg tgataaacac atggtcaagc   1620
atttataaag aagatacggt tctacatctc tgtctcagag aaatacaaca acagagagca   1680
gcacaaaagc tcacatttgc ctttaatcag atgaaaccca atccatacc atattctcca    1740
aggttccttg aagttttcct gttgtactgc cattcagcag ggcagtggtt tgctgtagaa   1800
gagtgcatga ctggtgaatt tagaaaatac aacaacaata atggtgatga aatcattcct   1860
acaaatactc tagaagagat catgctagcc tttagccact ggacctatga atataccaga   1920
ggggagttac tggtacttga cttacaagga gtgggagaaa acttgactga cccatctgta   1980
ataaaagctg aagaaaaaag atcctgtgac atggttttg gccctgccaa tctaggagaa    2040
gatgcaataa aaaacttcaa gagccaaaca tccactgtaa ttcttgctgt cgaaagctta   2100
aacttcccag atttgaagag gaatgactac acgcccttga taaaattata tttcctcagg   2160
atgagtcatc agatttgaat cttcaatctg gaaattccac caaagaatca gaagcaacaa   2220
attctgttcg tctgatgtta tagtgctgag tcattggttt ttgcctacac ttcacaaaag   2280
tgtaactgtc agttttcctt tcgggggaat tgatgatata ggaagatgtg tgcaaaatga   2340
gcttgctggc cccacacata gtctagaggt aatgttctca ttgaaaaacg cctggaggtg   2400
gaggctgcag atgccagtgn aaagtgctag ctgncagaga gtcagtgctc tcgggctggt   2460
naaggncggn acccttgctg ctgagagtgg tggttctctt cacctggtgc aggaccatta   2520
accaaagtca agtcttcaga tttgattggc tgctcagtca cagcccattc agctaaggaa   2580
actaaattgc gcagcttttt aaatggctga agtcttcctc agtttgtgct ctatgataat   2640
gatgttagct ctcaactagg tgtttgtggc cacgggagaa ctactcctta caattttgct   2700
tcacaggcat gttacaaagc ctgcactgaa aaccgtttgt cttccctctc tccctcccctc  2760
ttttccctgt agtattgagg atcaaaccca gggcctcatg aagaccattt tctaagagac   2820
attttatttta agaatcaact atagagtcta tgtttatgga tacagccagt ttttgttaaa   2880
caaaacctga attgtgcaaa agggttttttt aacatttatc aatgttaagt aaaagaaagc   2940
catgataaat aagaattaac tcactgttca atgggtgttt cctgtgagga aggttacagt   3000
tgtaacagcc tgcagttgca tacatctcca aagatttaca gacttagtgt atcaaatcag   3060
agtgtcatgt gagctctcac attgaaaatt ctataggaat gtgtcaatgt gaattctatt   3120
tctggtactt aagaaatcag ttgttggatt atccttatac agtataggga gatcacaata   3180
caactttatg ccaataaaat ctaacttaat tgcccagata ttttttgcata tttagcaaca   3240
agaaagcttt atcatttgac tcaagtttta tgctttctct ttcttttcat ttcctaggta   3300
ctaattttaa ttttttatttg gaaggagcag tgtaaagctt acttgtattc aatagtgtat   3360
ctcatagata cagacaaggc cgcagagata agctgttaaa tagtgtttaa tgttgatgtg   3420
gagagaaagg tgtattactt aaaaatacta taccatatac gttttgtata tcattaaatc   3480
tttaaaagaa attaaattta ttcttgttta aaaaaaaaaa aaaaaaaaaa aa           3532
```

<210> SEQ ID NO 8
<211> LENGTH: 475
<212> TYPE: PRT
<213> ORGANISM: Mus musculus

<400> SEQUENCE: 8

```
Ile Met Ala Tyr His Glu Lys Pro Val Leu Pro Pro Leu Ile Ile
 1               5                  10                  15

Leu Ser His Ile Val Ser Leu Phe Cys Cys Val Cys Lys Arg Arg Lys
                20                  25                  30

Lys Asp Lys Thr Ser Asp Gly Pro Lys Leu Phe Leu Thr Glu Glu Asp
            35                  40                  45

Gln Lys Lys Leu His Asp Phe Glu Glu Gln Cys Val Glu Met Tyr Phe
        50                  55                  60

Asp Glu Lys Asp Asp Lys Phe Asn Ser Gly Ser Glu Glu Arg Ile Arg
 65                  70                  75                  80

Val Thr Phe Glu Arg Val Gln Met Ser Ile Gln Ile Lys Glu Val
                85                  90                  95

Gly Asp Arg Val Asn Tyr Ile Lys Arg Ser Leu Gln Ser Leu Asp Ser
                100                 105                 110

Gln Ile Gly His Leu Gln Asp Leu Ser Ala Leu Thr Val Asp Thr Leu
            115                 120                 125

Lys Thr Leu Thr Ala Gln Lys Ala Ser Glu Ala Ser Lys Val His Asn
130                 135                 140

Glu Ile Thr Arg Glu Leu Ser Ile Ser Lys His Leu Ala Gln Asn Leu
145                 150                 155                 160

Ile Asp Asp Val Pro Val Arg Pro Leu Trp Glu Glu Pro Ser Ala Val
                165                 170                 175

Asn Thr Leu Ser Ser Ser Leu Pro Gln Gly Asp Arg Glu Ser Asn Asn
            180                 185                 190

Pro Phe Leu Cys Asn Ile Phe Met Lys Asp Glu Lys Asp Pro Gln Tyr
        195                 200                 205

Asn Leu Phe Gly Gln Asp Leu Pro Val Ile Pro Gln Arg Lys Glu Phe
    210                 215                 220

Asn Ile Pro Glu Ala Gly Ser Ser Cys Gly Ala Leu Phe Pro Ser Ala
225                 230                 235                 240

Val Ser Pro Pro Glu Leu Arg Gln Arg Arg His Gly Val Glu Met Leu
                245                 250                 255

Lys Ile Phe Asn Lys Asn Gln Lys Leu Gly Ser Ser Pro Asn Ser Ser
            260                 265                 270

Pro His Met Ser Ser Pro Pro Thr Lys Phe Ser Val Ser Thr Pro Ser
        275                 280                 285

Gln Pro Ser Cys Lys Ser His Leu Glu Ser Thr Thr Lys Asp Gln Glu
    290                 295                 300

Pro Ile Phe Tyr Lys Ala Ala Glu Gly Asp Asn Ile Glu Phe Gly Ala
305                 310                 315                 320

Phe Val Gly His Arg Asp Ser Met Asp Leu Gln Arg Phe Lys Glu Thr
                325                 330                 335

Ser Asn Lys Ile Arg Glu Leu Leu Ser Asn Asp Thr Pro Glu Asn Thr
            340                 345                 350

Leu Lys His Val Gly Ala Ala Gly Tyr Ser Glu Cys Cys Lys Thr Ser
        355                 360                 365

Thr Ser Leu His Ser Val Gln Ala Glu Ser Cys Ser Arg Arg Ala Ser
```

```
                370              375              380
Thr Glu Asp Ser Pro Glu Val Asp Ser Lys Ala Leu Leu Pro Asp
385                      390                      400

Trp Leu Arg Asp Arg Pro Ser Asn Arg Glu Met Pro Ser Glu Gly Gly
                 405                      410                 415

Thr Leu Asn Gly Leu Ala Ser Pro Phe Lys Pro Val Leu Asp Thr Asn
             420                     425                  430

Tyr Tyr Tyr Ser Ala Val Glu Arg Asn Asn Leu Met Arg Leu Ser Gln
         435                      440                  445

Ser Ile Pro Phe Val Pro Val Pro Pro Arg Gly Glu Pro Val Thr Val
     450                      455                  460

Tyr Pro Ser Gly Gly Arg Val Leu Pro Val Tyr
465                      470                  475

<210> SEQ ID NO 9
<211> LENGTH: 5433
<212> TYPE: DNA
<213> ORGANISM: Mus musculus
<220> FEATURE:
<221> NAME/KEY: Unsure
<222> LOCATION: (5094)..(5094)
<223> OTHER INFORMATION: a, or c, or g, or t

<400> SEQUENCE: 9
```

| | | | | | |
|---|---|---|---|---|---|
| ggctgaaaga | gcctgagctg | tgcctctcca | ttccactgct | gtggcagggt | cagaaatctt | 60 |
| ggatagagaa | aacctttgc | aaacgggaat | gtatctttgt | aattcctagc | acgaaagact | 120 |
| ctaacaggtg | ttgctgtggc | cagttcacca | accagcatat | ccccctctg | ccaagtgcaa | 180 |
| cacccagcaa | aaatgaagag | gaaagcaaac | aggtggagac | tcagcctgag | aaatggtctg | 240 |
| ttgccaagca | cacccagagc | tacccaacag | attcctatgg | agttcttgaa | ttccagggtg | 300 |
| gcggatattc | caataaagcc | atgtatatcc | gtgtatccta | tgacaccaag | ccagactcac | 360 |
| tgctccatct | catggtgaaa | gattggcagc | tggaactccc | caagctctta | atatctgtgc | 420 |
| atggaggcct | ccagaacttt | gagatgcagc | ccaagctgaa | acaagtcttt | gggaaaggcc | 480 |
| tgatcaaggc | tgctatgacc | accggggcct | ggatcttcac | cggggtgtc | agcacaggtg | 540 |
| ttatcagcca | cgtaggggat | gccttgaaag | accactcctc | caagtccaga | ggccgggttt | 600 |
| gtgctatagg | aattgctcca | tggggcatcg | tggagaataa | ggaagacctg | gttggaaagg | 660 |
| atgtaacaag | agtgtaccag | accatgtcca | ccctctaag | taagctctct | gtgctcaaca | 720 |
| actcccacac | ccacttcatc | ctggctgaca | atggcaccct | gggcaagtat | ggcgccgagg | 780 |
| tgaagctgcg | aaggctgctg | aaaagcaca | tctccctcca | aagatcaac | acaagactgg | 840 |
| ggcagggcgt | gccctcgtg | ggtctcgtgg | tggaggggg | ccctaacgtg | gtgtccatcg | 900 |
| tcttggaata | cctgcaagaa | gagcctccca | tccctgtggt | gatttgtgat | ggcagcggac | 960 |
| gtgcctcgga | catcctgtcc | tttgcgcaca | gtactgtga | agaaggcgga | ataataaatg | 1020 |
| agtccctcag | ggagcagctt | ctagttacca | ttcagaaaac | atttaattat | aataaggcac | 1080 |
| aatcacatca | gctgtttgca | attataatgg | agtgcatgaa | gaagaaagaa | ctcgtcactg | 1140 |
| tgttcagaat | gggttctgag | ggccagcagg | acatcgagat | ggcaatttta | actgccctgc | 1200 |
| tgaaaggaac | aaacgtatct | gctccagatc | agctgagctt | ggcactggct | tggaaccgcg | 1260 |
| tggacatagc | acgaagccag | atctttgtct | ttgggcccca | ctggacgccc | ctgggaagcc | 1320 |
| tggcacccc | gacggacagc | aaagccacgg | agaaggagaa | gaagccaccc | atggccacca | 1380 |
| ccaagggagg | aagaggaaaa | gggaaaggca | agaagaaagg | gaaagtgaaa | gaggaagtgg | 1440 |

```
aggaagaaac tgaccccegg aagatagage tgctgaactg ggtgaatgct ttggagcaag    1500
cgatgctaga tgctttagtc ttagatcgtg tcgactttgt gaagctcctg attgaaaacg    1560
gagtgaacat gcaacacttt ctgaccattc cggggctgga ggagctctat aacacaagac    1620
tgggtccacc aaacacactt catctgctgg tgagggatgt gaaaagagc aaccttccgc     1680 ctgattacca catcagcctc atagacatcg ggctcgtgct ggagtacctc atgggaggag    1740
cctaccgctg caactacact cggaaaaact ttcggaccct ttacaacaac ttgtttggac    1800
caaagaggcc taaagctctt aaacttctgg aatggaaga tgatgagcct ccagctaaag     1860
ggaagaaaaa aaaaaaaaag aaaaggagg aagagatcga cattgatgtg gacgaccctg     1920
ccgtgagtcg gttccagtat cccttccacg agctgatggt gtgggcagtg ctgatgaaac    1980
gccagaaaat ggcagtgttc ctctggcagc gagggggaaga gagcatggcc aaggccctgg   2040
tggcctgcaa gctctacaag gccatggccc acgagtcctc cgagagtgat ctggtggatg    2100
acatctccca ggacttggat aacaattcca aagacttcgg ccagcttgct ttggagttat    2160
tagaccagtc ctataagcat gacgagcaga tcgctatgaa actcctgacc tacgagctga    2220
aaaactggag caactcgacc tgcctcaaac tggccgtggc agccaaacac cgggacttca    2280
ttgctcacac ctgcagccag atgctgctga ccgatatgtg gatgggaaga ctgcggatgc    2340
ggaagaaccc cggcctgaag gttatcatgg ggattcttct acccccacc atcttgtttt     2400 tggaatttcg cacatatgat gatttctcgt atcaaacatc caaggaaaac gaggatggca    2460
aagaaaaaga agaggaaaat acggatgcaa atgcagatgc tggctcaaga aagggggatg    2520 aggaaacga gcataaaaaa cagagaagta ttcccatcgg aacaaagatc tgtgaattct     2580
ataacgcgcc cattgtcaag ttctggtttt acacaatatc atacttgggc tacctgctgc    2640
tgtttaacta cgtcatcctg gtgcggatgg atggctggcc gtccctccag gagtggatcg    2700
tcatctccta catcgtgagc ctggcgttag agaagatacg agagatcctc atgtcagaac    2760
caggcaaact cagccagaaa atcaaagttt ggcttcagga gtactggaac atcacagatc    2820
tcgtggccat ttccacattc atgattggag caattcttcg cctacagaac cagccctaca    2880
tgggctatgg ccgggtgatc tactgtgtgg atatcatctt ctggtacatc cgtgtcctgg    2940
acatctttgg tgtcaacaag tatctggggc catacgtgat gatgattgga agatgatga    3000 tcgacatgct gtactttgtg gtcatcatgc tggtcgtgct catgagtttc ggagtagccc    3060
gtcaagccat tctgcatcca gaggagaagc cctcttggaa actggcccga acatcttct    3120 acatgcccta ctggatgatc tatggagagg tgtttgcaga ccagatagac ctctacgcca    3180
tggaaattaa tcctccttgt ggtgagaacc tatatgatga ggagggcaag cggcttcctc    3240
cctgtatccc cggcgcctgg ctcactccag cactcatggc gtgctatcta ctggtcgcca    3300
acatcctgct ggtgaacctg ctgattgctg tgttcaacaa tacttcttt gaagtaaaat     3360 caatatccaa ccaggtgtgg aagttccagc gatatcagct gattatgaca tttcatgaca    3420
ggccagtcct gcccccaccg atgatcattt taagccacat ctacatcatc attatgcgtc    3480
tcagcggccg ctgcaggaaa aagagagaag gggaccaaga ggaacgggat cgtggattga    3540
agctcttcct tagcgacgag gagctaaaga ggctgcatga gttcgaggag cagtgcgtgc    3600
aggagcactt ccgggagaag gaggatgagc agcagtcgtc cagcgacgag cgcatccggg    3660
tcacttctga aagagttgaa aatatgtcaa tgaggttgga agaaatcaat gaaagagaaa    3720
cttttatgaa aacttccctg cagactgttg accttcgact tgctcagcta gaagaattat    3780
```

-continued

```
ctaacagaat ggtgaatgct cttgaaaatc ttgcgggaat cgacaggtct gacctgatcc    3840
aggcacggtc ccgggcttct tctgaatgtg aggcaacgta tcttctccgg caaagcagca    3900
tcaatagcgc tgatggctac agcttgtatc gatatcattt aacggagaa gagttattat     3960 ttgaggatac atctctctcc acgtcaccag ggacaggagt caggaaaaaa acctgttcct    4020
tccgtataaa ggaagagaag gacgtgaaaa cgcacctagt cccagaatgt cagaacagtc    4080
ttcacctttc actgggcaca agcacatcag caaccccaga tggcagtcac cttgcagtag    4140
atgacttaaa gaacgctgaa gagtcaaaat taggtccaga tattgggatt caaaggaag    4200 atgatgaaag acagacagac tctaaaaaag aagaaactat ttccccaagt ttaaataaaa    4260
cagatgtgat acatggacag gacaaatcag atgttcaaaa cactcagcta acagtggaaa    4320
cgacaaatat agaaggcact atttcctatc ccctggaaga aaccaaaatt acacgctatt    4380
tccccgatga aacgatcaat gcttgtaaaa caatgaagtc cagaagcttc gtctattccc    4440
ggggaagaaa gctggtcggt gggggttaacc aggatgtaga gtacagttca atcacggacc    4500
agcaattgac gacggaatgg caatgccaag ttcaaaagat cacgcgctct catagcacag    4560
atattcctta cattgtgtcg gaagctgcag tgcaagctga gcaaaaagag cagtttgcag    4620
atatgcaaga tgaacaccat gtcgctgaag caattcctcg aatccctcgc ttgtccctaa    4680
ccattactga cagaaatggg atggaaaact tactgtctgt gaagccagat caaactttgg    4740
gattcccatc tctcaggtca aaaagtttac atggacatcc taggaatgtg aaatccattc    4800
agggaaagtt agacagatct ggacatgcca gtagtgtaag cagcttagta attgtgtctg    4860
gaatgacagc agaagaaaaa aaggttaaga agagaaagc ttccacagaa actgaatgct    4920
agtctgtttt gtttctttaa ttttttttt taacagtcag aaacccacta atgggtgtca    4980
tcttggccca tcctaaacac atmtccaatt tcctaaaaac attttcccctt aaaaaatttt   5040 ggaaattcag acttgattta caatttaatg cactaaaagt agtatttgt tagnatatgt    5100 tagtaggctt agttttttca gttgcagtag tatcaaatga aagtgatgat actgtaacga    5160
agataaattg gctaatcagt atacaagatt atacaatctc tttattactg agggccacca    5220
aatagcctag gaagtgccct cgagcactga agtcaccatt aggtcactca agaagtaagc    5280
aactagctgg gcacagtggc tcatgcctgt aatcctagca ctttgggagg ccaaggcaga    5340
aagatagctt gagtccagga gtttgagacc agcctgggca acatagtgat accccatctc    5400
ttaaaaaaaa aaaaaaaaaa ctgccctcgt gcc                                  5433
```

<210> SEQ ID NO 10
<211> LENGTH: 1533
<212> TYPE: PRT
<213> ORGANISM: Mus musculus

<400> SEQUENCE: 10

```
Met Tyr Ile Arg Val Ser Tyr Asp Thr Lys Pro Asp Ser Leu Leu His
1               5                   10                  15

Leu Met Val Lys Asp Trp Gln Leu Glu Leu Pro Lys Leu Leu Ile Ser
            20                  25                  30

Val His Gly Gly Leu Gln Asn Phe Glu Met Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Ser Thr Gly Val Ile Ser His Val Gly Asp
65                  70                  75                  80
```

```
Ala Leu Lys Asp His Ser Ser Lys Ser Arg Gly Arg Val Cys Ala Ile
                85                  90                  95

Gly Ile Ala Pro Trp Gly Ile Val Glu Asn Lys Glu Asp Leu Val Gly
            100                 105                 110

Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
130                 135                 140

Gly Thr Leu Gly Lys Tyr Gly Ala Glu Val Lys Leu Arg Arg Leu Leu
145                 150                 155                 160

Glu Lys His Ile Ser Leu Gln Lys Ile Asn Thr Arg Leu Gly Gln Gly
                165                 170                 175

Val Pro Leu Val Gly Leu Val Glu Gly Gly Pro Asn Val Val Ser
            180                 185                 190

Ile Val Leu Glu Tyr Leu Gln Glu Pro Pro Ile Pro Val Val Ile
            195                 200                 205

Cys Asp Gly Ser Gly Arg Ala Ser Asp Ile Leu Ser Phe Ala His Lys
    210                 215                 220

Tyr Cys Glu Glu Gly Gly Ile Ile Asn Glu Ser Leu Arg Glu Gln Leu
225                 230                 235                 240

Leu Val Thr Ile Gln Lys Thr Phe Asn Tyr Asn Lys Ala Gln Ser His
                245                 250                 255

Gln Leu Phe Ala Ile Ile Met Glu Cys Met Lys Lys Lys Glu Leu Val
            260                 265                 270

Thr Val Phe Arg Met Gly Ser Glu Gly Gln Gln Asp Ile Glu Met Ala
        275                 280                 285

Ile Leu Thr Ala Leu Leu Lys Gly Thr Asn Val Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Val Phe Gly Pro His Trp Thr Pro Leu Gly Ser Leu Ala Pro
                325                 330                 335

Pro Thr Asp Ser Lys Ala Thr Glu Lys Glu Lys Lys Pro Pro Met Ala
            340                 345                 350

Thr Thr Lys Gly Gly Arg Gly Lys Gly Lys Gly Lys Lys Gly Lys
        355                 360                 365

Val Lys Glu Glu Val Glu Glu Thr Asp Pro Arg Lys Ile Glu Leu
370                 375                 380

Leu Asn Trp Val Asn Ala Leu Glu Gln Ala Met Leu Asp Ala Leu Val
385                 390                 395                 400

Leu Asp Arg Val Asp Phe Val Lys Leu Leu Ile Glu Asn Gly Val Asn
                405                 410                 415

Met Gln His Phe Leu Thr Ile Pro Arg Leu Glu Glu Leu Tyr Asn Thr
            420                 425                 430

Arg Leu Gly Pro Pro Asn Thr Leu His Leu Leu Val Arg Asp Val Lys
        435                 440                 445

Lys Ser Asn Leu Pro Pro Asp Tyr His Ile Ser Leu Ile Asp Ile Gly
    450                 455                 460

Leu Val Leu Glu Tyr Leu Met Gly Gly Ala Tyr Arg Cys Asn Tyr Thr
465                 470                 475                 480

Arg Lys Asn Phe Arg Thr Leu Tyr Asn Asn Leu Phe Gly Pro Lys Arg
                485                 490                 495

Pro Lys Ala Leu Lys Leu Leu Gly Met Glu Asp Asp Glu Pro Pro Ala
```

```
                500             505             510
Lys Gly Lys Lys Lys Lys Lys Lys Glu Glu Ile Asp Ile
        515             520             525
Asp Val Asp Asp Pro Ala Val Ser Arg Phe Gln Tyr Pro Phe His Glu
        530             535             540
Leu Met Val Trp Ala Val Leu Met Lys Arg Gln Lys Met Ala Val Phe
545             550             555             560
Leu Trp Gln Arg Gly Glu Ser Met Ala Lys Ala Leu Val Ala Cys
                565             570             575
Lys Leu Tyr Lys Ala Met Ala His Glu Ser Ser Glu Ser Asp Leu Val
            580             585             590
Asp Asp Ile Ser Gln Asp Leu Asp Asn Asn Ser Lys Asp Phe Gly Gln
            595             600             605
Leu Ala Leu Glu Leu Leu Asp Gln Ser Tyr Lys His Asp Glu Gln Ile
            610             615             620
Ala Met Lys Leu Leu Thr Tyr Glu Leu Lys Asn Trp Ser Asn Ser Thr
625             630             635             640
Cys Leu Lys Leu Ala Val Ala Ala Lys His Arg Asp Phe Ile Ala His
                645             650             655
Thr Cys Ser Gln Met Leu Leu Thr Asp Met Trp Met Gly Arg Leu Arg
                660             665             670
Met Arg Lys Asn Pro Gly Leu Lys Val Ile Met Gly Ile Leu Leu Pro
            675             680             685
Pro Thr Ile Leu Phe Leu Glu Phe Arg Thr Tyr Asp Asp Phe Ser Tyr
        690             695             700
Gln Thr Ser Lys Glu Asn Glu Asp Gly Lys Glu Lys Glu Glu Asn
705             710             715             720
Thr Asp Ala Asn Ala Asp Ala Gly Ser Arg Lys Gly Asp Glu Glu Asn
            725             730             735
Glu His Lys Lys Gln Arg Ser Ile Pro Ile Gly Thr Lys Ile Cys Glu
            740             745             750
Phe Tyr Asn Ala Pro Ile Val Lys Phe Trp Phe Tyr Thr Ile Ser Tyr
        755             760             765
Leu Gly Tyr Leu Leu Leu Phe Asn Tyr Val Ile Leu Val Arg Met Asp
    770             775             780
Gly Trp Pro Ser Leu Gln Glu Trp Ile Val Ile Ser Tyr Ile Val Ser
785             790             795             800
Leu Ala Leu Glu Lys Ile Arg Glu Ile Leu Met Ser Glu Pro Gly Lys
                805             810             815
Leu Ser Gln Lys Ile Lys Val Trp Leu Gln Glu Tyr Trp Asn Ile Thr
            820             825             830
Asp Leu Val Ala Ile Ser Thr Phe Met Ile Gly Ala Ile Leu Arg Leu
            835             840             845
Gln Asn Gln Pro Tyr Met Gly Tyr Gly Arg Val Ile Tyr Cys Val Asp
            850             855             860
Ile Ile Phe Trp Tyr Ile Arg Val Leu Asp Ile Phe Gly Val Asn Lys
865             870             875             880
Tyr Leu Gly Pro Tyr Val Met Met Ile Gly Lys Met Met Ile Asp Met
                885             890             895
Leu Tyr Phe Val Val Ile Met Leu Val Val Leu Met Ser Phe Gly Val
            900             905             910
Ala Arg Gln Ala Ile Leu His Pro Glu Glu Lys Pro Ser Trp Lys Leu
            915             920             925
```

-continued

```
Ala Arg Asn Ile Phe Tyr Met Pro Tyr Trp Met Ile Tyr Gly Glu Val
    930                 935                 940

Phe Ala Asp Gln Ile Asp Leu Tyr Ala Met Glu Ile Asn Pro Pro Cys
945                 950                 955                 960

Gly Glu Asn Leu Tyr Asp Glu Glu Gly Lys Arg Leu Pro Pro Cys Ile
                965                 970                 975

Pro Gly Ala Trp Leu Thr Pro Ala Leu Met Ala Cys Tyr Leu Leu Val
            980                 985                 990

Ala Asn Ile Leu Leu Val Asn Leu Leu Ile Ala Val Phe Asn Asn Thr
        995                 1000                1005

Phe Phe Glu Val Lys Ser Ile Ser Asn Gln Val Trp Lys Phe Gln
    1010            1015                1020

Arg Tyr Gln Leu Ile Met Thr Phe His Asp Arg Pro Val Leu Pro
    1025            1030                1035

Pro Pro Met Ile Ile Leu Ser His Ile Tyr Ile Ile Met Arg
    1040            1045                1050

Leu Ser Gly Arg Cys Arg Lys Lys Arg Glu Gly Asp Gln Glu Glu
    1055            1060                1065

Arg Asp Arg Gly Leu Lys Leu Phe Leu Ser Asp Glu Glu Leu Lys
    1070            1075                1080

Arg Leu His Glu Phe Glu Glu Gln Cys Val Gln Glu His Phe Arg
    1085            1090                1095

Glu Lys Glu Asp Glu Gln Gln Ser Ser Ser Asp Glu Arg Ile Arg
    1100            1105                1110

Val Thr Ser Glu Arg Val Glu Asn Met Ser Met Arg Leu Glu Glu
    1115            1120                1125

Ile Asn Glu Arg Glu Thr Phe Met Lys Thr Ser Leu Gln Thr Val
    1130            1135                1140

Asp Leu Arg Leu Ala Gln Leu Glu Glu Leu Ser Asn Arg Met Val
    1145            1150                1155

Asn Ala Leu Glu Asn Leu Ala Gly Ile Asp Arg Ser Asp Leu Ile
    1160            1165                1170

Gln Ala Arg Ser Arg Ala Ser Ser Glu Cys Glu Ala Thr Tyr Leu
    1175            1180                1185

Leu Arg Gln Ser Ser Ile Asn Ser Ala Asp Gly Tyr Ser Leu Tyr
    1190            1195                1200

Arg Tyr His Phe Asn Gly Glu Glu Leu Leu Phe Glu Asp Thr Ser
    1205            1210                1215

Leu Ser Thr Ser Pro Gly Thr Gly Val Arg Lys Lys Thr Cys Ser
    1220            1225                1230

Phe Arg Ile Lys Glu Glu Lys Asp Val Lys Thr His Leu Val Pro
    1235            1240                1245

Glu Cys Gln Asn Ser Leu His Leu Ser Leu Gly Thr Ser Thr Ser
    1250            1255                1260

Ala Thr Pro Asp Gly Ser His Leu Ala Val Asp Leu Lys Asn
    1265            1270                1275

Ala Glu Glu Ser Lys Leu Gly Pro Asp Ile Gly Ile Ser Lys Glu
    1280            1285                1290

Asp Asp Glu Arg Gln Thr Asp Ser Lys Lys Glu Glu Thr Ile Ser
    1295            1300                1305

Pro Ser Leu Asn Lys Thr Asp Val Ile His Gly Gln Asp Lys Ser
    1310            1315                1320
```

| | | | | | | | | | | |
|---|---|---|---|---|---|---|---|---|---|---|
| Asp | Val | Gln | Asn | Thr | Gln | Leu | Thr | Val | Glu | Thr | Thr | Asn | Ile | Glu |
| | 1325 | | | | 1330 | | | | 1335 | |
| Gly | Thr | Ile | Ser | Tyr | Pro | Leu | Glu | Glu | Thr | Lys | Ile | Thr | Arg | Tyr |
| 1340 | | | | | 1345 | | | | 1350 | |
| Phe | Pro | Asp | Glu | Thr | Ile | Asn | Ala | Cys | Lys | Thr | Met | Lys | Ser | Arg |
| 1355 | | | | | 1360 | | | | 1365 | |
| Ser | Phe | Val | Tyr | Ser | Arg | Gly | Arg | Lys | Leu | Val | Gly | Gly | Val | Asn |
| 1370 | | | | | 1375 | | | | 1380 | |
| Gln | Asp | Val | Glu | Tyr | Ser | Ser | Ile | Thr | Asp | Gln | Gln | Leu | Thr | Thr |
| 1385 | | | | | 1390 | | | | 1395 | |
| Glu | Trp | Gln | Cys | Gln | Val | Gln | Lys | Ile | Thr | Arg | Ser | His | Ser | Thr |
| 1400 | | | | | 1405 | | | | 1410 | |
| Asp | Ile | Pro | Tyr | Ile | Val | Ser | Glu | Ala | Ala | Val | Gln | Ala | Glu | Gln |
| 1415 | | | | | 1420 | | | | 1425 | |
| Lys | Glu | Gln | Phe | Ala | Asp | Met | Gln | Asp | Glu | His | His | Val | Ala | Glu |
| 1430 | | | | | 1435 | | | | 1440 | |
| Ala | Ile | Pro | Arg | Ile | Pro | Arg | Leu | Ser | Leu | Thr | Ile | Thr | Asp | Arg |
| 1445 | | | | | 1450 | | | | 1455 | |
| Asn | Gly | Met | Glu | Asn | Leu | Leu | Ser | Val | Lys | Pro | Asp | Gln | Thr | Leu |
| 1460 | | | | | 1465 | | | | 1470 | |
| Gly | Phe | Pro | Ser | Leu | Arg | Ser | Lys | Ser | Leu | His | Gly | His | Pro | Arg |
| 1475 | | | | | 1480 | | | | 1485 | |
| Asn | Val | Lys | Ser | Ile | Gln | Gly | Lys | Leu | Asp | Arg | Ser | Gly | His | Ala |
| 1490 | | | | | 1495 | | | | 1500 | |
| Ser | Ser | Val | Ser | Ser | Leu | Val | Ile | Val | Ser | Gly | Met | Thr | Ala | Glu |
| 1505 | | | | | 1510 | | | | 1515 | |
| Glu | Lys | Lys | Val | Lys | Lys | Glu | Lys | Ala | Ser | Thr | Glu | Thr | Glu | Cys |
| 1520 | | | | | 1525 | | | | 1530 | |

<210> SEQ ID NO 11
<211> LENGTH: 6220
<212> TYPE: DNA
<213> ORGANISM: Homo sapiens

<400> SEQUENCE: 11

```
tgtgcagaat tgtacagttg cgaaaccatg tcgctggcag ctggtgctgg cggtggagac      60
ttccctgtgc ggtgctcagt gcatctgcac ccgtggggga gggagctctt tctctggccc     120
tgcagtcacc tgaggttgtt accattatga acggccgctg gaccccccgc atgtgcatgt     180
actcccccag agtgtccggg ggccccagcc aagggacaca tctcacgcag ctggaacat      240
gtgcaggctg atgaagagaa ccggatgagg gcttcacatg aggaagcatg tggccaggtc     300
ctctcagaac atcagcctca tcttcctgtc tctgatctat ttcaccaacc accccatgtg     360
tctctagaac cccagtgtag cgagctggag agaggactgt cctgagggca gcaggcctgg     420
ttgcagctgg cgtgggggtc tcagaatgga gccctcagcc ctgaggaaag ctggctcgga     480
gcaggaggag ggctttgagg ggctgcccag aagggtcact gacctgggga tggtctccaa     540
tctccggcgc agcaacagca gcctcttcaa gagctgagg ctacagtgcc ccttcggcaa      600
caatgacaag caagaaagcc tcagttcgtg gattcctgaa acatcaaga agaaagaatg      660
cgtgtatttt gtggaaagtt ccaaactgtc tgatgctggg aagtggtgt gtcagtgtgg     720
ctacacgcat gagcagcact tggaggaggc taccaagccc acaccttcc agggcacaca      780
gtgggaccca agaaacatg tccaggagat gccaaccgat gcctttggcg acatcgtctt      840
cacgggcctg agccagaagg tgaaaaagta cgtccgagtc tcccaggaca cgccctccag     900
```

```
cgtgatctac cacctcatga cccagcactg ggggctggac gtccccaatc tcttgatctc    960
ggtgaccggg gggccaaga acttcaacat gaagccgcgg ctgaagagca ttttccgcag   1020
aggcctggtc aaggtggctc agaccacagg gcctggatc atcacagggg gtcccacac    1080
cggcgtcatg aagcaggtag gcgaggcggt gcgggacttc agcctgagca gcagctacaa   1140
ggaaggcgag ctcatcacca tcggagtcgc cacctgggc actgtccacc gccgcgaggg    1200
cctgatccat cccacgggca gcttccccgc cgagtacata ctggatgagg atggccaagg   1260
gaacctgacc tgcctagaca gcaaccactc tcacttcatc ctcgtggacg acgggaccca   1320
cggccagtac ggggtggaga ttcctctgag gaccaggctg agaagttca tatcggagca    1380
gaccaaggaa agaggaggtg tggccatcaa gatccccatc gtgtgcgtgg tgctggaggg   1440
cggcccgggc acgttgcaca ccatcgacaa cgccaccacc aacggcaccc cctgtgtggt   1500
tgtggagggc tcgggccgcg tggccgacgt cattgcccag gtggccaacc tgcctgtctc   1560
ggacatcact atctccctga tccagcagaa actgagcgtg ttcttccagg agatgtttga   1620
gaccttcacg gaaagcagga ttgtcgagtg gaccaaaaag atccaagata ttgtccggag   1680
gcggcagctg ctgactgtct tccgggaagg caaggatggt cagcaggacg tggatgtggc   1740
catcttgcag gccttgctga aagcctcacg gagccaagac cactttggcc acgagaactg   1800
ggaccaccag ctgaaactgg cagtggcatg gaatcgcgtg gacattgccc gcagtgagat   1860
cttcatggat gagtggcagt ggaagccttc agatctgcac cccacgatga cagctgcact   1920
catctccaac aagcctgagt ttgtgaagct cttcctggaa aacggggtgc agctgaagga   1980
gttttgtcacc tgggacacct tgctctacct gtacgagaac ctggacccct cctgcctgtt   2040
ccacagcaag ctgcaaaagg tgctggtgga ggatcccgag cgcccggctt gcgcgcccgc   2100
ggcgccccgc ctgcagatgc accacgtggc ccaggtgctg cgggagctgc tgggggactt   2160
cacgcagccg ctttatcccc ggccccggca caacgaccgg ctgcggctcc tgctgcccgt   2220
tcccacgtc aagctcaacg tgcagggagt gagcctccgg tccctctaca gcgttcctc    2280
aggccatgtg accttcacca tggaccccat ccgtgacctt tcatttggg ccattgtcca    2340
gaaccgtcgg gagctggcag gaatcatctg gctcagagc caggactgca tcgcagcggc    2400
cttggcctgc agcaagatcc tgaaggaact gtccaaggag gaggaggaca cggacagctc   2460
ggaggagatg ctggcgctgg cggaggagta tgagcacaga gccatcgggg tcttcaccga   2520
gtgctaccgg aaggacgaag agagagccca gaaactgctc acccgcgtgt ccgaggcctg   2580
ggggaagacc acctgcctgc agctcgccct ggaggccaag gacatgaagt ttgtgtctca   2640
cggggggcatc caggccttcc tgaccaaggt gtggtgggc cagctctccg tggacaatgg    2700
gctgtggcgt gtgaccctgt gcatgctggc cttcccgctg ctcctcaccg gcctcatctc   2760
cttcagggag aagaggctgc aggatgtggg cacccccgcg gcccgcgccc gtgccttctt   2820
caccgcaccc gtggtggtct tccacctgaa catcctctcc tacttcgcct tcctctgcct   2880
gttcgcctac gtgctcatgg tggacttcca gcctgtgccc tcctggtgcg agtgtgccat   2940
ctacctctgg ctcttctcct tggtgtgcga ggagatgcgg cagctcttct atgaccctga   3000
cgagtgcggg ctgatgaaga aggcagcctt gtacttcagt gacttctgga ataagctgga   3060
cgtcggcgca atcttgctct tcgtggcagg gctgaccctg ca ggctcatcc cggcgacgct  3120
gtaccccggg cgcgtcatcc tctctctgga cttcatcctg ttctgcctcc ggctcatgca   3180
cattttacc atcagtaaga cgctggggcc caagatcatc attgtgaagc ggatgatgaa    3240
```

-continued

```
ggacgtcttc ttcttcctct tcctgctggc tgtgtgggtg gtgtccttcg gggtggccaa      3300
gcaggccatc ctcatccaca acgagcgccg ggtggactgg ctgttccgag gggccgtcta      3360
ccactcctac ctcaccatct tcgggcagat cccgggctac atcgacggtg tgaacttcaa      3420
cccggagcac tgcagcccca atggcaccga cccctacaag cctaagtgcc ccgagagcga      3480
cgcgacgcag cagaggccgg ccttccctga gtggctgacg gtcctcctac tctgcctcta      3540
cctgctcttc accaacatcc tgctgctcaa cctcctcatc gccatgttca actacacctt      3600
ccagcaggtg caggagcaca cggaccagat ttggaagttc agcgccatg acctgatcga       3660 ggagtaccac ggccgccccg ccgcgccgcc cccttcatc ctcctcagcc acctgcagct       3720
cttcatcaag agggtggtcc tgaagactcc ggccaagagg cacaagcagc tcaagaacaa      3780
gctggagaag aacgaggagg cggccctgct atcctgggag atctacctga aggagaacta      3840
cctccagaac cgacagttcc agcaaaagca gcggcccgag cagaagatcg aggacatcag      3900
caataaggtt gacgccatgg tggacctgct ggacctggac ccactgaaga ggtcgggctc      3960
catggagcag aggttggcct ccctggagga gcaggtggcc cagacagccc gagccctgca      4020
ctggatcgtg aggacgctgc gggccagcgg cttcagctcg gaggcggacg tccccactct      4080
ggcctcccag aaggccgcgg aggagccgga tgctgagccg ggaggcagga agaagacgga      4140
ggagccgggc gacagctacc acgtgaatgc ccggcacctc ctctacccca actgccctgt      4200
cacgcgcttc cccgtgccca acgagaaggt gccctgggag acggagttcc tgatctatga      4260
cccacccttt tacacggcag agaggaagga cgcggccgcc atggaccccaa tgggagacac      4320 cctggagcca ctgtccacga tccagtacaa cgtggtggat ggcctgaggg accgccggag      4380
cttccacggg ccgtacacag tgcaggccgg gttgcccctg aaccccatgg ccgcacagg      4440 actgcgtggg cgcgggagcc tcagctgctt cggacccaac cacacgctgt accccatggt      4500
cacgcggtgg aggcggaacg aggatggagc catctgcagg aagagcataa agaagatgct      4560
ggaagtgctg gtggtgaagc tccctctctc cgagcactgg gccctgcctg ggggctcccg      4620
ggagccaggg gagatgctac ctcggaagct gaagcggatc ctccggcagg agcactggcc      4680
gtcttttgaa aacttgctga agtgcggcat ggaggtgtac aaaggctaca tggatgaccc      4740
gaggaacacg gacaatgcct ggatcgagac ggtggccgtc agcgtccact tccaggacca      4800
gaatgacgtg gagctgaaca ggctgaactc taacctgcac gcctgcgact cggggggcctc     4860 catccgatgg caggtggtgg acaggcgcat cccactctat gcgaaccaca agaccctcct     4920
ccagaaggca gccgctgagt tcggggctca ctactgactg tgccctcagg ctgggcggct      4980
ccagtccata gacgttcccc ccagaaacca gggcttctct ctcctgagcc tggccaggac     5040
tcaggctgtt cctgggccct gcacatgatg gggtttggtg gacccagtgc ccctcacggc     5100
tgccgcaagt ctgctgcaga tgacctcatg aactggaagg ggtcaaggtg acccgggagg     5160
agagctcaag acagggcaca ggctactcag agctgagggg cccctgggac ccttggccat     5220
caggcgaggg gctgggcctg tgcagctggg cccttggcca gagtccactc ccttcctggc     5280
tgtgtcaccc cgagcagctc atccaccatg gaggtcattg gcctgaggca gttccccgg      5340 agagtcggga tcccctgtgg cccctcagg cctatgtctg tgaggaaggg gccctgccac      5400
tctccccaag agggcctcca tgtttcgagg tgcctcaaca tggagccttg cctggctgg     5460 gctaggggca ctgtctgaac tcctgactgt caggataaac tccgtggggg tacaggagcc     5520
cagacaaagc ccaggcctgt caagagacgc agagggcccc tgccagggtt ggccccaggg     5580
accctgggac gaggctgcag aagctctccc tccctactcc ctgggagcca cgtgctggcc     5640
```

-continued

```
atgtggccag ggacggcatg agcaggaggc ggggacgtgg gggccttctg gtttggtgtc      5700
aacagctcac aggagcgtga accatgaggg ccctcaggag gggaacgtgg taaaacccaa      5760
gacattaaat ctgccatctc aggcctggct ggctcttctg tgctttccac aaataaagtt      5820
cctgacacgt ccagggccag ggctgtgtg acggctgcct gaagttctcc tcgatccccc       5880
ggtgagcttc ctgcagcctg tggatgtcct gcagcccctc agccctaccc ccaagttttct     5940 cctctgaccc atcagctccc tgtcttcatt ttcctaaacc tgggctccag catcgtcccc     6000
aagcccacca ggccaggatg caggcatcca catgccctcc tccttggctt ccctgcgtg      6060 gtggtgccaa tgtgccctgg caccctgca gaggctccgg atggagcctg gggctgcctg      6120
gccactgagc actggccgag gtgatgccca cccttccctg gacaggcctc tgtcttccac     6180
ctgacccaaa gctctctagc cacccccttg tccccagtat                            6220
```

<210> SEQ ID NO 12
<211> LENGTH: 1503
<212> TYPE: PRT
<213> ORGANISM: Homo sapiens

<400> SEQUENCE: 12

```
Met Glu Pro Ser Ala Leu Arg Lys Ala Gly Ser Glu Gln Glu Glu Gly
1               5                   10                  15

Phe Glu Gly Leu Pro Arg Arg Val Thr Asp Leu Gly Met Val Ser Asn
            20                  25                  30

Leu Arg Arg Ser Asn Ser Ser Leu Phe Lys Ser Trp Arg Leu Gln Cys
        35                  40                  45

Pro Phe Gly Asn Asn Asp Lys Gln Glu Ser Leu Ser Ser Trp Ile Pro
    50                  55                  60

Glu Asn Ile Lys Lys Lys Glu Cys Val Tyr Phe Val Glu Ser Ser Lys
65                  70                  75                  80

Leu Ser Asp Ala Gly Lys Val Val Cys Gln Cys Gly Tyr Thr His Glu
                85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His Pro
                245                 250                 255

Thr Gly Ser Phe Pro Ala Glu Tyr Ile Leu Asp Glu Asp Gly Gln Gly
            260                 265                 270
```

```
Asn Leu Thr Cys Leu Asp Ser Asn His Ser His Phe Ile Leu Val Asp
            275                 280                 285

Asp Gly Thr His Gly Gln Tyr Gly Val Glu Ile Pro Leu Arg Thr Arg
290                 295                 300

Leu Glu Lys Phe Ile Ser Glu Gln Thr Lys Glu Arg Gly Gly Val Ala
305                 310                 315                 320

Ile Lys Ile Pro Ile Val Cys Val Val Leu Glu Gly Gly Pro Gly Thr
                325                 330                 335

Leu His Thr Ile Asp Asn Ala Thr Thr Asn Gly Thr Pro Cys Val Val
            340                 345                 350

Val Glu Gly Ser Gly Arg Val Ala Asp Val Ile Ala Gln Val Ala Asn
        355                 360                 365

Leu Pro Val Ser Asp Ile Thr Ile Ser Leu Ile Gln Gln Lys Leu Ser
    370                 375                 380

Val Phe Gln Glu Met Phe Glu Thr Phe Thr Glu Ser Arg Ile Val
385                 390                 395                 400

Glu Trp Thr Lys Lys Ile Gln Asp Ile Val Arg Arg Gln Leu Leu
                405                 410                 415

Thr Val Phe Arg Glu Gly Lys Asp Gly Gln Gln Asp Val Asp Val Ala
            420                 425                 430

Ile Leu Gln Ala Leu Leu Lys Ala Ser Arg Ser Gln Asp His Phe Gly
        435                 440                 445

His Glu Asn Trp Asp His Gln Leu Lys Leu Ala Val Ala Trp Asn Arg
    450                 455                 460

Val Asp Ile Ala Arg Ser Glu Ile Phe Met Asp Glu Trp Gln Trp Lys
465                 470                 475                 480

Pro Ser Asp Leu His Pro Thr Met Thr Ala Ala Leu Ile Ser Asn Lys
                485                 490                 495

Pro Glu Phe Val Lys Leu Phe Leu Glu Asn Gly Val Gln Leu Lys Glu
            500                 505                 510

Phe Val Thr Trp Asp Thr Leu Leu Tyr Leu Tyr Glu Asn Leu Asp Pro
        515                 520                 525

Ser Cys Leu Phe His Ser Lys Leu Gln Lys Val Leu Val Glu Asp Pro
    530                 535                 540

Glu Arg Pro Ala Cys Ala Pro Ala Ala Pro Arg Leu Gln Met His His
545                 550                 555                 560

Val Ala Gln Val Leu Arg Glu Leu Leu Gly Asp Phe Thr Gln Pro Leu
                565                 570                 575

Tyr Pro Arg Pro Arg His Asn Asp Arg Leu Arg Leu Leu Pro Val
            580                 585                 590

Pro His Val Lys Leu Asn Val Gln Gly Val Ser Leu Arg Ser Leu Tyr
        595                 600                 605

Lys Arg Ser Ser Gly His Val Thr Phe Thr Met Asp Pro Ile Arg Asp
    610                 615                 620

Leu Leu Ile Trp Ala Ile Val Gln Asn Arg Arg Glu Leu Ala Gly Ile
625                 630                 635                 640

Ile Trp Ala Gln Ser Gln Asp Cys Ile Ala Ala Leu Ala Cys Ser
                645                 650                 655

Lys Ile Leu Lys Glu Leu Ser Lys Glu Glu Asp Thr Asp Ser Ser
            660                 665                 670

Glu Glu Met Leu Ala Leu Ala Glu Glu Tyr Glu His Arg Ala Ile Gly
        675                 680                 685
```

-continued

```
Val Phe Thr Glu Cys Tyr Arg Lys Asp Glu Arg Ala Gln Lys Leu
690             695             700
Leu Thr Arg Val Ser Glu Ala Trp Gly Lys Thr Thr Cys Leu Gln Leu
705                 710             715                 720
Ala Leu Glu Ala Lys Asp Met Lys Phe Val Ser His Gly Gly Ile Gln
            725             730             735
Ala Phe Leu Thr Lys Val Trp Trp Gly Gln Leu Ser Val Asp Asn Gly
            740             745             750
Leu Trp Arg Val Thr Leu Cys Met Leu Ala Phe Pro Leu Leu Leu Thr
            755             760             765
Gly Leu Ile Ser Phe Arg Glu Lys Arg Leu Gln Asp Val Gly Thr Pro
770             775             780
Ala Ala Arg Ala Arg Ala Phe Phe Thr Ala Pro Val Val Phe His
785             790             795             800
Leu Asn Ile Leu Ser Tyr Phe Ala Phe Leu Cys Leu Phe Ala Tyr Val
            805             810             815
Leu Met Val Asp Phe Gln Pro Val Pro Ser Trp Cys Glu Cys Ala Ile
            820             825             830
Tyr Leu Trp Leu Phe Ser Leu Val Cys Glu Glu Met Arg Gln Leu Phe
            835             840             845
Tyr Asp Pro Asp Glu Cys Gly Leu Met Lys Lys Ala Ala Leu Tyr Phe
850             855             860
Ser Asp Phe Trp Asn Lys Leu Asp Val Gly Ala Ile Leu Leu Phe Val
865             870             875             880
Ala Gly Leu Thr Cys Arg Leu Ile Pro Ala Thr Leu Tyr Pro Gly Arg
            885             890             895
Val Ile Leu Ser Leu Asp Phe Ile Leu Phe Cys Leu Arg Leu Met His
            900             905             910
Ile Phe Thr Ile Ser Lys Thr Leu Gly Pro Lys Ile Ile Ile Val Lys
            915             920             925
Arg Met Met Lys Asp Val Phe Phe Leu Phe Leu Leu Ala Val Trp
930             935             940
Val Val Ser Phe Gly Val Ala Lys Gln Ala Ile Leu Ile His Asn Glu
945             950             955             960
Arg Arg Val Asp Trp Leu Phe Arg Gly Ala Val Tyr His Ser Tyr Leu
            965             970             975
Thr Ile Phe Gly Gln Ile Pro Gly Tyr Ile Asp Gly Val Asn Phe Asn
            980             985             990
Pro Glu His Cys Ser Pro Asn Gly Thr Asp Pro Tyr Lys Pro Lys Cys
            995             1000            1005
Pro Glu Ser Asp Ala Thr Gln Gln Arg Pro Ala Phe Pro Glu Trp
    1010            1015            1020
Leu Thr Val Leu Leu Leu Cys Leu Tyr Leu Leu Phe Thr Asn Ile
    1025            1030            1035
Leu Leu Leu Asn Leu Leu Ile Ala Met Phe Asn Tyr Thr Phe Gln
    1040            1045            1050
Gln Val Gln Glu His Thr Asp Gln Ile Trp Lys Phe Gln Arg His
    1055            1060            1065
Asp Leu Ile Glu Glu Tyr His Gly Arg Pro Ala Ala Pro Pro Pro
    1070            1075            1080
Phe Ile Leu Leu Ser His Leu Gln Leu Phe Ile Lys Arg Val Val
    1085            1090            1095
Leu Lys Thr Pro Ala Lys Arg His Lys Gln Leu Lys Asn Lys Leu
```

-continued

```
            1100                1105                1110
Glu Lys Asn Glu Glu Ala Ala Leu Leu Ser Trp Glu Ile Tyr Leu
    1115                1120                1125
Lys Glu Asn Tyr Leu Gln Asn Arg Gln Phe Gln Gln Lys Gln Arg
    1130                1135                1140
Pro Glu Gln Lys Ile Glu Asp Ile Ser Asn Lys Val Asp Ala Met
    1145                1150                1155
Val Asp Leu Leu Asp Leu Asp Pro Leu Lys Arg Ser Gly Ser Met
    1160                1165                1170
Glu Gln Arg Leu Ala Ser Leu Glu Glu Gln Val Ala Gln Thr Ala
    1175                1180                1185
Arg Ala Leu His Trp Ile Val Arg Thr Leu Arg Ala Ser Gly Phe
    1190                1195                1200
Ser Ser Glu Ala Asp Val Pro Thr Leu Ala Ser Gln Lys Ala Ala
    1205                1210                1215
Glu Glu Pro Asp Ala Glu Pro Gly Gly Arg Lys Lys Thr Glu Glu
    1220                1225                1230
Pro Gly Asp Ser Tyr His Val Asn Ala Arg His Leu Leu Tyr Pro
    1235                1240                1245
Asn Cys Pro Val Thr Arg Phe Pro Val Pro Asn Glu Lys Val Pro
    1250                1255                1260
Trp Glu Thr Glu Phe Leu Ile Tyr Asp Pro Pro Phe Tyr Thr Ala
    1265                1270                1275
Glu Arg Lys Asp Ala Ala Ala Met Asp Pro Met Gly Asp Thr Leu
    1280                1285                1290
Glu Pro Leu Ser Thr Ile Gln Tyr Asn Val Val Asp Gly Leu Arg
    1295                1300                1305
Asp Arg Arg Ser Phe His Gly Pro Tyr Thr Val Gln Ala Gly Leu
    1310                1315                1320
Pro Leu Asn Pro Met Gly Arg Thr Gly Leu Arg Gly Arg Gly Ser
    1325                1330                1335
Leu Ser Cys Phe Gly Pro Asn His Thr Leu Tyr Pro Met Val Thr
    1340                1345                1350
Arg Trp Arg Arg Asn Glu Asp Gly Ala Ile Cys Arg Lys Ser Ile
    1355                1360                1365
Lys Lys Met Leu Glu Val Leu Val Val Lys Leu Pro Leu Ser Glu
    1370                1375                1380
His Trp Ala Leu Pro Gly Gly Ser Arg Glu Pro Gly Glu Met Leu
    1385                1390                1395
Pro Arg Lys Leu Lys Arg Ile Leu Arg Gln Glu His Trp Pro Ser
    1400                1405                1410
Phe Glu Asn Leu Leu Lys Cys Gly Met Glu Val Tyr Lys Gly Tyr
    1415                1420                1425
Met Asp Asp Pro Arg Asn Thr Asp Asn Ala Trp Ile Glu Thr Val
    1430                1435                1440
Ala Val Ser Val His Phe Gln Asp Gln Asn Asp Val Glu Leu Asn
    1445                1450                1455
Arg Leu Asn Ser Asn Leu His Ala Cys Asp Ser Gly Ala Ser Ile
    1460                1465                1470
Arg Trp Gln Val Val Asp Arg Arg Ile Pro Leu Tyr Ala Asn His
    1475                1480                1485
Lys Thr Leu Leu Gln Lys Ala Ala Ala Glu Phe Gly Ala His Tyr
    1490                1495                1500
```

<210> SEQ ID NO 13
<211> LENGTH: 1816
<212> TYPE: PRT
<213> ORGANISM: Caenorhabditis elegans

<400> SEQUENCE: 13

| | | | | | | | | | | | | | | |
|---|---|---|---|---|---|---|---|---|---|---|---|---|---|---|
| Met | Ile | Thr | Asp | Lys | Asn | Leu | Phe | Ser | Arg | Leu | Leu | Ile | Lys | Asn |
| 1 | | | | 5 | | | | | 10 | | | | | 15 |
| Pro | Ile | Arg | Met | His | Ser | Pro | Ser | Phe | Ser | Phe | Ser | Leu | Ile | Thr | Ser |
| | | | 20 | | | | | 25 | | | | | 30 | | |
| Leu | Phe | Phe | Thr | Gln | Phe | Phe | Met | Phe | Gln | Leu | Ser | Ser | Met | Ala | Tyr |
| | | | 35 | | | | | 40 | | | | | 45 | | |
| Phe | Phe | Leu | Thr | Leu | Ile | Ala | Gly | Val | Thr | His | Phe | Tyr | Phe | Pro | Glu |
| | | 50 | | | | | 55 | | | | | 60 | | | |
| Lys | Leu | Leu | Gly | Lys | Ser | Glu | Asn | Leu | Asp | His | Arg | Tyr | Gln | Ser | Ser |
| 65 | | | | | 70 | | | | | 75 | | | | | 80 |
| Glu | Gln | Lys | Val | Leu | Ile | Glu | Trp | Thr | Glu | Asn | Lys | Ala | Val | Ala | Glu |
| | | | | 85 | | | | | 90 | | | | | 95 | |
| Ser | Leu | Arg | Ala | Asn | Ser | Val | Thr | Val | Glu | Glu | Asn | Glu | Ser | Glu | Arg |
| | | | 100 | | | | | 105 | | | | | 110 | | |
| Glu | Thr | Glu | Thr | Gln | Thr | Lys | Arg | Arg | Arg | Lys | Lys | Gln | Arg | Ser | Thr |
| | | | 115 | | | | | 120 | | | | | 125 | | |
| Ser | Ser | Asp | Lys | Ala | Pro | Leu | Asn | Ser | Ala | Pro | Arg | His | Val | Gln | Lys |
| | 130 | | | | | 135 | | | | | 140 | | | | |
| Phe | Asp | Trp | Lys | Asp | Met | Leu | His | Leu | Ala | Asp | Ile | Ser | Gly | Arg | Lys |
| 145 | | | | | 150 | | | | | 155 | | | | | 160 |
| Arg | Gly | Asn | Ser | Thr | Thr | Ser | His | Ser | Gly | His | Ala | Thr | Arg | Ala | Gly |
| | | | | 165 | | | | | 170 | | | | | 175 | |
| Ser | Leu | Lys | Gly | Lys | Asn | Trp | Ile | Glu | Cys | Arg | Leu | Lys | Met | Arg | Gln |
| | | | 180 | | | | | 185 | | | | | 190 | | |
| Cys | Ser | Tyr | Phe | Val | Pro | Ser | Gln | Arg | Phe | Ser | Glu | Arg | Cys | Gly | Cys |
| | | | 195 | | | | | 200 | | | | | 205 | | |
| Gly | Lys | Glu | Arg | Ser | Lys | His | Thr | Glu | Glu | Val | Leu | Glu | Arg | Ser | Gln |
| | 210 | | | | | 215 | | | | | 220 | | | | |
| Asn | Lys | Asn | His | Pro | Leu | Asn | His | Leu | Thr | Leu | Pro | Gly | Ile | His | Glu |
| 225 | | | | | 230 | | | | | 235 | | | | | 240 |
| Val | Asp | Thr | Thr | Asp | Ala | Asp | Ala | Asp | Asp | Asn | Glu | Val | Asn | Leu | Thr |
| | | | | 245 | | | | | 250 | | | | | 255 | |
| Pro | Gly | Arg | Trp | Ser | Ile | Gln | Ser | His | Thr | Glu | Ile | Val | Pro | Thr | Asp |
| | | | 260 | | | | | 265 | | | | | 270 | | |
| Ala | Tyr | Gly | Asn | Ile | Val | Phe | Glu | Gly | Thr | Ala | His | His | Ala | Gln | Tyr |
| | | | 275 | | | | | 280 | | | | | 285 | | |
| Ala | Arg | Ile | Ser | Phe | Asp | Ser | Asp | Pro | Arg | Asp | Ile | Val | His | Leu | Met |
| | 290 | | | | | 295 | | | | | 300 | | | | |
| Met | Lys | Val | Trp | Lys | Leu | Lys | Pro | Pro | Lys | Leu | Ile | Ile | Thr | Ile | Asn |
| 305 | | | | | 310 | | | | | 315 | | | | | 320 |
| Gly | Gly | Leu | Thr | Lys | Phe | Asp | Leu | Gln | Pro | Lys | Leu | Ala | Arg | Thr | Phe |
| | | | | 325 | | | | | 330 | | | | | 335 | |
| Arg | Lys | Gly | Ile | Met | Lys | Ile | Ala | Lys | Ser | Thr | Asp | Ala | Trp | Ile | Ile |
| | | | 340 | | | | | 345 | | | | | 350 | | |
| Thr | Ser | Gly | Leu | Asp | Glu | Gly | Val | Val | Lys | His | Leu | Asp | Ser | Ala | Leu |
| | | | 355 | | | | | 360 | | | | | 365 | | |
| His | Ala | Leu | Glu | Phe | Trp | Ser | Phe | Gly | Leu | Phe | Trp | Val | Ile | Gln | Leu |

-continued

```
            370                 375                 380
Asp Val Leu Leu Ala His Ser Met Phe Ile Pro Arg Gly Ser Leu Phe
385                 390                 395                 400
Asp His Gly Asn His Thr Ser Lys Asn His Val Val Ala Ile Gly Ile
                    405                 410                 415
Ala Ser Trp Gly Met Leu Lys Gln Arg Ser Arg Phe Val Gly Lys Asp
                420                 425                 430
Ser Thr Val Thr Tyr Ala Thr Asn Val Phe Asn Asn Thr Arg Leu Lys
            435                 440                 445
Glu Leu Asn Asp Asn His Ser Tyr Phe Leu Phe Ser Asp Asn Gly Thr
450                 455                 460
Val Asn Arg Tyr Gly Ala Glu Ile Ile Met Arg Lys Arg Leu Glu Ala
465                 470                 475                 480
Tyr Leu Ala Gln Gly Asp Lys Lys Arg Ser Ala Ile Pro Leu Val Cys
                485                 490                 495
Val Val Leu Glu Gly Gly Ala Phe Thr Ile Lys Met Val His Asp Tyr
                500                 505                 510
Val Thr Thr Ile Pro Arg Ile Pro Val Ile Val Cys Asp Gly Ser Gly
            515                 520                 525
Arg Ala Ala Asp Ile Leu Ala Phe Ala His Gln Ala Val Ser Gln Asn
530                 535                 540
Gly Phe Leu Ser Asp Asn Ile Arg Asn Gln Leu Val Asn Ile Val Arg
545                 550                 555                 560
Arg Ile Phe Gly Tyr Asp Pro Lys Thr Ala Gln Lys Leu Ile Lys Gln
                565                 570                 575
Ile Val Glu Cys Ser Thr Asn Lys Ser Leu Met Thr Ile Phe Arg Leu
                580                 585                 590
Gly Glu Ser Ser Arg Glu Asp Leu Asp His Val Ile Met Ser Cys Leu
            595                 600                 605
Leu Lys Gly Gln Asn Leu Ser Pro Pro Glu Gln Leu Gln Leu Ala Leu
610                 615                 620
Ala Trp Asn Arg Ala Asp Ile Ala Arg Thr Glu Ile Phe Ala Asn Gly
625                 630                 635                 640
Thr Glu Trp Thr Thr Gln Asp Leu His Asn Ala Met Ile Glu Ala Leu
                645                 650                 655
Ser Asn Asp Arg Ile Asp Phe Val His Leu Leu Leu Glu Asn Gly Val
                660                 665                 670
Ser Met Gln Lys Phe Leu Thr Tyr Gly Arg Leu Glu His Leu Tyr Asn
            675                 680                 685
Thr Asp Lys Gly Pro Gln Asn Thr Leu Arg Thr Asn Leu Leu Val Asp
690                 695                 700
Ser Lys His His Ile Lys Leu Val Glu Val Gly Arg Leu Val Glu Asn
705                 710                 715                 720
Leu Met Gly Asn Leu Tyr Lys Ser Asn Tyr Thr Lys Glu Glu Phe Lys
                725                 730                 735
Asn Gln Tyr Phe Leu Phe Asn Asn Arg Lys Gln Phe Gly Lys Arg Val
                740                 745                 750
His Ser Asn Ser Asn Gly Gly Arg Asn Asp Val Ile Gly Pro Ser Gly
            755                 760                 765
Asp Ala Gly Arg Glu Arg Met Ser Ser Met Gln Ile Ser Leu Ile Asn
770                 775                 780
Asn Ala Arg Asn Ser Ile Ile Ser Leu Phe Asn Gly Gly Gly Arg Lys
785                 790                 795                 800
```

-continued

```
Arg Glu Ser Asp Asp Glu Asp Phe Ser Asn Leu Glu Glu Ala
            805                 810                 815

Asn Met Asp Phe Thr Phe Arg Tyr Pro Tyr Ser Asp Leu Met Ile Trp
            820                 825                 830

Ala Val Leu Thr Lys Arg Gln Lys Met Ala Lys Leu Met Trp Thr His
            835                 840                 845

Gly Glu Glu Gly Met Ala Lys Ala Leu Val Ala Ser Arg Leu Tyr Val
            850                 855                 860

Ser Leu Ala Lys Thr Ala Ser Leu Ala Thr Gly Glu Ile Gly Met Ser
865                 870                 875                 880

Gln Asp Phe Thr Glu Phe Ser Asp Glu Phe Ser Glu Leu Ala Val Glu
            885                 890                 895

Val Leu Glu Tyr Cys Thr Lys His Gly Arg Asp Gln Thr Leu Arg Leu
            900                 905                 910

Leu Thr Cys Glu Leu Ala Asn Trp Gly Asp Glu Thr Cys Leu Ser Leu
            915                 920                 925

Ala Ala Asn Asn Gly His Arg Lys Phe Leu Ala His Pro Cys Cys Gln
            930                 935                 940

Met Leu Leu Ser Asp Leu Trp Gln Gly Gly Leu Leu Met Lys Asn Asn
945                 950                 955                 960

Gln Asn Ser Lys Val Leu Thr Cys Leu Ala Ala Pro Pro Leu Ile Phe
            965                 970                 975

Leu Leu Gly Phe Lys Thr Lys Glu Gln Leu Met Leu Gln Pro Lys Thr
            980                 985                 990

Ala Ala Glu His Asp Glu Glu Met  Ser Asp Ser Glu Met  Asn Ser Ala
            995                 1000                1005

Glu Asp  Thr Asp Thr Ser Ser  Asp Ser Ser Ser Asp   Ser Asp Asp
    1010                1015                1020

Ser Asp  Glu Glu Asp Ala Lys  Leu Arg Ala Gln Ser   Leu Ser Ala
    1025                1030                1035

Asp Gln  Pro Leu Ser Ile His  Arg Leu Val Arg Asp   Lys Leu Asn
    1040                1045                1050

Phe Ser  Glu Lys Lys Lys Pro  Asp Met Gly Ile Ser   Arg Ile Val
    1055                1060                1065

Val Ala  Pro Pro Ile Val Thr  Gly Arg Asn Arg Ala   Arg Thr Met
    1070                1075                1080

Ser Ile  Lys Lys Ser Lys Lys  Asn Val Ile Lys Pro   Pro Ala Cys
    1085                1090                1095

Leu Lys  Ile Glu Thr Ser Asp  Asp Glu Gln Glu   Gln Lys Lys
    1100                1105                1110

Ala Thr  Glu Met Cys Lys Ser  Thr Phe Phe Asp Phe   Phe Asp
    1115                1120                1125

Phe Pro  Tyr Ile Asn Arg Thr  Gly Lys Arg Gly Ser   Val Ala Val
    1130                1135                1140

Ala Met  Asn His Asp Asp Met  Tyr Ile Asp Pro Ser   Glu Glu Leu
    1145                1150                1155

Asp Thr  Gln Thr Arg Gln Lys  Ser Ser Arg Glu Phe   Ser Ser Ser
    1160                1165                1170

Arg Asn  Val Thr Val Gln Val  Tyr Thr Gln Arg Pro   Leu Ser Trp
    1175                1180                1185

Lys Lys  Lys Ile Met Glu Phe  Tyr Lys Ala Pro Ile   Thr Thr Tyr
    1190                1195                1200
```

-continued

```
Trp Leu Trp Phe Phe Ala Phe Ile Trp Phe Leu Ile Leu Leu Thr
1205                1210                1215

Tyr Asn Leu Leu Val Lys Thr Gln Arg Ile Ala Ser Trp Ser Glu
1220                1225                1230

Trp Tyr Val Phe Ala Tyr Ile Phe Val Trp Thr Leu Glu Ile Gly
1235                1240                1245

Arg Lys Val Val Ser Thr Ile Met Met Asp Thr Ser Lys Pro Val
1250                1255                1260

Leu Lys Gln Leu Arg Val Phe Phe Gln Tyr Arg Asn Gly Leu
1265                1270                1275

Leu Ala Phe Gly Leu Leu Thr Tyr Leu Ile Ala Tyr Phe Ile Arg
1280                1285                1290

Leu Ser Pro Thr Thr Lys Thr Leu Gly Arg Ile Leu Ile Ile Cys
1295                1300                1305

Asn Ser Val Ile Trp Ser Leu Lys Leu Val Asp Tyr Leu Ser Val
1310                1315                1320

Gln Gln Gly Leu Gly Pro Tyr Ile Asn Ile Val Ala Glu Met Ile
1325                1330                1335

Pro Thr Met Ile Pro Leu Cys Val Leu Val Phe Ile Thr Leu Tyr
1340                1345                1350

Ala Phe Gly Leu Leu Arg Gln Ser Ile Thr Tyr Pro Tyr Glu Asp
1355                1360                1365

Trp His Trp Ile Leu Val Arg Asn Ile Phe Leu Gln Pro Tyr Phe
1370                1375                1380

Met Leu Tyr Gly Glu Val Tyr Ala Ala Glu Ile Asp Thr Cys Gly
1385                1390                1395

Asp Glu Ile Trp Gln Thr His Glu Asp Glu Asn Ile Pro Ile Ser
1400                1405                1410

Met Leu Asn Val Thr His Glu Thr Cys Val Pro Gly Tyr Trp Ile
1415                1420                1425

Ala Pro Val Gly Leu Thr Val Phe Met Leu Ala Thr Asn Val Leu
1430                1435                1440

Leu Met Asn Val Met Val Ala Gly Cys Thr Tyr Ile Phe Glu Lys
1445                1450                1455

His Ile Gln Ser Thr Arg Glu Ile Phe Leu Phe Glu Arg Tyr Gly
1460                1465                1470

Gln Val Met Glu Tyr Glu Ser Thr Pro Trp Leu Pro Pro Pro Phe
1475                1480                1485

Thr Ile Ile Tyr His Val Ile Trp Leu Phe Lys Leu Ile Lys Ser
1490                1495                1500

Ser Ser Arg Met Phe Glu Arg Lys Asn Leu Phe Asp Gln Ser Leu
1505                1510                1515

Lys Leu Phe Leu Ser Pro Asp Glu Met Glu Lys Val His Thr Phe
1520                1525                1530

Glu Glu Glu Ser Val Glu Asp Met Lys Arg Glu Thr Glu Lys Lys
1535                1540                1545

Asn Leu Ser Ser Asn Asp Glu Arg Ile His Arg Thr Ala Glu Arg
1550                1555                1560

Thr Asp Ala Ile Leu Asn Arg Val Ser His Leu Thr Gln Leu Glu
1565                1570                1575

Phe Thr Leu Lys Glu Glu Ile Arg Glu Leu Glu His Lys Met Lys
1580                1585                1590

Asn Met Asp Ser Arg His Lys Glu Gln Met Asn Leu Met Leu Asp
```

```
                    1595                1600                1605

Met Asn Lys Lys Leu Gly Lys Phe Ile Ser Gly Lys Tyr Lys Arg
         1610                1615                1620

Gly Ser Phe Gly Gly Ser Gly Ser Asp Gly Gly Gly Gly Ser Ser
         1625                1630                1635

Asp Asn Ser Lys Leu Glu Pro Asn Asn Ser Val Pro Met Ile Thr
         1640                1645                1650

Val Asp Gly Pro Ser Pro Ile Gly Ser Arg Arg Thr Ser Gly Gln
         1655                1660                1665

Tyr Leu Lys Arg Asp Ser Leu Gln Ala Lys Lys Lys Ile Thr Glu
         1670                1675                1680

Asn Arg Arg Ser Ser Leu Glu Gln Pro Lys Ile Pro Ser Ile Gln
         1685                1690                1695

Phe Asn Leu Met Glu Asp Gln Asp Glu Ser Ala Ala Glu Ser Ala
         1700                1705                1710

Thr Glu Glu Val Ser Ile Ser Ile Pro Val Pro Gln Met Arg Val
         1715                1720                1725

Arg Gln Val Thr Glu Ser Asp Lys Ser Asp Leu Ser Glu Asp Asp
         1730                1735                1740

Leu Ile Thr Arg Glu Asp Ala Pro Pro Thr Ser Ile Asn Leu Pro
         1745                1750                1755

Arg Gly Pro Arg Arg His Ala Leu Tyr Ser Thr Ile Ala Asp Ala
         1760                1765                1770

Ile Glu Thr Glu Asp Asp Phe Tyr Ala Asp Ser Pro Val Pro Met
         1775                1780                1785

Pro Met Thr Pro Val Gln Pro Ala Asp Gly Ser Phe Phe Gly Glu
         1790                1795                1800

Asn Asp Ser Arg Tyr Gln Arg Asp Asp Ser Asp Tyr Glu
         1805                1810                1815

<210> SEQ ID NO 14
<211> LENGTH: 1387
<212> TYPE: PRT
<213> ORGANISM: Caenorhabditis elegans

<400> SEQUENCE: 14

Met Arg Lys Ser Arg Arg Val Arg Lys Leu Val Arg His Ala Ser Leu
1               5                   10                  15

Ile Glu Asn Ile Arg His Arg Thr Ser Ser Phe Leu Arg Leu Leu Asn
                20                  25                  30

Ala Pro Arg Asn Ser Met Cys Asn Ala Asn Thr Val His Ser Ile Ser
            35                  40                  45

Ser Phe Arg Ser Asp His Leu Ser Arg Lys Ser Thr His Lys Phe Leu
        50                  55                  60

Asp Asn Pro Asn Leu Phe Ala Ile Glu Leu Thr Glu Lys Leu Ser Pro
65                  70                  75                  80

Pro Trp Ile Glu Asn Thr Phe Glu Lys Arg Glu Cys Ile Arg Phe Ala
                85                  90                  95

Ala Leu Pro Lys Asp Pro Glu Arg Cys Gly Cys Gly Arg Pro Leu Ser
            100                 105                 110

Ala His Thr Pro Ala Ser Thr Phe Phe Ser Thr Leu Pro Val His Leu
        115                 120                 125

Leu Glu Lys Glu Gln Gln Thr Trp Thr Ile Ala Asn Asn Thr Gln Thr
    130                 135                 140
```

```
Ser Thr Thr Asp Ala Phe Gly Thr Ile Val Phe Gln Gly Gly Ala His
145                 150                 155                 160

Ala His Lys Ala Gln Tyr Val Arg Leu Ser Tyr Asp Ser Glu Pro Leu
                165                 170                 175

Asp Val Met Tyr Leu Met Glu Lys Val Trp Gly Leu Glu Ala Pro Arg
            180                 185                 190

Leu Val Ile Thr Val His Gly Gly Met Ser Asn Phe Glu Leu Glu Glu
                195                 200                 205

Arg Leu Gly Arg Leu Phe Arg Lys Gly Met Leu Lys Ala Ala Gln Thr
        210                 215                 220

Thr Gly Ala Trp Ile Ile Thr Ser Gly Leu Asp Ser Gly Val Val Arg
225                 230                 235                 240

His Val Ala Lys Ala Leu Asp Glu Ala Gly Ile Ser Ala Arg Met Arg
                245                 250                 255

Ser Gln Ile Val Thr Ile Gly Ile Ala Pro Trp Gly Val Ile Lys Arg
            260                 265                 270

Lys Glu Arg Leu Ile Arg Gln Asn Glu His Val Tyr Tyr Asp Val His
        275                 280                 285

Ser Leu Ser Val Asn Ala Asn Val Gly Ile Leu Asn Asp Arg His Ser
290                 295                 300

Tyr Phe Leu Leu Ala Asp Asn Gly Thr Val Gly Arg Phe Gly Ala Asp
305                 310                 315                 320

Leu His Leu Arg Gln Asn Leu Glu Asn His Ile Ala Thr Phe Gly Cys
                325                 330                 335

Asn Gly Arg Lys Val Pro Val Val Cys Thr Leu Leu Glu Gly Gly Ile
            340                 345                 350

Ser Ser Ile Asn Ala Ile His Asp Tyr Val Thr Met Lys Pro Asp Ile
        355                 360                 365

Pro Ala Ile Val Cys Asp Gly Ser Gly Arg Ala Ala Asp Ile Ile Ser
370                 375                 380

Phe Ala Ala Arg Tyr Ile Asn Ser Asp Gly Thr Phe Ala Ala Glu Val
385                 390                 395                 400

Gly Glu Lys Leu Arg Asn Leu Ile Lys Met Val Phe Pro Glu Thr Asp
                405                 410                 415

Gln Glu Glu Met Phe Arg Lys Ile Thr Glu Cys Val Ile Arg Asp Asp
            420                 425                 430

Leu Leu Arg Ile Phe Arg Tyr Gly Gln Glu Glu Glu Asp Val Asp
        435                 440                 445

Phe Val Ile Leu Ser Thr Val Leu Gln Lys Gln Asn Leu Pro Pro Asp
450                 455                 460

Glu Gln Leu Ala Leu Thr Leu Ser Trp Asn Arg Val Asp Leu Ala Lys
465                 470                 475                 480

Ser Cys Leu Phe Ser Asn Gly Arg Lys Trp Ser Ser Asp Val Leu Glu
                485                 490                 495

Lys Ala Met Asn Asp Ala Leu Tyr Trp Asp Arg Val Asp Phe Val Glu
            500                 505                 510

Cys Leu Leu Glu Asn Gly Val Ser Met Lys Asn Phe Leu Ser Ile Asn
        515                 520                 525

Arg Leu Glu Asn Leu Tyr Asn Met Asp Asp Ile Asn Ser Ala His Ser
530                 535                 540

Val Arg Asn Trp Met Glu Asn Phe Asp Ser Met Asp Pro His Thr Tyr
545                 550                 555                 560

Leu Thr Ile Pro Met Ile Gly Gln Val Val Glu Lys Leu Met Gly Asn
```

-continued

```
                565                 570                 575
Ala Phe Gln Leu Tyr Tyr Thr Ser Arg Ser Phe Lys Gly Lys Tyr Asp
            580                 585                 590

Arg Tyr Lys Arg Ile Asn Gln Ser Ser Tyr Phe His Arg Lys Arg Lys
        595                 600                 605

Ile Val Gln Lys Glu Leu Phe Lys Lys Ser Asp Asp Gln Ile Asn
    610                 615                 620

Asp Asn Glu Glu Glu Asp Phe Ser Phe Ala Tyr Pro Phe Asn Asp Leu
625                 630                 635                 640

Leu Ile Trp Ala Val Leu Thr Ser Arg His Gly Met Ala Glu Cys Met
                645                 650                 655

Trp Val His Gly Glu Asp Ala Met Ala Lys Cys Leu Leu Ala Ile Arg
            660                 665                 670

Leu Tyr Lys Ala Thr Ala Lys Ile Ala Glu Asp Glu Tyr Leu Asp Val
        675                 680                 685

Glu Glu Ala Lys Arg Leu Phe Asp Asn Ala Val Lys Cys Arg Glu Asp
    690                 695                 700

Ala Ile Glu Leu Leu Asp Gln Cys Tyr Arg Ala Asp His Asp Arg Thr
705                 710                 715                 720

Leu Arg Leu Leu Arg Met Glu Leu Pro His Trp Gly Asn Asn Asn Cys
                725                 730                 735

Leu Ser Leu Ala Val Leu Ala Asn Thr Lys Thr Phe Leu Ala His Pro
            740                 745                 750

Cys Cys Gln Ile Leu Leu Ala Glu Leu Trp His Gly Ser Leu Lys Val
        755                 760                 765

Arg Ser Gly Ser Asn Val Arg Val Leu Thr Ala Leu Ile Cys Pro Pro
    770                 775                 780

Ala Ile Leu Phe Met Ala Tyr Lys Pro Lys His Ser Lys Thr Ala Arg
785                 790                 795                 800

Leu Leu Ser Glu Glu Thr Pro Glu Gln Leu Pro Tyr Pro Arg Glu Ser
                805                 810                 815

Ile Thr Ser Thr Thr Ser Asn Arg Tyr Arg Tyr Ser Lys Gly Pro Glu
            820                 825                 830

Glu Gln Lys Glu Thr Leu Leu Glu Lys Gly Ser Tyr Thr Lys Lys Val
        835                 840                 845

Thr Ile Ile Ser Ser Arg Lys Asn Ser Gly Val Ala Ser Val Tyr Gly
    850                 855                 860

Ser Ala Ser Ser Met Met Phe Lys Arg Glu Pro Gln Leu Asn Lys Phe
865                 870                 875                 880

Glu Arg Phe Arg Ala Phe Tyr Ser Ser Pro Ile Thr Lys Phe Trp Ser
                885                 890                 895

Trp Cys Ile Ala Phe Leu Ile Phe Leu Thr Thr Gln Thr Cys Ile Leu
            900                 905                 910

Leu Leu Glu Thr Ser Leu Lys Pro Ser Lys Tyr Glu Trp Ile Thr Phe
        915                 920                 925

Ile Tyr Thr Val Thr Leu Ser Val Glu His Ile Arg Lys Leu Met Thr
    930                 935                 940

Ser Glu Gly Ser Arg Ile Asn Glu Lys Val Lys Val Phe Tyr Ala Lys
945                 950                 955                 960

Trp Tyr Asn Ile Trp Thr Ser Ala Ala Leu Leu Phe Phe Leu Val Gly
                965                 970                 975

Tyr Gly Phe Arg Leu Val Pro Met Tyr Arg His Ser Trp Gly Arg Val
            980                 985                 990
```

-continued

```
Leu Leu Ser Phe Ser Asn Val Leu Phe Tyr Met Lys Ile Phe Glu Tyr
        995                 1000                1005

Leu Ser Val His Pro Leu Leu Gly Pro Tyr Ile Gln Met Ala Ala
    1010            1015                1020

Lys Met Val Trp Ser Met Cys Tyr Ile Cys Val Leu Leu Leu Val
    1025            1030                1035

Pro Leu Met Ala Phe Gly Val Asn Arg Gln Ala Leu Thr Glu Pro
    1040            1045                1050

Asn Val Lys Asp Trp His Trp Leu Leu Val Arg Asn Ile Phe Tyr
    1055            1060                1065

Lys Pro Tyr Phe Met Leu Tyr Gly Glu Val Tyr Ala Gly Glu Ile
    1070            1075                1080

Asp Thr Cys Gly Asp Glu Gly Ile Arg Cys Phe Pro Gly Tyr Phe
    1085            1090                1095

Ile Pro Pro Leu Leu Met Val Ile Phe Leu Leu Val Ala Asn Ile
    1100            1105                1110

Leu Leu Leu Asn Leu Leu Ile Ala Ile Phe Asn Asn Ile Tyr Asn
    1115            1120                1125

Asp Ser Ile Glu Lys Ser Lys Glu Ile Trp Leu Phe Gln Arg Tyr
    1130            1135                1140

Gln Gln Leu Met Glu Tyr His Asp Ser Pro Phe Leu Pro Pro Pro
    1145            1150                1155

Phe Ser Ile Phe Ala His Val Tyr His Phe Ile Asp Tyr Leu Tyr
    1160            1165                1170

Asn Leu Arg Arg Pro Asp Thr Lys Arg Phe Arg Ser Glu His Ser
    1175            1180                1185

Ile Lys Leu Ser Val Thr Glu Asp Glu Met Lys Arg Ile Gln Asp
    1190            1195                1200

Phe Glu Glu Asp Cys Ile Asp Thr Leu Thr Arg Ile Arg Lys Leu
    1205            1210                1215

Lys Leu Asn Thr Lys Glu Pro Leu Ser Val Thr Asp Leu Thr Glu
    1220            1225                1230

Leu Thr Cys Gln Arg Val His Asp Leu Met Gln Glu Asn Phe Leu
    1235            1240                1245

Leu Lys Ser Arg Val Tyr Asp Ile Glu Thr Lys Ile Asp His Ile
    1250            1255                1260

Ser Asn Ser Ser Asp Glu Val Val Gln Ile Leu Lys Asn Lys Lys
    1265            1270                1275

Leu Ser Gln Asn Phe Ala Ala Ser Ser Leu Ser Leu Pro Asp Thr
    1280            1285                1290

Ser Ile Glu Val Pro Lys Ile Thr Lys Thr Leu Ile Asp Cys His
    1295            1300                1305

Leu Ser Pro Val Ser Ile Glu Asp Arg Leu Ala Thr Arg Ser Pro
    1310            1315                1320

Leu Leu Ala Asn Leu Gln Arg Asp His Thr Leu Arg Lys Leu Pro
    1325            1330                1335

Thr Trp Glu Thr Ser Thr Ala Ser Thr Ser Ser Phe Glu Phe Val
    1340            1345                1350

Phe Tyr Phe Thr Arg His Glu Gly Asn Glu Asn Lys Tyr Glu Phe
    1355            1360                1365

Lys Lys Leu Glu Lys Gly Gly Phe Trp Arg Asn Asn Tyr Val Ile
    1370            1375                1380
```

```
Ser Trp Arg Leu
        1385

<210> SEQ ID NO 15
<211> LENGTH: 1868
<212> TYPE: PRT
<213> ORGANISM: Caenorhabditis elegans

<400> SEQUENCE: 15

Met Asn Leu Cys Tyr Arg Arg His Arg Tyr Ala Ser Ser Pro Glu Val
1               5                   10                  15

Trp Cys Thr Met Glu Ser Asp Glu Leu Gly Val Thr Arg Tyr Leu Gln
            20                  25                  30

Ser Lys Gly Gly Asp Gln Val Pro Pro Thr Ser Thr Thr Thr Gly Gly
        35                  40                  45

Ala Gly Gly Asp Gly Asn Ala Val Pro Thr Thr Ser Gln Ala Gln Ala
    50                  55                  60

Gln Thr Phe Asn Ser Gly Arg Gln Thr Thr Gly Met Ser Ser Gly Asp
65                  70                  75                  80

Arg Leu Asn Glu Asp Val Ser Ala Thr Ala Asn Ser Ala Gln Leu Val
                85                  90                  95

Leu Pro Thr Pro Leu Phe Asn Gln Met Arg Phe Thr Glu Ser Asn Met
            100                 105                 110

Ser Leu Asn Arg His Asn Trp Val Arg Glu Thr Phe Thr Arg Arg Glu
        115                 120                 125

Cys Ser Arg Phe Ile Ala Ser Ser Arg Asp Leu His Lys Cys Gly Cys
    130                 135                 140

Gly Arg Thr Arg Asp Ala His Arg Asn Ile Pro Glu Leu Thr Ser Glu
145                 150                 155                 160

Phe Leu Arg Gln Lys Arg Ser Val Ala Ala Leu Glu Gln Gln Arg Ser
                165                 170                 175

Ile Ser Asn Val Asn Asp Asp Ile Asn Thr Gln Asn Met Tyr Thr Lys
            180                 185                 190

Arg Gly Ala Asn Glu Lys Trp Ser Leu Arg Lys His Thr Val Ser Leu
        195                 200                 205

Ala Thr Asn Ala Phe Gly Gln Val Glu Phe Gln Gly Gly Pro His Pro
    210                 215                 220

Tyr Lys Ala Gln Tyr Val Arg Val Asn Phe Asp Thr Glu Pro Ala Tyr
225                 230                 235                 240

Ile Met Ser Leu Phe Glu His Val Trp Gln Ile Ser Pro Pro Arg Leu
                245                 250                 255

Ile Ile Thr Val His Gly Gly Thr Ser Asn Phe Asp Leu Gln Pro Lys
            260                 265                 270

Leu Ala Arg Val Phe Arg Lys Gly Leu Leu Lys Ala Ala Ser Thr Thr
        275                 280                 285

Gly Ala Trp Ile Ile Thr Ser Gly Cys Asp Thr Gly Val Val Lys His
    290                 295                 300

Val Ala Ala Ala Leu Glu Gly Ala Gln Ser Ala Gln Arg Asn Lys Ile
305                 310                 315                 320

Val Cys Ile Gly Ile Ala Pro Trp Gly Leu Leu Lys Lys Arg Glu Asp
                325                 330                 335

Phe Ile Gly Gln Asp Lys Thr Val Pro Tyr Tyr Pro Ser Ser Ser Lys
            340                 345                 350

Gly Arg Phe Thr Gly Leu Asn Asn Arg His Ser Tyr Phe Leu Leu Val
        355                 360                 365
```

```
Asp Asn Gly Thr Val Gly Arg Tyr Gly Ala Glu Val Ile Leu Arg Lys
    370                 375                 380

Arg Leu Glu Met Tyr Ile Ser Gln Lys Gln Lys Ile Phe Gly Gly Thr
385                 390                 395                 400

Arg Ser Val Pro Val Val Cys Val Val Leu Glu Gly Gly Ser Cys Thr
                405                 410                 415

Ile Arg Ser Val Leu Asp Tyr Val Thr Asn Val Pro Arg Val Pro Val
            420                 425                 430

Val Val Cys Asp Gly Ser Gly Arg Ala Ala Asp Leu Leu Ala Phe Ala
        435                 440                 445

His Gln Asn Val Thr Glu Asp Gly Leu Leu Pro Asp Asp Ile Arg Arg
    450                 455                 460

Gln Val Leu Leu Leu Val Glu Thr Thr Phe Gly Cys Ser Glu Ala Ala
465                 470                 475                 480

Ala His Arg Leu Leu His Glu Leu Thr Val Cys Ala Gln His Lys Asn
                485                 490                 495

Leu Leu Thr Ile Phe Arg Leu Gly Glu Gln Gly Glu His Asp Val Asp
            500                 505                 510

His Ala Ile Leu Thr Ala Leu Leu Lys Gly Gln Asn Leu Ser Ala Ala
        515                 520                 525

Asp Gln Leu Ala Leu Ala Leu Ala Trp Asn Arg Val Asp Ile Ala Arg
    530                 535                 540

Ser Asp Val Phe Ala Met Gly His Glu Trp Pro Gln Ala Ala Leu His
545                 550                 555                 560

Asn Ala Met Met Glu Ala Leu Ile His Asp Arg Val Asp Phe Val Arg
                565                 570                 575

Leu Leu Leu Glu Gln Gly Ile Asn Met Gln Lys Phe Leu Thr Ile Ser
            580                 585                 590

Arg Leu Asp Glu Leu Tyr Asn Thr Asp Lys Gly Pro Pro Asn Thr Leu
        595                 600                 605

Phe Tyr Ile Val Arg Asp Val Val Arg Val Arg Gln Gly Tyr Arg Phe
    610                 615                 620

Lys Leu Pro Asp Ile Gly Leu Val Ile Glu Lys Leu Met Gly Asn Ser
625                 630                 635                 640

Tyr Gln Cys Ser Tyr Thr Thr Ser Glu Phe Arg Asp Lys Tyr Lys Gln
                645                 650                 655

Arg Met Lys Arg Val Lys His Ala Gln Lys Lys Ala Met Gly Val Phe
            660                 665                 670

Ser Ser Arg Pro Ser Arg Thr Gly Ser Gly Ile Ala Ser Arg Gln Ser
        675                 680                 685

Thr Glu Gly Met Gly Gly Val Gly Gly Ser Ser Val Ala Gly Val
    690                 695                 700

Phe Gly Asn Ser Phe Gly Asn Gln Asp Pro Leu Asp Pro His Val
705                 710                 715                 720

Asn Arg Ser Ala Leu Ser Gly Ser Arg Ala Leu Ser Asn His Ile Leu
                725                 730                 735

Trp Arg Ser Ala Phe Arg Gly Asn Phe Pro Ala Asn Pro Met Arg Pro
            740                 745                 750

Pro Asn Leu Gly Asp Ser Arg Asp Cys Gly Ser Glu Phe Asp Glu Glu
        755                 760                 765

Leu Ser Leu Thr Ser Ala Ser Asp Gly Ser Gln Thr Glu Pro Asp Phe
    770                 775                 780
```

-continued

```
Arg Tyr Pro Tyr Ser Glu Leu Met Ile Trp Ala Val Leu Thr Lys Arg
785                 790                 795                 800

Gln Asp Met Ala Met Cys Met Trp Gln His Gly Glu Glu Ala Met Ala
                805                 810                 815

Lys Ala Leu Val Ala Cys Arg Leu Tyr Lys Ser Leu Ala Thr Glu Ala
                820                 825                 830

Ala Glu Asp Tyr Leu Glu Val Glu Ile Cys Glu Glu Leu Lys Lys Tyr
            835                 840                 845

Ala Glu Glu Phe Arg Ile Leu Ser Leu Glu Leu Leu Asp His Cys Tyr
        850                 855                 860

His Val Asp Asp Ala Gln Thr Leu Gln Leu Leu Thr Tyr Glu Leu Ser
865                 870                 875                 880

Asn Trp Ser Asn Glu Thr Cys Leu Ala Leu Ala Val Ile Val Asn Asn
                885                 890                 895

Lys His Phe Leu Ala His Pro Cys Cys Gln Ile Leu Leu Ala Asp Leu
                900                 905                 910

Trp His Gly Gly Leu Arg Met Arg Thr His Ser Asn Ile Lys Val Val
            915                 920                 925

Leu Gly Leu Ile Cys Pro Pro Phe Ile Gln Met Leu Glu Phe Lys Thr
        930                 935                 940

Arg Glu Glu Leu Leu Asn Gln Pro Gln Thr Ala Ala Glu His Gln Asn
945                 950                 955                 960

Asp Met Asn Tyr Ser Ser Ser Ser Ser Ser Ser Ser Ser Ser Ser Ser
                965                 970                 975

Ser Ser Ser Ser Ser Asp Ser Ser Ser Phe Glu Asp Asp Asp Asp Glu
                980                 985                 990

Asn Asn Ala His Asn His Asp Gln  Lys Arg Thr Arg Lys  Thr Ser Gln
            995                 1000                1005

Gly Ser  Ala Gln Ser Leu Asn  Ile Thr Ser Leu Phe  His Ser Arg
        1010                1015                1020

Arg Arg  Lys Ala Lys Lys Asn  Glu Lys Cys Asp Arg  Glu Thr Asp
        1025                1030                1035

Ala Ser  Ala Cys Glu Ala Gly  Asn Arg Gln Ile Gln  Asn Gly Gly
        1040                1045                1050

Leu Thr  Ala Glu Tyr Gly Thr  Phe Gly Glu Ser Asn  Gly Val Ser
        1055                1060                1065

Pro Pro  Pro Pro Tyr Met Arg  Ala Asn Ser Arg Ser  Arg Tyr Asn
        1070                1075                1080

Asn Arg  Ser Asp Met Ser Lys  Thr Ser Ser Val Ile  Phe Gly Ser
        1085                1090                1095

Asp Pro  Asn Leu Ser Lys Leu  Gln Lys Ser Asn Ile  Thr Ser Thr
        1100                1105                1110

Asp Arg  Pro Asn Pro Met Glu  Gln Phe Gln Gly Thr  Arg Lys Ile
        1115                1120                1125

Lys Met  Arg Arg Arg Phe Tyr  Glu Phe Tyr Ser Ala  Pro Ile Ser
        1130                1135                1140

Thr Phe  Trp Ser Trp Thr Ile  Ser Phe Ile Leu Phe  Ile Thr Phe
        1145                1150                1155

Phe Thr  Tyr Thr Leu Leu Val  Lys Thr Pro Pro Arg  Pro Thr Val
        1160                1165                1170

Ile Glu  Tyr Ile Leu Ile Ala  Tyr Val Ala Ala Phe  Gly Leu Glu
        1175                1180                1185

Gln Val  Arg Lys Ile Ile Met  Ser Asp Ala Lys Pro  Phe Tyr Glu
```

|     |     |     |     |     |     |     |     |     |     |
| --- | --- | --- | --- | --- | --- | --- | --- | --- | --- |
|     | 1190 |     |     |     | 1195 |     |     |     | 1200 |
| Lys | Ile | Arg | Thr | Tyr | Val | Cys | Ser | Phe | Trp | Asn | Cys | Val | Thr | Ile |
|     | 1205 |     |     |     | 1210 |     |     |     | 1215 |
| Leu | Ala | Ile | Ile | Phe | Tyr | Ile | Val | Gly | Phe | Phe | Met | Arg | Cys | Phe |
|     | 1220 |     |     |     | 1225 |     |     |     | 1230 |
| Gly | Ser | Val | Ala | Tyr | Gly | Arg | Val | Ile | Leu | Ala | Cys | Asp | Ser | Val |
|     | 1235 |     |     |     | 1240 |     |     |     | 1245 |
| Leu | Trp | Thr | Met | Lys | Leu | Leu | Asp | Tyr | Met | Ser | Val | His | Pro | Lys |
|     | 1250 |     |     |     | 1255 |     |     |     | 1260 |
| Leu | Gly | Pro | Tyr | Val | Thr | Met | Ala | Gly | Lys | Met | Ile | Gln | Asn | Met |
|     | 1265 |     |     |     | 1270 |     |     |     | 1275 |
| Ser | Tyr | Ile | Ile | Val | Met | Leu | Val | Val | Thr | Leu | Leu | Ser | Phe | Gly |
|     | 1280 |     |     |     | 1285 |     |     |     | 1290 |
| Leu | Ala | Arg | Gln | Ser | Ile | Thr | Tyr | Pro | Asp | Glu | Thr | Trp | His | Trp |
|     | 1295 |     |     |     | 1300 |     |     |     | 1305 |
| Ile | Leu | Val | Arg | Asn | Ile | Phe | Leu | Lys | Pro | Tyr | Phe | Met | Leu | Tyr |
|     | 1310 |     |     |     | 1315 |     |     |     | 1320 |
| Gly | Glu | Val | Tyr | Ala | Asp | Glu | Ile | Asp | Thr | Cys | Gly | Asp | Glu | Ala |
|     | 1325 |     |     |     | 1330 |     |     |     | 1335 |
| Trp | Asp | Gln | His | Leu | Glu | Asn | Gly | Gly | Pro | Val | Ile | Leu | Gly | Asn |
|     | 1340 |     |     |     | 1345 |     |     |     | 1350 |
| Gly | Thr | Thr | Gly | Leu | Ser | Cys | Val | Pro | Gly | Tyr | Trp | Ile | Pro | Pro |
|     | 1355 |     |     |     | 1360 |     |     |     | 1365 |
| Leu | Leu | Met | Thr | Phe | Phe | Leu | Leu | Ile | Ala | Asn | Ile | Leu | Leu | Met |
|     | 1370 |     |     |     | 1375 |     |     |     | 1380 |
| Ser | Met | Leu | Ile | Ala | Ile | Phe | Asn | His | Ile | Phe | Asp | Ala | Thr | Asp |
|     | 1385 |     |     |     | 1390 |     |     |     | 1395 |
| Glu | Met | Ser | Gln | Gln | Ile | Trp | Leu | Phe | Gln | Arg | Tyr | Lys | Gln | Val |
|     | 1400 |     |     |     | 1405 |     |     |     | 1410 |
| Met | Glu | Tyr | Glu | Ser | Thr | Pro | Phe | Leu | Pro | Pro | Pro | Leu | Thr | Pro |
|     | 1415 |     |     |     | 1420 |     |     |     | 1425 |
| Leu | Tyr | His | Gly | Val | Leu | Ile | Leu | Gln | Phe | Val | Arg | Thr | Arg | Leu |
|     | 1430 |     |     |     | 1435 |     |     |     | 1440 |
| Ser | Cys | Ser | Lys | Ser | Gln | Glu | Arg | Asn | Pro | Ile | Leu | Leu | Leu | Lys |
|     | 1445 |     |     |     | 1450 |     |     |     | 1455 |
| Ile | Ala | Glu | Leu | Phe | Leu | Asp | Asn | Asp | Gln | Ile | Glu | Lys | Leu | His |
|     | 1460 |     |     |     | 1465 |     |     |     | 1470 |
| Asp | Phe | Glu | Glu | Asp | Cys | Met | Glu | Asp | Leu | Ala | Arg | Gln | Lys | Leu |
|     | 1475 |     |     |     | 1480 |     |     |     | 1485 |
| Asn | Glu | Lys | Asn | Thr | Ser | Asn | Glu | Gln | Arg | Ile | Leu | Arg | Ala | Asp |
|     | 1490 |     |     |     | 1495 |     |     |     | 1500 |
| Ile | Arg | Thr | Asp | Gln | Ile | Leu | Asn | Arg | Leu | Ile | Asp | Leu | Gln | Ala |
|     | 1505 |     |     |     | 1510 |     |     |     | 1515 |
| Lys | Glu | Ser | Met | Gly | Arg | Asp | Val | Ile | Asn | Asp | Val | Glu | Ser | Arg |
|     | 1520 |     |     |     | 1525 |     |     |     | 1530 |
| Leu | Ala | Ser | Val | Glu | Lys | Ala | Gln | Asn | Glu | Ile | Leu | Glu | Cys | Val |
|     | 1535 |     |     |     | 1540 |     |     |     | 1545 |
| Arg | Ala | Leu | Leu | Asn | Gln | Asn | Asn | Ala | Pro | Thr | Ala | Ile | Gly | Arg |
|     | 1550 |     |     |     | 1555 |     |     |     | 1560 |
| Cys | Phe | Ser | Pro | Ser | Pro | Asp | Pro | Leu | Val | Glu | Thr | Ala | Asn | Gly |
|     | 1565 |     |     |     | 1570 |     |     |     | 1575 |
| Thr | Pro | Gly | Pro | Leu | Leu | Leu | Lys | Leu | Pro | Gly | Thr | Asp | Pro | Ile |
|     | 1580 |     |     |     | 1585 |     |     |     | 1590 |

| | | | | | | | | | | | |
|---|---|---|---|---|---|---|---|---|---|---|---|
|Leu|Glu|Glu|Lys|Asp|His|Asp|Ser|Gly|Glu|Asn|Ser|Asn|Ser|Leu|
| |1595| | | |1600| | | |1605| | |

Leu Glu Glu Lys Asp His Asp Ser Gly Glu Asn Ser Asn Ser Leu
    1595                1600                1605

Pro Pro Gly Arg Ile Arg Arg Asn Arg Thr Ala Thr Ile Cys Gly
    1610                1615                1620

Gly Tyr Val Ser Glu Glu Arg Asn Met Met Leu Leu Ser Pro Lys
    1625                1630                1635

Pro Ser Asp Val Ser Gly Ile Pro Gln Gln Arg Leu Met Ser Val
    1640                1645                1650

Thr Ser Met Asp Pro Leu Pro Leu Pro Leu Ala Lys Leu Ser Thr
    1655                1660                1665

Met Ser Ile Arg Arg Arg His Glu Glu Tyr Thr Ser Ile Thr Asp
    1670                1675                1680

Ser Ile Ala Ile Arg His Pro Glu Arg Arg Ile Arg Asn Asn Arg
    1685                1690                1695

Ser Asn Ser Ser Glu His Asp Glu Ser Ala Val Asp Ser Glu Gly
    1700                1705                1710

Gly Gly Asn Val Thr Ser Ser Pro Arg Lys Arg Ser Thr Arg Asp
    1715                1720                1725

Leu Arg Met Thr Pro Ser Ser Gln Val Glu Glu Ser Thr Ser Arg
    1730                1735                1740

Asp Gln Ile Phe Glu Ile Asp His Pro Glu His Glu Glu Asp Glu
    1745                1750                1755

Ala Gln Ala Asp Cys Glu Leu Thr Asp Val Ile Thr Glu Glu Glu
    1760                1765                1770

Asp Glu Glu Glu Asp Asp Glu Glu Asp Ser His Glu Arg His
    1775                1780                1785

His Ile His Pro Arg Arg Lys Ser Ser Arg Gln Asn Arg Gln Pro
    1790                1795                1800

Ser His Thr Leu Glu Thr Asp Leu Ser Glu Gly Glu Glu Val Asp
    1805                1810                1815

Pro Leu Asp Val Leu Lys Met Lys Glu Leu Pro Ile Ile His Gln
    1820                1825                1830

Ile Leu Asn Glu Glu Glu Gln Ala Gly Ala Pro His Ser Thr Pro
    1835                1840                1845

Val Ile Ala Ser Pro Ser Ser Ser Arg Ala Asp Leu Thr Ser Gln
    1850                1855                1860

Lys Cys Ser Asp Val
    1865

<210> SEQ ID NO 16
<211> LENGTH: 489
<212> TYPE: DNA
<213> ORGANISM: Mus musculus

<400> SEQUENCE: 16
ccctgaaaga ctcgacttct gctgctagcg ctggagctga gttagttttg agaaggtttc      60
ccggggctgt ccttgttcgg tggcccgtgc caccgcctcc ggagacgctt tccgatagat     120
ggctgcaggc cgcggaggtg gaggaggagc cgctgcccct tccggagtccg ccccgtgagg    180
agaatgtccc agaaatcctg gatagagagc actttgacca agagggagtg tgtatatatt     240
ataccaagct ccaaagaccc tcacagatgt cttccaggat gtcagatttg tcagcaactt     300
gtcagatgtt tctgtggtcg tttggtcaag caacatgcat gctttactgc aagtcttgcc     360
atgaaatact cagatgtgaa attgggtgaa cactttaacc aggcaataga agaatggtct     420

```
gtggaaaagc acacggagca gagcccaaca gatgcttatg gagtcatcaa ttttcaaggg    480
ggttctcat                                                            489
```

<210> SEQ ID NO 17
<211> LENGTH: 102
<212> TYPE: PRT
<213> ORGANISM: Mus musculus

<400> SEQUENCE: 17

```
Met Ser Gln Lys Ser Trp Ile Glu Ser Thr Leu Thr Lys Arg Glu Cys
1               5                   10                  15

Val Tyr Ile Ile Pro Ser Ser Lys Asp Pro His Arg Cys Leu Pro Gly
                20                  25                  30

Cys Gln Ile Cys Gln Gln Leu Val Arg Cys Phe Cys Gly Arg Leu Val
            35                  40                  45

Lys Gln His Ala Cys Phe Thr Ala Ser Leu Ala Met Lys Tyr Ser Asp
    50                  55                  60

Val Lys Leu Gly Glu His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95

Phe Gln Gly Gly Ser His
            100
```

<210> SEQ ID NO 18
<211> LENGTH: 410
<212> TYPE: DNA
<213> ORGANISM: Homo sapiens
<220> FEATURE:
<221> NAME/KEY: Unsure
<222> LOCATION: (6)..(6)
<223> OTHER INFORMATION: a, or c, or g, or t
<220> FEATURE:
<221> NAME/KEY: Unsure
<222> LOCATION: (58)..(58)
<223> OTHER INFORMATION: a, or c, or g, or t
<220> FEATURE:
<221> NAME/KEY: Unsure
<222> LOCATION: (89)..(89)
<223> OTHER INFORMATION: a, or c, or g, or t
<220> FEATURE:
<221> NAME/KEY: Unsure
<222> LOCATION: (406)..(406)
<223> OTHER INFORMATION: a, or c, or g, or t

<400> SEQUENCE: 18

```
gccgcnggag cctgagcgga gggtgtgcgc agcctcgcca gcgggggccc cgggctgngc    60
cattgcctca ctgagccagc gcctgcctnc tacctcgccg acagctggaa ccagtgcgac    120
ctagtggctc tcacctgctt cctcctgggc gtgggctgcc ggctgacccc gggtttgtac    180
cacctgggcc gcactgtcct ctgcatcgac ttcatggttt tcacggtgcg gctgcttcac    240
atcttcacgg tcaacaaaca gctggggccc aagatcgtca tcgtgagcaa gatgatgaag    300
gacgtgttct tcttcctctt cttcctcggc gtgtggctgg tagctatggg ttgggccacg    360 gagggggttcc tgaggccacg ggacagtgac ttcccaagta tcctgncgcc               410
```

<210> SEQ ID NO 19
<211> LENGTH: 131
<212> TYPE: PRT
<213> ORGANISM: Homo sapiens
<220> FEATURE:
<221> NAME/KEY: UNSURE

```
<222> LOCATION: (15)..(15)
<223> OTHER INFORMATION: any amino acid
<220> FEATURE:
<221> NAME/KEY: UNSURE
<222> LOCATION: (25)..(25)
<223> OTHER INFORMATION: any amino acid
<220> FEATURE:
<221> NAME/KEY: UNSURE
<222> LOCATION: (131)..(131)
<223> OTHER INFORMATION: any amino acid

<400> SEQUENCE: 19

Ala Glu Gly Val Arg Ser Leu Ala Ser Gly Gly Pro Gly Leu Xaa His
1               5                   10                  15

Cys Leu Thr Glu Pro Ala Pro Ala Xaa Tyr Leu Ala Asp Ser Trp Asn
            20                  25                  30

Gln Cys Asp Leu Val Ala Leu Thr Cys Phe Leu Leu Gly Val Gly Cys
        35                  40                  45

Arg Leu Thr Pro Gly Leu Tyr His Leu Gly Arg Thr Val Leu Cys Ile
    50                  55                  60

Asp Phe Met Val Phe Thr Val Arg Leu Leu His Ile Phe Thr Val Asn
65                  70                  75                  80

Lys Gln Leu Gly Pro Lys Ile Val Val Ser Lys Met Met Lys Asp
                85                  90                  95

Val Phe Phe Leu Phe Leu Gly Val Trp Leu Val Ala Met Gly
                100                 105                 110

Trp Ala Thr Glu Gly Phe Leu Arg Pro Arg Asp Ser Asp Phe Pro Ser
            115                 120                 125

Ile Leu Xaa
    130

<210> SEQ ID NO 20
<211> LENGTH: 389
<212> TYPE: DNA
<213> ORGANISM: Homo sapiens

<400> SEQUENCE: 20 caaattttt  gttagtacac  catctcatcc  aaattgcaaa  agtcacatgg  aaactggaac      60
caaagatcaa  gaaactgttt  gctctaaagc  tacagaagga  gataatacag  aatttggagc     120
atttgtagga  cacagagata  gcatggattt  acagaggttt  aaagaaacat  caaacaagat     180
aaaaatacta  tccaataaca  atacttctga  aaacactttg  aaacgagtga  gttctcttgc     240
tggatttact  gactgtcaca  gaacttccat  tcctgttcat  tcaaaacgag  aaaagatcag     300
tagaaggcca  tctaccgaag  acactcatga  agtagattcc  aaagcagctt  taataccggt     360
ttgtagattt  caactaaaca  gatatatat                                          389

<210> SEQ ID NO 21
<211> LENGTH: 415
<212> TYPE: DNA
<213> ORGANISM: Homo sapiens

<400> SEQUENCE: 21
atttctagtt  tttcaaattt  gccagtcttt  ttgaatagta  tctccttctt  ttctcatgtt      60
ttatatttaa  aactttttta  tgtccatcat  cactttaaac  atacttattt  tgtcatctat     120
aaccaataat  tccactatct  tatcagaaat  caaataccgt  ttatgtaagt  tgactcccat     180
gagttctaaa  ttgccattgt  gaggtcatct  tcggttaggc  tttaatttgt  tgcaaagttg     240
tgcagctcag  ggtcaggaag  agtccctcca  gaaaggagga  tttgttactg  tgaatctctt     300
```

```
tgttaactaa cctctttccc cactgaaata acttttttca ataacatgat tttaacaaca    360
taatctctct atgccagaac agatatatat gaatgtaagt caatattttc ttgag         415

<210> SEQ ID NO 22
<211> LENGTH: 405
<212> TYPE: DNA
<213> ORGANISM: Mus musculus

<400> SEQUENCE: 22
ttattatggc ttatcatgaa aaaccagtcc tgcctcctcc tcttatcatc ctcagccata     60
tagtttcact gttttgctgt gtatgcaaaa gaagaaagaa agataagact tccgatgggc    120
caaaactttt cttaacagaa gaagatcaaa agaaactcca tgattttgaa gagcagtgtg    180
ttgagatgta ctttgatgag aaagatgaca aattcaattc tgggagtgaa gagagaatcc    240
gggtcacttt tgaaagagtg gagcagatga gcattcagat taaagaagtt ggagatcgtg    300
tcaactacat aaaaagatca ttacagtctt tagattctca aattggtcat ctgcaagatc    360
tctcagccct aacagtagat acattgaaaa cacttacagc ccaga                    405

<210> SEQ ID NO 23
<211> LENGTH: 5117
<212> TYPE: DNA
<213> ORGANISM: Homo sapiens
<220> FEATURE:
<221> NAME/KEY: Unsure
<222> LOCATION: (2382)..(2382)
<223> OTHER INFORMATION: a, or c, or g, or t
<220> FEATURE:
<221> NAME/KEY: Unsure
<222> LOCATION: (4664)..(4664)
<223> OTHER INFORMATION: a, or c, or g, or t
<220> FEATURE:
<221> NAME/KEY: Unsure
<222> LOCATION: (4682)..(4682)
<223> OTHER INFORMATION: a, or c, or g, or t
<220> FEATURE:
<221> NAME/KEY: Unsure
<222> LOCATION: (4702)..(4702)
<223> OTHER INFORMATION: a, or c, or g, or t
<220> FEATURE:
<221> NAME/KEY: Unsure
<222> LOCATION: (5038)..(5039)
<223> OTHER INFORMATION: a, or c, or g, or t
<220> FEATURE:
<221> NAME/KEY: Unsure
<222> LOCATION: (5056)..(5056)
<223> OTHER INFORMATION: a, or c, or g, or t
<220> FEATURE:
<221> NAME/KEY: Unsure
<222> LOCATION: (5071)..(5072)
<223> OTHER INFORMATION: a, or c, or g, or t

<400> SEQUENCE: 23
gatggcaaca tggtgaagaa tcaatggcta aagcattagt tgcctgtaag atctatcgtt     60
caatggcata tgaagcaaag cagagtgacc tggtagatga tacttcagaa gaactaaaac    120
agtattccaa tgattttggt cagttggccg ttgaattatt agaacagtcc ttcagacaag    180
atgaaaccat ggctatgaaa ttgctcactt atgaactgaa gaactggagt aattcaacct    240
gccttaagtt agcagtttct tcaagactta gacctttgt agctcacacc tgtacacaaa    300
tgttgttatc tgatatgtgg atgggaaggc tgaatatgag gaaaaattcc tggtacaagg    360
tcatactaag cattttagtt ccacctgcca tattgctgtt agagtataaa actaaggctg    420
aaatgtccca tatcccacaa tctcaagatg ctcatcagat gacaatggat gacagcgaaa    480
```

| | |
|---|---|
| acaactttca gaacataaca gaagagatcc ccatggaagt gtttaaagaa gtacggattt | 540 |
| tggatagtaa tgaaggaaag aatgagatgg agatacaaat gaaatcaaaa aagcttccaa | 600 |
| ttacgcgaaa gttttatgcc ttttatcatg caccaattgt aaaattctgg tttaacacgt | 660 |
| tggcatattt aggatttctg atgctttata catttgtggt tcttgtacaa atggaacagt | 720 |
| taccttcagt tcaagaatgg attgttattg cttatatttt tacttatgcc attgagaaag | 780 |
| tccgtgagat ctttatgtct gaagctggga agtaaaccaa gagattaaa gtatggttta | 840 |
| gtgattactt caacatcagt gatacaattg ccataatttc tttcttcatt ggatttggac | 900 |
| taagatttgg agcaaaatgg aactttgcaa atgcatatga taatcatgtt tttgtggctg | 960 |
| gaagattaat ttactgtctt aacataaatat tttggtatgt gcgtttgcta gattttctag | 1020 |
| ctgtaaatca acaggcagga ccttatgtaa tgatgattgg aaaaatggtg gccaatatgt | 1080 |
| tctacattgt agtgattatg gctcttgtat tacttagttt tggtgttccc agaaaggcaa | 1140 |
| tactttatcc tcatgaagca ccatcttgga ctccttgctaa agatatagtt tttcacccat | 1200 |
| actggatgat ttttggtgaa gtttatgcat acgaaattga tgtgtgtgca aatgattctg | 1260 |
| ttatccctca aatctgtggt cctgggacgt ggttgactcc atttcttcaa gcagtctacc | 1320 |
| tcttttgtaca gtatatcatt atggttaatc ttcttattgc attttttcaac aatgtgtatt | 1380 |
| tacaagtgaa ggcaatttcc aatattgtat ggaagtacca gcgttatcat tttattatgg | 1440 |
| cttatcatga gaaaccagtt ctgcctcctc cacttatcat tcttagccat atagtttctc | 1500 |
| tgttttgctg catatgtaag agaagaaaga aagataagac ttccgatgga ccaaaacttt | 1560 |
| tcttaacaga agaagatcaa aagaaacttc atgattttga gagcagtgt gttgaaatgt | 1620 |
| atttcaatga aaaagatgac aaatttcatt ctgggagtga agagagaatt cgtgtcactt | 1680 |
| ttgaaagagt ggaacagatg tgcattcaga ttaaagaagt tggagatcgt gtcaactaca | 1740 |
| taaaaagatc attacaatca ttagattctc aaattggcca tttgcaagat ctttcagccc | 1800 |
| tgacggtaga tacattaaaa acactcactg cccagaaagc gtcggaagct agcaaagttc | 1860 |
| ataatgaaat cacacgagaa ctgagcattt ccaaacactt ggctcaaaac cttattgatg | 1920 |
| atggtcctgt aagaccttct gtatggaaaa agcatggtgt tgtaaataca cttagctcct | 1980 |
| ctcttcctca aggtgatctt gaaagtaata atccttttca ttgtaatatt ttaatgaaag | 2040 |
| atgacaaaga tcccccagtgt aatatatttg gtcaagactt acctgcagta ccccagagaa | 2100 |
| aagaatttaa ttttccagag gctggttcct cttctggtgc cttattccca agtgctgttt | 2160 |
| cccctccaga actgcgacag agactacatg gggtagaact cttaaaaata tttaataaaa | 2220 |
| atcaaaaatt aggcagttca tctactagca taccacatct gtcatcccca ccaaccaaat | 2280 |
| tttttgttag tacaccatct cagccaagtt gcaaaagcca cttggaaact ggaaccaaag | 2340 |
| atcaagaaac tgtttgctct aaagctacag aaggagataa tncagaattt ggagcatttg | 2400 |
| taggacacag agatagcatg gatttacaga ggtttaaaga aacatcaaac aagataaaaa | 2460 |
| tactatccaa taacaatact tctgaaaaca ctttgaaacg agtgagttct cttgctggat | 2520 |
| ttactgactg tcacagaact tccattcctg ttcattcaaa acaagcagaa aaaatcagta | 2580 |
| gaaggccatc taccgaagac actcatgaag tagattccaa agcagcttta ataccggatt | 2640 |
| ggttacaaga tagaccatca aacagagaaa tgccatctga agaaggaaca ttaaatggtc | 2700 |
| tcacttctcc atttaagcca gctatggata caaattacta ttattcagct gtggaaagaa | 2760 |
| ataacttgat gaggttatca cagagcattc catttcacc tgtgcctcca agaggggagc | 2820 |
| ctgtcacagt gtatcgtttg aagagagtt cacccaacat actaaataac agcatgtctt | 2880 |

```
cttggtcaca actaggcctc tgtgccaaaa tagagttttt aagcaaagag gagatgggag    2940
gaggtttacg aagagctgtc aaagtacagt gtacctggtc agaacatgat atcctcaaat    3000
cagggcatct ttatattatc aaatcttttc ttccagaggt ggttaataca tggtcaagta    3060
tttataaaga agatacagtt ctgcatctct gtctgagaga aattcaacaa cagagagcag    3120
cacaaaagct tacgtttgcc tttaatcaaa tgaaacccaa atccatacca tattctccaa    3180
ggttccttga agttttcctg ctgtattgcc attcagcagg acagtggttt gctgtggaag    3240
aatgtatgac tggagaattt agaaaataca acaataataa tggagatgag attattccaa    3300
ctaatactct ggaagagatc atgctagcct ttagccactg gacttacgaa tatacaagag    3360
gggagttact ggtacttgat ttgcaaggtg ttggtgaaaa tttgactgac ccatctgtga    3420
taaaagcaga agaaaagaga tcctgtgata tggttttggg cccagcaaat ctaggagaag    3480
atgcaattaa aaacttcaga gcaaaacatc actgtaattc ttgctgtaga aagcttaaac    3540
ttccagatct gaagaggaat gattatacgc ctgataaaat tatatttcct caggatgagc    3600
cttcagattt gaatcttcag cctggaaatt ccaccaaaga atcagaatca gctaattctg    3660
ttcgtctgat gttataatat taatattact gaatcattgg ttttgcctgc acctcacaga    3720
aatgttactg tgtcactttt ccctcgggag gaaattgttt ggtaatatag aaaggtgtat    3780
gcaagttgaa tttgctgact ccagcacagt taaaaggtca atattctttt gacctgatta    3840
atcagtcaga aagtccctat aggatagagc tggcagctga gaaatttttaa aggtaattga    3900 taattagtat ttgtaacttt ttaaagggct ctttgtatag cagaggatct catttgactt    3960
tgttttgatg agggtgatgc cctctcttat gtggtacaat accattaacc aaaggtaggt    4020
gtccatgcag atttttattgg cagctgtttt attgccattc aactagggaa atgaagaaat    4080
cacgcagcct tttggttaaa tggcagtcaa aattttcctc agtgtattta gtgtgttcag    4140
tgatgatatc actggttccc aactagatgc ttgttggcca cgggaaggga aatgacttgt    4200
tctaattcta ggttcacaga ggtatgagaa gcctgaactg aagaccattt tcaagaggga    4260
cggtatttat gaatcagggt taggctccat atttaaagat agagccagtt tttttttaa    4320 atagaaccca aattgtgtaa aaatgttaat tgggtttttt aaacattgtt ttatcaagtc    4380
actgttaagt agaagaaagc catggtaaac tgatacataa cctaaattat aaaagcagaa    4440
acctaactca ctcgtcaagg gaagttacct tttgaggaaa gttaaagtac tttttttccct    4500 atctgtatct atagcaacaa cccagaactt acaaacttct ccaaagattt tattgattgt    4560
tatatcaaat cagaatgtaa acatgaactc ttgcatatat ttaaaattgt gttggaacat    4620
ttgaacatga atgctgtttg ggtacttaag aaaattrattc agtnggatta tcattatgtg    4680
anactggcag attgcagtgc anccttatgc caataaaatg taatttaaca gccccagata    4740
ttgttgaata ttcaacaata acaagaaaag ctttttcatct aagttttatg ctttaatttt    4800
ttttcttttt ttttcttttt cttttgtttc cttggtacta attttaatttt ttatttggaa    4860 gggagcagta taaagcttat ttgtatttag tagtgtatct catagataca gacaaggcaa    4920
gagatgataa gctgtttaaa tagtgtttaa tattgattgg gggtggggag aaagaaaaag    4980
tgtattactt aaagatacta tatacgttttt gtatatcatt aaatctttaa aagaaatnna    5040
ataaatttat tgtttncaaa aaaaaaaccc nntaaaaaaa aaagggcggc ccctctagag    5100
gatccctcga ggggccc                                                   5117
```

<210> SEQ ID NO 24

-continued

```
<211> LENGTH: 1224
<212> TYPE: PRT
<213> ORGANISM: Homo sapiens
<220> FEATURE:
<221> NAME/KEY: UNSURE
<222> LOCATION: (794)..(794)
<223> OTHER INFORMATION: any amino acid

<400> SEQUENCE: 24

Trp Gln His Gly Glu Glu Ser Met Ala Lys Ala Leu Val Ala Cys Lys
1               5                   10                  15

Ile Tyr Arg Ser Met Ala Tyr Glu Ala Lys Gln Ser Asp Leu Val Asp
            20                  25                  30

Asp Thr Ser Glu Glu Leu Lys Gln Tyr Ser Asn Asp Phe Gly Gln Leu
        35                  40                  45

Ala Val Glu Leu Leu Glu Gln Ser Phe Arg Gln Asp Glu Thr Met Ala
    50                  55                  60

Met Lys Leu Leu Thr Tyr Glu Leu Lys Asn Trp Ser Asn Ser Thr Cys
65                  70                  75                  80

Leu Lys Leu Ala Val Ser Ser Arg Leu Arg Pro Phe Val Ala His Thr
                85                  90                  95

Cys Thr Gln Met Leu Leu Ser Asp Met Trp Met Gly Arg Leu Asn Met
            100                 105                 110

Arg Lys Asn Ser Trp Tyr Lys Val Ile Leu Ser Ile Leu Val Pro Pro
        115                 120                 125

Ala Ile Leu Leu Leu Glu Tyr Lys Thr Lys Ala Glu Met Ser His Ile
    130                 135                 140

Pro Gln Ser Gln Asp Ala His Gln Met Thr Met Asp Asp Ser Glu Asn
145                 150                 155                 160

Asn Phe Gln Asn Ile Thr Glu Glu Ile Pro Met Glu Val Phe Lys Glu
                165                 170                 175

Val Arg Ile Leu Asp Ser Asn Glu Gly Lys Asn Glu Met Glu Ile Gln
            180                 185                 190

Met Lys Ser Lys Lys Leu Pro Ile Thr Arg Lys Phe Tyr Ala Phe Tyr
        195                 200                 205

His Ala Pro Ile Val Lys Phe Trp Phe Asn Thr Leu Ala Tyr Leu Gly
    210                 215                 220

Phe Leu Met Leu Tyr Thr Phe Val Val Leu Val Gln Met Glu Gln Leu
225                 230                 235                 240

Pro Ser Val Gln Glu Trp Ile Val Ile Ala Tyr Ile Phe Thr Tyr Ala
                245                 250                 255

Ile Glu Lys Val Arg Glu Ile Phe Met Ser Glu Ala Gly Lys Val Asn
            260                 265                 270

Gln Lys Ile Lys Val Trp Phe Ser Asp Tyr Phe Asn Ile Ser Asp Thr
        275                 280                 285

Ile Ala Ile Ile Ser Phe Phe Ile Gly Phe Gly Leu Arg Phe Gly Ala
    290                 295                 300

Lys Trp Asn Phe Ala Asn Ala Tyr Asp Asn His Val Phe Val Ala Gly
305                 310                 315                 320

Arg Leu Ile Tyr Cys Leu Asn Ile Ile Phe Trp Tyr Val Arg Leu Leu
                325                 330                 335

Asp Phe Leu Ala Val Asn Gln Gln Ala Gly Pro Tyr Val Met Met Ile
            340                 345                 350

Gly Lys Met Val Ala Asn Met Phe Tyr Ile Val Val Ile Met Ala Leu
        355                 360                 365
```

-continued

```
Val Leu Leu Ser Phe Gly Val Pro Arg Lys Ala Ile Leu Tyr Pro His
    370             375                 380
Glu Ala Pro Ser Trp Thr Leu Ala Lys Asp Ile Val Phe His Pro Tyr
385                 390                 395                 400
Trp Met Ile Phe Gly Glu Val Tyr Ala Tyr Glu Ile Asp Val Cys Ala
                405                 410                 415
Asn Asp Ser Val Ile Pro Gln Ile Cys Gly Pro Gly Thr Trp Leu Thr
                420                 425                 430
Pro Phe Leu Gln Ala Val Tyr Leu Phe Val Gln Tyr Ile Ile Met Val
        435                 440                 445
Asn Leu Leu Ile Ala Phe Phe Asn Asn Val Tyr Leu Gln Val Lys Ala
    450                 455                 460
Ile Ser Asn Ile Val Trp Lys Tyr Gln Arg Tyr His Phe Ile Met Ala
465                 470                 475                 480
Tyr His Glu Lys Pro Val Leu Pro Pro Pro Leu Ile Ile Leu Ser His
                485                 490                 495
Ile Val Ser Leu Phe Cys Cys Ile Cys Lys Arg Arg Lys Lys Asp Lys
                500                 505                 510
Thr Ser Asp Gly Pro Lys Leu Phe Leu Thr Glu Glu Asp Gln Lys Lys
        515                 520                 525
Leu His Asp Phe Glu Glu Gln Cys Val Glu Met Tyr Phe Asn Glu Lys
    530                 535                 540
Asp Asp Lys Phe His Ser Gly Ser Glu Glu Arg Ile Arg Val Thr Phe
545                 550                 555                 560
Glu Arg Val Glu Gln Met Cys Ile Gln Ile Lys Glu Val Gly Asp Arg
                565                 570                 575
Val Asn Tyr Ile Lys Arg Ser Leu Gln Ser Leu Asp Ser Gln Ile Gly
                580                 585                 590
His Leu Gln Asp Leu Ser Ala Leu Thr Val Asp Thr Leu Lys Thr Leu
        595                 600                 605
Thr Ala Gln Lys Ala Ser Glu Ala Ser Lys Val His Asn Glu Ile Thr
    610                 615                 620
Arg Glu Leu Ser Ile Ser Lys His Leu Ala Gln Asn Leu Ile Asp Asp
625                 630                 635                 640
Gly Pro Val Arg Pro Ser Val Trp Lys Lys His Gly Val Val Asn Thr
                645                 650                 655
Leu Ser Ser Ser Leu Pro Gln Gly Asp Leu Glu Ser Asn Asn Pro Phe
                660                 665                 670
His Cys Asn Ile Leu Met Lys Asp Asp Lys Asp Pro Gln Cys Asn Ile
        675                 680                 685
Phe Gly Gln Asp Leu Pro Ala Val Pro Gln Arg Lys Glu Phe Asn Phe
    690                 695                 700
Pro Glu Ala Gly Ser Ser Gly Ala Leu Phe Pro Ser Ala Val Ser
705                 710                 715                 720
Pro Pro Glu Leu Arg Gln Arg Leu His Gly Val Glu Leu Leu Lys Ile
                725                 730                 735
Phe Asn Lys Asn Gln Lys Leu Gly Ser Ser Thr Ser Ile Pro His
        740                 745                 750
Leu Ser Ser Pro Pro Thr Lys Phe Phe Val Ser Thr Pro Ser Gln Pro
    755                 760                 765
Ser Cys Lys Ser His Leu Glu Thr Gly Thr Lys Asp Gln Glu Thr Val
770                 775                 780
Cys Ser Lys Ala Thr Glu Gly Asp Asn Xaa Glu Phe Gly Ala Phe Val
```

-continued

```
            785                 790                 795                 800
Gly His Arg Asp Ser Met Asp Leu Gln Arg Phe Lys Glu Thr Ser Asn
                805                 810                 815
Lys Ile Lys Ile Leu Ser Asn Asn Thr Ser Glu Asn Thr Leu Lys
        820                 825                 830
Arg Val Ser Ser Leu Ala Gly Phe Thr Asp Cys His Arg Thr Ser Ile
        835                 840                 845
Pro Val His Ser Lys Gln Ala Glu Lys Ile Ser Arg Arg Pro Ser Thr
850                 855                 860
Glu Asp Thr His Glu Val Asp Ser Lys Ala Ala Leu Ile Pro Asp Trp
865                 870                 875                 880
Leu Gln Asp Arg Pro Ser Asn Arg Glu Met Pro Ser Glu Gly Thr
                885                 890                 895
Leu Asn Gly Leu Thr Ser Pro Phe Lys Pro Ala Met Asp Thr Asn Tyr
                900                 905                 910
Tyr Tyr Ser Ala Val Glu Arg Asn Asn Leu Met Arg Leu Ser Gln Ser
                915                 920                 925
Ile Pro Phe Thr Pro Val Pro Pro Arg Gly Glu Pro Val Thr Val Tyr
        930                 935                 940
Arg Leu Glu Glu Ser Ser Pro Asn Ile Leu Asn Asn Ser Met Ser Ser
945                 950                 955                 960
Trp Ser Gln Leu Gly Leu Cys Ala Lys Ile Glu Phe Leu Ser Lys Glu
                965                 970                 975
Glu Met Gly Gly Gly Leu Arg Arg Ala Val Lys Val Gln Cys Thr Trp
        980                 985                 990
Ser Glu His Asp Ile Leu Lys Ser  Gly His Leu Tyr Ile  Ile Lys Ser
        995                 1000                 1005
Phe Leu  Pro Glu Val Val Asn  Thr Trp Ser Ser Ile  Tyr Lys Glu
        1010                 1015                 1020
Asp Thr  Val Leu His Leu Cys  Leu Arg Glu Ile Gln  Gln Gln Arg
        1025                 1030                 1035
Ala Ala  Gln Lys Leu Thr Phe  Ala Phe Asn Gln Met  Lys Pro Lys
        1040                 1045                 1050
Ser Ile  Pro Tyr Ser Pro Arg  Phe Leu Glu Val Phe  Leu Leu Tyr
        1055                 1060                 1065
Cys His  Ser Ala Gly Gln Trp  Phe Ala Val Glu Glu  Cys Met Thr
        1070                 1075                 1080
Gly Glu  Phe Arg Lys Tyr Asn  Asn Asn Asn Gly Asp  Glu Ile Ile
        1085                 1090                 1095
Pro Thr  Asn Thr Leu Glu Glu  Ile Met Leu Ala Phe  Ser His Trp
        1100                 1105                 1110
Thr Tyr  Glu Tyr Thr Arg Gly  Glu Leu Leu Val Leu  Asp Leu Gln
        1115                 1120                 1125
Gly Val  Gly Glu Asn Leu Thr  Asp Pro Ser Val Ile  Lys Ala Glu
        1130                 1135                 1140
Glu Lys  Arg Ser Cys Asp Met  Val Phe Gly Pro Ala  Asn Leu Gly
        1145                 1150                 1155
Glu Asp  Ala Ile Lys Asn Phe  Arg Ala Lys His His  Cys Asn Ser
        1160                 1165                 1170
Cys Cys  Arg Lys Leu Lys Leu  Pro Asp Leu Lys Arg  Asn Asp Tyr
        1175                 1180                 1185
Thr Pro  Asp Lys Ile Ile Phe  Pro Gln Asp Glu Pro  Ser Asp Leu
        1190                 1195                 1200
```

Asn Leu Gln Pro Gly Asn Ser Thr Lys Glu Ser Glu Ser Ala Asn
    1205                 1210                1215

Ser Val Arg Leu Met Leu
    1220

<210> SEQ ID NO 25
<211> LENGTH: 2180
<212> TYPE: DNA
<213> ORGANISM: Homo sapiens

<400> SEQUENCE: 25

| | | | | | |
|---|---|---|---|---|---|
| tcgaggccaa | gaattcggca | cgagggcctc | gggcaggccc | cctggagcga | cctgcttctt | 60 |
| tgggcactgt | tgctgaacag | ggcacagatg | gccatgtact | tctgggagat | gggttccaat | 120 |
| gcagtttcct | cagctcttgg | ggcctgtttg | ctgctccggg | tgatggcacg | cctggagcct | 180 |
| gacgctgagg | aggcagcacg | gaggaaagac | ctggcgttca | gtttgagggg | atgggcgtt | 240 |
| gacctctttg | gcgagtgcta | tcgcagcagt | gaggtgaggg | ctgcccgcct | cctcctccgt | 300 |
| cgctgcccgc | tctgggggga | tgccacttgc | ctccagctgg | ccatgcaagc | tgacgcccgt | 360 |
| gccttctttg | cccaggatgg | ggtacagtct | ctgctgacac | agaagtggtg | gggagatatg | 420 |
| gccagcacta | cacccatctg | ggccctggtt | ctcgccttct | tttgccctcc | actcatctac | 480 |
| acccgcctca | tcaccttcag | gaaatcagaa | gaggagccca | cacggaggga | gctagagttt | 540 |
| gacatggata | gtgtcattaa | tgggaaggg | cctgtcggga | cggcggaccc | agccgagaag | 600 |
| acgccgctgg | gggtcccgcg | ccagtcgggc | cgtccgggtt | gctgcggggg | ccgctgcggg | 660 |
| gggcgccggt | gcctacgccg | ctggttccac | ttctggggcg | cgccggtgac | catcttcatg | 720 |
| ggcaacgtgg | tcagctacct | gctgttcctg | ctgcttttct | cgcgggtgct | gctcgtggat | 780 |
| ttccagccgg | cgccgcccgg | ctccctggag | ctgctgctct | atttctgggc | tttcacgctg | 840 |
| ctgtgcgagg | aactgcgcca | gggcctgagc | ggaggcgggg | gcagcctcgc | cagcgggggc | 900 |
| cccgggcctg | gccatgcctc | actgagccag | cgcctgcgcc | tctacctcgc | cgacagctgg | 960 |
| aaccagtgcg | acctagtggc | tctcacctgc | ttcctcctgg | gcgtgggctg | ccggctgacc | 1020 |
| ccgggtttgt | accacctggg | ccgcactgtc | ctctgcatcg | acttcatggt | tttcacggtg | 1080 |
| cggctgcttc | acatcttcac | ggtcaacaaa | cagctgggc | ccaagatcgt | catcgtgagc | 1140 |
| aagatgatga | aggacgtgtt | cttcttcctc | ttcttcctcg | gcgtgtggct | ggtagcctat | 1200 |
| ggcgtggcca | cggaggggct | cctgaggcca | cggacagtg | acttcccaag | tatcctgcgc | 1260 |
| cgcgtcttct | accgtcccta | cctgcagatc | ttcgggcaga | ttccccagga | ggacatggac | 1320 |
| gtggccctca | tggagcacag | caactgctcg | tcggagcccg | gcttctgggc | acaccctcct | 1380 |
| ggggcccagg | cgggcacctg | cgtctcccag | tatgccaact | ggctggtggt | gctgctcctc | 1440 |
| gtcatcttcc | tgctcgtggc | caacatcctg | ctggtcaact | tgctcattgc | catgttcagt | 1500 |
| tacacattcg | gcaaagtaca | gggcaacagc | gatctctact | ggaaggcgca | gcgttaccgc | 1560 |
| ctcatccggg | aattccactc | tcggcccgcg | ctggccccgc | cctttatcgt | catctcccac | 1620 |
| ttgcgcctcc | tgctcaggca | attgtgcagg | cgacccsgga | gccccagcc | gtcctccccg | 1680 |
| gccctcgagc | atttccgggt | ttaccttcct | aaggaagccg | agcggaagct | gctaacgtgg | 1740 |
| gaatcggtgc | ataaggagaa | ctttctgctg | gcacgcgcta | gggacaagcg | ggagagcgac | 1800 |
| tccgagmgtc | tgaagcgcac | gtcccagaag | gtgacttgg | cactgaaaca | gctgggacac | 1860 |
| atccgcgagt | acgaacagcg | cctgaaagtg | ctggagcggg | aggtccagca | gtgtacctcg | 1920 |

-continued

```
gcccccgcac ctggtggcct tgtccttgag gtgagcccca tgtccatctg ggccactgtc    1980
aggaccacct ttgggagtgt catccttaca aaccacagca tgcccggctc ctcccagaac    2040
cagtcccagc ctgggaggat caaggcctgg atcccrggcc gttatccatc tggaggctgc    2100
agggtccttg gggtaacagg gaccacagac ccctcaccac tcacagattc ctcacactgg    2160
ggaaataaag ccatttcaga                                                2180
```

<210> SEQ ID NO 26
<211> LENGTH: 725
<212> TYPE: PRT
<213> ORGANISM: Homo sapiens
<220> FEATURE:
<221> NAME/KEY: UNSURE
<222> LOCATION: (553)..(553)
<223> OTHER INFORMATION: any amino acid
<220> FEATURE:
<221> NAME/KEY: UNSURE
<222> LOCATION: (603)..(603)
<223> OTHER INFORMATION: any amino acid

<400> SEQUENCE: 26

```
Ser Arg Pro Arg Ile Arg His Glu Gly Leu Gly Gln Ala Pro Trp Ser
1               5                   10                  15

Asp Leu Leu Trp Ala Leu Leu Asn Arg Ala Gln Met Ala Met
            20                  25                  30

Tyr Phe Trp Glu Met Gly Ser Asn Ala Val Ser Ser Ala Leu Gly Ala
        35                  40                  45

Cys Leu Leu Leu Arg Val Met Ala Arg Leu Glu Pro Asp Ala Glu Glu
    50                  55                  60

Ala Ala Arg Arg Lys Asp Leu Ala Phe Lys Phe Glu Gly Met Gly Val
65                  70                  75                  80

Asp Leu Phe Gly Glu Cys Tyr Arg Ser Ser Glu Val Arg Ala Ala Arg
                85                  90                  95

Leu Leu Leu Arg Arg Cys Pro Leu Trp Gly Asp Ala Thr Cys Leu Gln
            100                 105                 110

Leu Ala Met Gln Ala Asp Ala Arg Ala Phe Phe Ala Gln Asp Gly Val
        115                 120                 125

Gln Ser Leu Leu Thr Gln Lys Trp Trp Gly Asp Met Ala Ser Thr Thr
    130                 135                 140

Pro Ile Trp Ala Leu Val Leu Ala Phe Phe Cys Pro Pro Leu Ile Tyr
145                 150                 155                 160

Thr Arg Leu Ile Thr Phe Arg Lys Ser Glu Glu Pro Thr Arg Glu
                165                 170                 175

Glu Leu Glu Phe Asp Met Asp Ser Val Ile Asn Gly Glu Gly Pro Val
            180                 185                 190

Gly Thr Ala Asp Pro Ala Glu Lys Thr Pro Leu Gly Val Pro Arg Gln
        195                 200                 205

Ser Gly Arg Pro Gly Cys Cys Gly Gly Arg Cys Gly Arg Arg Cys
    210                 215                 220

Leu Arg Arg Trp Phe His Phe Trp Gly Ala Pro Val Thr Ile Phe Met
225                 230                 235                 240

Gly Asn Val Val Ser Tyr Leu Leu Phe Leu Leu Phe Ser Arg Val
                245                 250                 255

Leu Leu Val Asp Phe Gln Pro Ala Pro Pro Gly Ser Leu Glu Leu Leu
            260                 265                 270

Leu Tyr Phe Trp Ala Phe Thr Leu Leu Cys Glu Glu Leu Arg Gln Gly
        275                 280                 285
```

-continued

```
Leu Ser Gly Gly Gly Ser Leu Ala Ser Gly Gly Pro Gly Pro Gly
    290                 295                 300
His Ala Ser Leu Ser Gln Arg Leu Arg Leu Tyr Leu Ala Asp Ser Trp
305                 310                 315                 320
Asn Gln Cys Asp Leu Val Ala Leu Thr Cys Phe Leu Leu Gly Val Gly
                325                 330                 335
Cys Arg Leu Thr Pro Gly Leu Tyr His Leu Gly Arg Thr Val Leu Cys
            340                 345                 350
Ile Asp Phe Met Val Phe Thr Val Arg Leu Leu His Ile Phe Thr Val
        355                 360                 365
Asn Lys Gln Leu Gly Pro Lys Ile Val Ile Val Ser Lys Met Met Lys
370                 375                 380
Asp Val Phe Phe Phe Leu Phe Phe Leu Gly Val Trp Leu Val Ala Tyr
385                 390                 395                 400
Gly Val Ala Thr Glu Gly Leu Leu Arg Pro Arg Asp Ser Asp Phe Pro
                405                 410                 415
Ser Ile Leu Arg Arg Val Phe Tyr Arg Pro Tyr Leu Gln Ile Phe Gly
            420                 425                 430
Gln Ile Pro Gln Glu Asp Met Asp Val Ala Leu Met Glu His Ser Asn
        435                 440                 445
Cys Ser Ser Glu Pro Gly Phe Trp Ala His Pro Gly Ala Gln Ala
450                 455                 460
Gly Thr Cys Val Ser Gln Tyr Ala Asn Trp Leu Val Val Leu Leu Leu
465                 470                 475                 480
Val Ile Phe Leu Leu Val Ala Asn Ile Leu Leu Val Asn Leu Leu Ile
                485                 490                 495
Ala Met Phe Ser Tyr Thr Phe Gly Lys Val Gln Gly Asn Ser Asp Leu
            500                 505                 510
Tyr Trp Lys Ala Gln Arg Tyr Arg Leu Ile Arg Glu Phe His Ser Arg
        515                 520                 525
Pro Ala Leu Ala Pro Pro Phe Ile Val Ile Ser His Leu Arg Leu Leu
530                 535                 540
Leu Arg Gln Leu Cys Arg Arg Pro Xaa Ser Pro Gln Pro Ser Ser Pro
545                 550                 555                 560
Ala Leu Glu His Phe Arg Val Tyr Leu Ser Lys Glu Ala Glu Arg Lys
                565                 570                 575
Leu Leu Thr Trp Glu Ser Val His Lys Glu Asn Phe Leu Leu Ala Arg
            580                 585                 590
Ala Arg Asp Lys Arg Glu Ser Asp Ser Glu Xaa Leu Lys Arg Thr Ser
        595                 600                 605
Gln Lys Val Asp Leu Ala Leu Lys Gln Leu Gly His Ile Arg Glu Tyr
610                 615                 620
Glu Gln Arg Leu Lys Val Leu Glu Arg Glu Val Gln Gln Cys Thr Ser
625                 630                 635                 640
Ala Pro Ala Pro Gly Gly Leu Val Leu Glu Val Ser Pro Met Ser Ile
                645                 650                 655
Trp Ala Thr Val Arg Thr Thr Phe Gly Ser Val Ile Leu Thr Asn His
            660                 665                 670
Ser Met Pro Gly Ser Ser Gln Asn Gln Ser Gln Pro Gly Arg Ile Lys
        675                 680                 685
Ala Trp Ile Pro Gly Arg Tyr Pro Ser Gly Gly Cys Arg Val Leu Gly
690                 695                 700
```

```
Val Thr Gly Thr Thr Asp Pro Ser Pro Leu Thr Asp Ser Ser His Trp
705                 710                 715                 720

Gly Asn Lys Ala Ile
            725

<210> SEQ ID NO 27
<211> LENGTH: 7419
<212> TYPE: DNA
<213> ORGANISM: Homo sapiens
<220> FEATURE:
<221> NAME/KEY: Unsure
<222> LOCATION: (158)..(158)
<223> OTHER INFORMATION: a, or c, or g, or t
<220> FEATURE:
<221> NAME/KEY: Unsure
<222> LOCATION: (6966)..(6966)
<223> OTHER INFORMATION: a, or c, or g, or t
<220> FEATURE:
<221> NAME/KEY: Unsure
<222> LOCATION: (6984)..(6984)
<223> OTHER INFORMATION: a, or c, or g, or t
<220> FEATURE:
<221> NAME/KEY: Unsure
<222> LOCATION: (7004)..(7004)
<223> OTHER INFORMATION: a, or c, or g, or t
<220> FEATURE:
<221> NAME/KEY: Unsure
<222> LOCATION: (7340)..(7341)
<223> OTHER INFORMATION: a, or c, or g, or t
<220> FEATURE:
<221> NAME/KEY: Unsure
<222> LOCATION: (7358)..(7358)
<223> OTHER INFORMATION: a, or c, or g, or t
<220> FEATURE:
<221> NAME/KEY: Unsure
<222> LOCATION: (7373)..(7374)
<223> OTHER INFORMATION: a, or c, or g, or t

<400> SEQUENCE: 27
cggggaccga tccagcctcc ggactctagc ctaggctttt gcaaaaagct atttaggtga      60
cactatagaa ggtacgcctg caggtaccgg tccggaattc ccgggtcgac ccacgcgtcc     120
gcagccccgt cgccggcgga ggcgggcgcg ggcgcgtncc ctgtggccag tcacccggag     180
gagttggtcg cacaattatg aaagactcgg cttctgctgc tagcgccgga gctgagttag     240
ttctgagaag gtttcctggg gcgttccttg tccggcggcc tctgctgccg cctccggaga     300
cgcttcccga tagatggcta caggccgcgg aggaggagga ggtggagttg ctgcccttcc     360
ggagtccgcc ccgtgaggag aatgtcccag aaatcctgga tagaaagcac tttgaccaag     420
agggaatgtg tatatattat accaagttcc aaggaccctc acagatgcct tccaggatgt     480
caaatttgtc agcaactcgt caggtgtttt tgtggtcgct tggtcaagca acatgcttgt     540
tttactgcaa gtcttgccat gaaatactca gatgtgaaat tgggtgacca tttttaatcag    600 gcaatagaag aatggtctgt ggaaaagcat acagaacaga gcccaacgga tgcttatgga     660
gtcataaatt ttcaagggg ttctcattcc tacagagcta agtatgtgag gctatcatat      720
gacaccaaac ctgaagtcat tctgcaactt ctgcttaaag aatggcaaat ggagttaccc     780
aaacttgtta tctctgtaca tgggggcatg cagaaatttg agcttcaccc acgaatcaag     840
cagttgcttg gaaaggtct tattaaagct gcagttacaa ctggagcctg gattttaact      900
ggaggagtaa acacaggtgt ggcaaaacat gttggagatg ccctcaaaga acatgcttcc     960
agatcatctc gaaagatttg cactatcgga atagctccat ggggagtgat tgaaaacaga    1020
aatgatcttg ttgggagaga tgtggttgct cctatcaaa ccttattgaa ccccctgagc     1080
aaattgaatg ttttgaataa tctgcattcc catttcatat tggtggatga tggcactgtt    1140
```

```
ggaaagtatg gggcggaagt cagactgaga agagaacttg aaaaaactat taatcagcaa    1200
agaattcatg ctaggattgg ccagggtgtc cctgtggtgg cacttatatt tgagggtggg    1260
ccaaatgtta tcctcacagt tcttgaatac cttcaggaaa gcccccctgt tccagtagtt    1320
gtgtgtgaag gaacaggcag agctgcagat ctgctagcgt atattcataa acaaacagaa    1380
gaaggaggga atcttcctga tgcagcagag cccgatatta tttccactat caaaaaaaca    1440
tttaactttg gccagaatga agcacttcat ttatttcaaa cactgatgga gtgcatgaaa    1500
agaaaggagc ttatcactgt tttccatatt gggtcagatg aacatcaaga tatagatgta    1560
gcaatactta ctgcactgct aaaaggtact aatgcatctg catttgacca gcttatcctt    1620
acattggcat gggatagagt tgacattgcc aaaaatcatg tatttgttta tggacagcag    1680
tggctggttg gatccttgga acaagctatg cttgatgctc ttgtaatgga tagagttgca    1740
tttgtaaaac ttcttattga aaatggagta agcatgcata aattccttac cattccgaga    1800
ctggaagaac tttacaacac taaacaaggt ccaactaatc caatgctgtt tcatcttgtt    1860
cgagacgtca acagggaaa tcttcctcca ggatataaga tcactctgat tgatataggn    1920
cttgttattg aatatctcat gggaggaacc tacagatgca cctatactag gaaacgtttt    1980
cgattaatat ataatagtct tggtggaaat aatcggaggt ctggccgaaa tacctccagc    2040
agcactcctc agttgcgaaa gagtcatgaa tcttttggca atagggcaga taaaaaggaa    2100
aaaatgaggc ataaccattt cattaagaca gcacagccct tccgaccaaa gattgataca    2160
gttatggaag aaggaaagaa gaaaagaacc aaagatgaaa ttgtagacat tgatgatcca    2220
gaaaccaagc gctttcctta tccacttaat gaacttttaa tttgggcttg ccttatgaag    2280
aggcaggtca tggcccgttt tttatggcaa catggtgaag aatcaatggc taaagcatta    2340
gttgcctgta agatctatcg ttcaatggca tatgaagcaa agcagagtga cctggtagat    2400
gatacttcag aagaactaaa acagtattcc aatgattttg gtcagttggc cgttgaatta    2460
ttagaacagt ccttcagaca agatgaaacc atggctatga aattgctcac ttatgaactg    2520
aagaactgga gtaattcaac ctgccttaag ttagcagttt cttcaagact tagacctttt    2580
gtagctcaca cctgtacaca aatgttgtta tctgatatgt ggatgggaag gctgaatatg    2640
aggaaaaatt cctggtacaa ggtcatacta agcattttag ttccacctgc catattgctg    2700
ttagagtata aaactaaggc tgaaatgtcc catatcccac aatctcaaga tgctcatcag    2760
atgacaatgg atgacagcga aaacaacttt cagaacataa cagaagagat ccccatggaa    2820
gtgtttaaag aagtacggat tttggatagt aatgaaggaa agaatgagat ggagatacaa    2880
atgaaatcaa aaaagcttcc aattacgcga aagttttatg cctttttatca tgcaccaatt    2940 gtaaaattct ggtttaacac gttggcatat ttaggatttc tgatgcttta tacatttgtg    3000
gttcttgtac aaatggaaca gttaccttca gttcaagaat ggattgttat tgcttatatt    3060
tttacttatg ccattgagaa agtccgtgag atctttatgt ctgaagctgg gaaagtaaac    3120
cagaagatta agtatggtt tagtgattac ttcaacatca gtgatacaat tgccataatt    3180
tctttcttca ttggatttgg actaagattt ggagcaaaat ggaactttgc aaatgcatat    3240
gataatcatg ttttttgtggc tggaagatta atttactgtc ttaacataat attttggtat    3300
gtgcgtttgc tagattttct agctgtaaat caacaggcag gaccttatgt aatgatgatt    3360
ggaaaaatgg tggccaatat gttctacatt gtagtgatta tggctcttgt attacttagt    3420
tttggtgttc ccagaaaggc aatactttat cctcatgaag caccatcttg gactcttgct    3480
```

```
aaagatatag ttttcaccc atactggatg atttttggtg aagtttatgc atacgaaatt      3540
gatgtgtgtg caaatgattc tgttatccct caaatctgtg gtcctgggac gtggttgact      3600
ccatttcttc aagcagtcta cctctttgta cagtatatca ttatggttaa tcttcttatt      3660
gcatttttca acaatgtgta tttacaagtg aaggcaattt ccaatattgt atggaagtac      3720
cagcgttatc atttattat ggcttatcat gagaaaccag ttctgcctcc tccacttatc       3780
attcttagcc atatagtttc tctgttttgc tgcatatgta agagaagaaa gaaagataag      3840
acttccgatg gaccaaaact tttcttaaca gaagaagatc aaaagaaact tcatgatttt     3900
gaagagcagt gtgttgaaat gtatttcaat gaaaagatg acaaatttca ttctgggagt       3960
gaagagagaa ttcgtgtcac ttttgaaaga gtggaacaga tgtgcattca gattaaagaa      4020
gttggagatc gtgtcaacta cataaaaaga tcattacaat cattagattc tcaaattggc      4080
catttgcaag atctttcagc cctgacggta gatacattaa aaacactcac tgcccagaaa      4140
gcgtcggaag ctagcaaagt tcataatgaa atcacgagg aactgagcat ttccaaacac        4200
ttggctcaaa accttattga tgatggtcct gtaagacctt ctgtatggaa aaagcatggt      4260
gttgtaaata cacttagctc ctctcttcct caaggtgatc ttgaaagtaa taatcctttt      4320
cattgtaata ttttaatgaa agatgacaaa gatccccagt gtaatatatt tggtcaagac      4380
ttacctgcag tacccagag aaaagaattt aattttccag aggctggttc ctcttctggt        4440
gccttattcc caagtgctgt ttcccctcca gaactgcgac agagactaca tggggtagaa      4500
ctcttaaaaa tatttaataa aaatcaaaaa ttaggcagtt catctactag cataccacat      4560
ctgtcatccc caccaaccaa attttttgtt agtacaccat ctcagccaag ttgcaaaagc     4620
cacttggaaa ctggaaccaa agatcaagaa actgtttgct ctaaagctac agaaggagat      4680
aatacagaat ttggagcatt tgtaggacac agagatagca tggatttaca gaggtttaaa     4740
gaaacatcaa acaagataaa aatactatcc aataacaata cttctgaaaa cactttgaaa     4800
cgagtgagtt ctcttgctgg atttactgac tgtcacagaa cttccattcc tgttcattca      4860
aaacaagcag aaaaaatcag tagaaggcca tctaccgaag acactcatga agtagattcc      4920
aaagcagctt taataccgga ttggttacaa gatagaccat caaacagaga aatgccatct      4980
gaagaaggaa cattaaatgg tctcacttct ccatttaagc cagctatgga tacaaattac      5040
tattattcag ctgtggaaag aaataacttg atgaggttat cacagagcat tccatttaca      5100
cctgtgcctc caagagggga gcctgtcaca gtgtatcgtt tggaagagag ttcacccaac      5160
atactaaata cagcatgtc ttcttggtca caactaggcc tctgtgccaa aatagagttt        5220
ttaagcaaag aggagatggg aggaggttta cgaagagctg tcaaagtaca gtgtacctgg      5280
tcagaacatg atatcctcaa atcagggcat ctttatatta tcaaatcttt tcttccagag      5340
gtggttaata catggtcaag tatttataaa gaagatacag ttctgcatct ctgtctgaga      5400
gaaattcaac aacagagagc agcacaaaag cttcgtttg cctttaatca aatgaaaccc        5460
aaatccatac catattctcc aaggttcctt gaagttttcc tgctgtattg ccattcagca      5520
ggacagtggt ttgctgtgga agaatgtatg actggagaat ttagaaaata caacaataat      5580
aatggagatg agattattcc aactaatact ctggaagaga tcatgctagc ctttagccac      5640
tggacttacg aatatacaag aggggagtta ctggtacttg atttgcaagg tgttggtgaa      5700
aatttgactg acccatctgt gataaaagca gaagaaaaga gatcctgtga tatggttttt      5760
ggcccagcaa atctaggaga agatgcaatt aaaaacttca gagcaaaaca tcactgtaat      5820
tcttgctgta gaaagcttaa acttccagat ctgaaggaga atgattatac gcctgataaa      5880
```

-continued

```
attatatttc ctcaggatga gccttcagat ttgaatcttc agcctggaaa ttccaccaaa    5940
gaatcagaat caactaattc tgttcgtctg atgttataat attaatatta ctgaatcatt    6000
ggttttgcct gcacctcaca gaaatgttac tgtgtcactt ttccctcggg aggaaattgt    6060
ttggtaatat agaaaggtgt atgcaagttg aatttgctga ctccagcaca gttaaaaggt    6120
caatattctt ttgacctgat taatcagtca gaaagtccct ataggataga ctggcagct     6180
gagaaatttt aaaggtaatt gataattagt atttgtaact ttttaaaggg ctctttgtat    6240
agcagaggat ctcatttgac tttgttttga tgagggtgat gccctctctt atgtggtaca    6300
ataccattaa ccaaaggtag gtgtccatgc agattttatt ggcagctgtt ttattgccat    6360
tcaactaggg aaatgaagaa atcacgcagc cttttggtta aatggcagtc aaaattttcc    6420
tcagtgtatt tagtgtgttc agtgatgata tcactggttc ccaactagat gcttgttggc    6480
cacgggaagg gaaatgactt gttctaattc taggttcaca gaggtatgag aagcctgaac    6540
tgaagaccat tttcaagagg gacggtattt atgaatcagg gttaggctcc atatttaaag    6600
atagagccag tttttttttt aaatagaacc caaattgtgt aaaaatgtta attgggtttt    6660
ttaaacattg ttttatcaag tcactgttaa gtagaagaaa gccatggtaa actgatacat    6720
aacctaaatt ataaaagcag aaacctaact cactcgtcaa gggaagttac cttttgagga    6780
aagttaaagt acttttttcc ctatctgtat ctatagcaac aacccagaac ttacaaactt    6840
ctccaaagat tttattgatt gttatatcaa atcagaatgt aaacatgaac tcttgcatat    6900
atttaaaatt gtgttggaac atttgaacat gaatgctgtt tgggtactta agaaaattrat    6960
tcagtnggat tatcattatg tganactggc agattgcagt gcanccttat gccaataaaa    7020
tgtaatttar cagccccaga tattgttgaa tattcaacaa taacaagaaa agcttttcat    7080
ctaagtttta tgctttaatt tttttttcttt tttttctttt ttcttttgtt tccttggtac   7140
taatttnaat ttttatttgg aagggagcag tataaagctt atttgtattt agtagtgtat    7200
ctcatagata cagacaaggc aagagatgat aagctgttta aatagtgktt aatattgatt    7260
gggggtgggg agaaagaaaa agtgtattac ttaaagatac tatatacskt ttktatatca    7320
ttaaatcttt aaaagaaatn naataaattt attgtttnca aaaaaaaaac ccnntaaaaa    7380
aaaaagggcg gcccctctag aggatccctc gaggggccc                           7419
```

<210> SEQ ID NO 28
<211> LENGTH: 1865
<212> TYPE: PRT
<213> ORGANISM: Homo sapiens

<400> SEQUENCE: 28

```
Met Ser Gln Lys Ser Trp Ile Glu Ser Thr Leu Thr Lys Arg Glu Cys
 1               5                  10                  15

Val Tyr Ile Ile Pro Ser Ser Lys Asp Pro His Arg Cys Leu Pro Gly
            20                  25                  30

Cys Gln Ile Cys Gln Gln Leu Val Arg Cys Phe Cys Gly Arg Leu Val
        35                  40                  45

Lys Gln His Ala Cys Phe Thr Ala Ser Leu Ala Met Lys Tyr Ser Asp
    50                  55                  60

Val Lys Leu Gly Asp His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95
```

```
Phe Gln Gly Gly Ser His Ser Tyr Arg Ala Lys Tyr Val Arg Leu Ser
            100                 105                 110

Tyr Asp Thr Lys Pro Glu Val Ile Leu Gln Leu Leu Leu Lys Glu Trp
        115                 120                 125

Gln Met Glu Leu Pro Lys Leu Val Ile Ser Val His Gly Gly Met Gln
    130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
                165                 170                 175

Asn Thr Gly Val Ala Lys His Val Gly Asp Ala Leu Lys Glu His Ala
            180                 185                 190

Ser Arg Ser Ser Arg Lys Ile Cys Thr Ile Gly Ile Ala Pro Trp Gly
        195                 200                 205

Val Ile Glu Asn Arg Asn Asp Leu Val Gly Arg Asp Val Val Ala Pro
    210                 215                 220

Tyr Gln Thr Leu Leu Asn Pro Leu Ser Lys Leu Asn Val Leu Asn Asn
225                 230                 235                 240

Leu His Ser His Phe Ile Leu Val Asp Asp Gly Thr Val Gly Lys Tyr
                245                 250                 255

Gly Ala Glu Val Arg Leu Arg Arg Glu Leu Glu Lys Thr Ile Asn Gln
            260                 265                 270

Gln Arg Ile His Ala Arg Ile Gly Gln Gly Val Pro Val Val Ala Leu
        275                 280                 285

Ile Phe Glu Gly Gly Pro Asn Val Ile Leu Thr Val Leu Glu Tyr Leu
    290                 295                 300

Gln Glu Ser Pro Pro Val Pro Val Val Cys Glu Gly Thr Gly Arg
305                 310                 315                 320

Ala Ala Asp Leu Leu Ala Tyr Ile His Lys Gln Thr Glu Glu Gly Gly
                325                 330                 335

Asn Leu Pro Asp Ala Ala Glu Pro Asp Ile Ile Ser Thr Ile Lys Lys
            340                 345                 350

Thr Phe Asn Phe Gly Gln Asn Glu Ala Leu His Leu Phe Gln Thr Leu
        355                 360                 365

Met Glu Cys Met Lys Arg Lys Glu Leu Ile Thr Val Phe His Ile Gly
    370                 375                 380

Ser Asp Glu His Gln Asp Ile Asp Val Ala Ile Leu Thr Ala Leu Leu
385                 390                 395                 400

Lys Gly Thr Asn Ala Ser Ala Phe Asp Gln Leu Ile Leu Thr Leu Ala
                405                 410                 415

Trp Asp Arg Val Asp Ile Ala Lys Asn His Val Phe Val Tyr Gly Gln
            420                 425                 430

Gln Trp Leu Val Gly Ser Leu Glu Gln Ala Met Leu Asp Ala Leu Val
        435                 440                 445

Met Asp Arg Val Ala Phe Val Lys Leu Leu Ile Glu Asn Gly Val Ser
    450                 455                 460

Met His Lys Phe Leu Thr Ile Pro Arg Leu Glu Glu Leu Tyr Asn Thr
465                 470                 475                 480

Lys Gln Gly Pro Thr Asn Pro Met Leu Phe His Leu Val Arg Asp Val
                485                 490                 495

Lys Gln Gly Asn Leu Pro Pro Gly Tyr Lys Ile Thr Leu Ile Asp Ile
            500                 505                 510

Gly Leu Val Ile Glu Tyr Leu Met Gly Gly Thr Tyr Arg Cys Thr Tyr
```

-continued

|   |   |   | 515 |   |   |   | 520 |   |   |   | 525 |   |
|---|---|---|---|---|---|---|---|---|---|---|---|---|

Thr Arg Lys Arg Phe Arg Leu Ile Tyr Asn Ser Leu Gly Gly Asn Asn
530                     535                     540

Arg Arg Ser Gly Arg Asn Thr Ser Ser Thr Pro Gln Leu Arg Lys
545                 550                 555                 560

Ser His Glu Ser Phe Gly Asn Arg Ala Asp Lys Lys Glu Lys Met Arg
                565                     570                     575

His Asn His Phe Ile Lys Thr Ala Gln Pro Phe Arg Pro Lys Ile Asp
            580                     585                     590

Thr Val Met Glu Glu Gly Lys Lys Lys Arg Thr Lys Asp Glu Ile Val
        595                     600                     605

Asp Ile Asp Asp Pro Glu Thr Lys Arg Phe Pro Tyr Pro Leu Asn Glu
610                     615                     620

Leu Leu Ile Trp Ala Cys Leu Met Lys Arg Gln Val Met Ala Arg Phe
625                     630                     635                     640

Leu Trp Gln His Gly Glu Glu Ser Met Ala Lys Ala Leu Val Ala Cys
                645                     650                     655

Lys Ile Tyr Arg Ser Met Ala Tyr Glu Ala Lys Gln Ser Asp Leu Val
            660                     665                     670

Asp Asp Thr Ser Glu Glu Leu Lys Gln Tyr Ser Asn Asp Phe Gly Gln
        675                     680                     685

Leu Ala Val Glu Leu Leu Glu Gln Ser Phe Arg Gln Asp Glu Thr Met
690                     695                     700

Ala Met Lys Leu Leu Thr Tyr Glu Leu Lys Asn Trp Ser Asn Ser Thr
705                     710                     715                     720

Cys Leu Lys Leu Ala Val Ser Ser Arg Leu Arg Pro Phe Val Ala His
                725                     730                     735

Thr Cys Thr Gln Met Leu Leu Ser Asp Met Trp Met Gly Arg Leu Asn
            740                     745                     750

Met Arg Lys Asn Ser Trp Tyr Lys Val Ile Leu Ser Ile Leu Val Pro
        755                     760                     765

Pro Ala Ile Leu Leu Leu Glu Tyr Lys Thr Lys Ala Glu Met Ser His
770                     775                     780

Ile Pro Gln Ser Gln Asp Ala His Gln Met Thr Met Asp Asp Ser Glu
785                     790                     795                     800

Asn Asn Phe Gln Asn Ile Thr Glu Glu Ile Pro Met Glu Val Phe Lys
                805                     810                     815

Glu Val Arg Ile Leu Asp Ser Asn Glu Gly Lys Asn Glu Met Glu Ile
            820                     825                     830

Gln Met Lys Ser Lys Lys Leu Pro Ile Thr Arg Lys Phe Tyr Ala Phe
        835                     840                     845

Tyr His Ala Pro Ile Val Lys Phe Trp Phe Asn Thr Leu Ala Tyr Leu
850                     855                     860

Gly Phe Leu Met Leu Tyr Thr Phe Val Val Leu Val Gln Met Glu Gln
865                     870                     875                     880

Leu Pro Ser Val Gln Glu Trp Ile Val Ile Ala Tyr Ile Phe Thr Tyr
                885                     890                     895

Ala Ile Glu Lys Val Arg Glu Ile Phe Met Ser Glu Ala Gly Lys Val
            900                     905                     910

Asn Gln Lys Ile Lys Val Trp Phe Ser Asp Tyr Phe Asn Ile Ser Asp
        915                     920                     925

Thr Ile Ala Ile Ile Ser Phe Phe Ile Gly Phe Gly Leu Arg Phe Gly
930                     935                     940

```
Ala Lys Trp Asn Phe Ala Asn Ala Tyr Asp Asn His Val Phe Val Ala
945                 950                 955                 960

Gly Arg Leu Ile Tyr Cys Leu Asn Ile Ile Phe Trp Tyr Val Arg Leu
                965                 970                 975

Leu Asp Phe Leu Ala Val Asn Gln Gln Ala Gly Pro Tyr Val Met Met
            980                 985                 990

Ile Gly Lys Met Val Ala Asn Met Phe Tyr Ile Val Val Ile Met Ala
        995                 1000                1005

Leu Val Leu Leu Ser Phe Gly Val Pro Arg Lys Ala Ile Leu Tyr
    1010                1015                1020

Pro His Glu Ala Pro Ser Trp Thr Leu Ala Lys Asp Ile Val Phe
    1025                1030                1035

His Pro Tyr Trp Met Ile Phe Gly Glu Val Tyr Ala Tyr Glu Ile
    1040                1045                1050

Asp Val Cys Ala Asn Asp Ser Val Ile Pro Gln Ile Cys Gly Pro
    1055                1060                1065

Gly Thr Trp Leu Thr Pro Phe Leu Gln Ala Val Tyr Leu Phe Val
    1070                1075                1080

Gln Tyr Ile Ile Met Val Asn Leu Leu Ile Ala Phe Phe Asn Asn
    1085                1090                1095

Val Tyr Leu Gln Val Lys Ala Ile Ser Asn Ile Val Trp Lys Tyr
    1100                1105                1110

Gln Arg Tyr His Phe Ile Met Ala Tyr His Glu Lys Pro Val Leu
    1115                1120                1125

Pro Pro Pro Leu Ile Ile Leu Ser His Ile Val Ser Leu Phe Cys
    1130                1135                1140

Cys Ile Cys Lys Arg Arg Lys Asp Lys Thr Ser Asp Gly Pro
    1145                1150                1155

Lys Leu Phe Leu Thr Glu Glu Asp Gln Lys Lys Leu His Asp Phe
    1160                1165                1170

Glu Glu Gln Cys Val Glu Met Tyr Phe Asn Glu Lys Asp Asp Lys
    1175                1180                1185

Phe His Ser Gly Ser Glu Glu Arg Ile Arg Val Thr Phe Glu Arg
    1190                1195                1200

Val Glu Gln Met Cys Ile Gln Ile Lys Glu Val Gly Asp Arg Val
    1205                1210                1215

Asn Tyr Ile Lys Arg Ser Leu Gln Ser Leu Asp Ser Gln Ile Gly
    1220                1225                1230

His Leu Gln Asp Leu Ser Ala Leu Thr Val Asp Thr Leu Lys Thr
    1235                1240                1245

Leu Thr Ala Gln Lys Ala Ser Glu Ala Ser Lys Val His Asn Glu
    1250                1255                1260

Ile Thr Arg Glu Leu Ser Ile Ser Lys His Leu Ala Gln Asn Leu
    1265                1270                1275

Ile Asp Asp Gly Pro Val Arg Pro Ser Val Trp Lys Lys His Gly
    1280                1285                1290

Val Val Asn Thr Leu Ser Ser Ser Leu Pro Gln Gly Asp Leu Glu
    1295                1300                1305

Ser Asn Asn Pro Phe His Cys Asn Ile Leu Met Lys Asp Asp Lys
    1310                1315                1320

Asp Pro Gln Cys Asn Ile Phe Gly Gln Asp Leu Pro Ala Val Pro
    1325                1330                1335
```

-continued

```
Gln Arg Lys Glu Phe Asn Phe Pro Glu Ala Gly Ser Ser Ser Gly
    1340            1345            1350

Ala Leu Phe Pro Ser Ala Val Ser Pro Pro Glu Leu Arg Gln Arg
    1355            1360            1365

Leu His Gly Val Glu Leu Leu Lys Ile Phe Asn Lys Asn Gln Lys
    1370            1375            1380

Leu Gly Ser Ser Ser Thr Ser Ile Pro His Leu Ser Ser Pro Pro
    1385            1390            1395

Thr Lys Phe Phe Val Ser Thr Pro Ser Gln Pro Ser Cys Lys Ser
    1400            1405            1410

His Leu Glu Thr Gly Thr Lys Asp Gln Glu Thr Val Cys Ser Lys
    1415            1420            1425

Ala Thr Glu Gly Asp Asn Thr Glu Phe Gly Ala Phe Val Gly His
    1430            1435            1440

Arg Asp Ser Met Asp Leu Gln Arg Phe Lys Glu Thr Ser Asn Lys
    1445            1450            1455

Ile Lys Ile Leu Ser Asn Asn Asn Thr Ser Glu Asn Thr Leu Lys
    1460            1465            1470

Arg Val Ser Ser Leu Ala Gly Phe Thr Asp Cys His Arg Thr Ser
    1475            1480            1485

Ile Pro Val His Ser Lys Gln Ala Glu Lys Ile Ser Arg Arg Pro
    1490            1495            1500

Ser Thr Glu Asp Thr His Glu Val Asp Ser Lys Ala Ala Leu Ile
    1505            1510            1515

Pro Asp Trp Leu Gln Asp Arg Pro Ser Asn Arg Glu Met Pro Ser
    1520            1525            1530

Glu Glu Gly Thr Leu Asn Gly Leu Thr Ser Pro Phe Lys Pro Ala
    1535            1540            1545

Met Asp Thr Asn Tyr Tyr Tyr Ser Ala Val Glu Arg Asn Asn Leu
    1550            1555            1560

Met Arg Leu Ser Gln Ser Ile Pro Phe Thr Pro Val Pro Pro Arg
    1565            1570            1575

Gly Glu Pro Val Thr Val Tyr Arg Leu Glu Glu Ser Ser Pro Asn
    1580            1585            1590

Ile Leu Asn Asn Ser Met Ser Ser Trp Ser Gln Leu Gly Leu Cys
    1595            1600            1605

Ala Lys Ile Glu Phe Leu Ser Lys Glu Glu Met Gly Gly Gly Leu
    1610            1615            1620

Arg Arg Ala Val Lys Val Gln Cys Thr Trp Ser Glu His Asp Ile
    1625            1630            1635

Leu Lys Ser Gly His Leu Tyr Ile Ile Lys Ser Phe Leu Pro Glu
    1640            1645            1650

Val Val Asn Thr Trp Ser Ser Ile Tyr Lys Glu Asp Thr Val Leu
    1655            1660            1665

His Leu Cys Leu Arg Glu Ile Gln Gln Gln Arg Ala Ala Gln Lys
    1670            1675            1680

Leu Thr Phe Ala Phe Asn Gln Met Lys Pro Lys Ser Ile Pro Tyr
    1685            1690            1695

Ser Pro Arg Phe Leu Glu Val Phe Leu Leu Tyr Cys His Ser Ala
    1700            1705            1710

Gly Gln Trp Phe Ala Val Glu Glu Cys Met Thr Gly Glu Phe Arg
    1715            1720            1725

Lys Tyr Asn Asn Asn Asn Gly Asp Glu Ile Ile Pro Thr Asn Thr
```

-continued

| | | 1730 | | | | 1735 | | | | 1740 | | |
|---|---|---|---|---|---|---|---|---|---|---|---|---|

Leu Glu Glu Ile Met Leu Ala Phe Ser His Trp Thr Tyr Glu Tyr
    1745                          1750                        1755

Thr Arg Gly Glu Leu Leu Val Leu Asp Leu Gln Gly Val Gly Glu
    1760                          1765                        1770

Asn Leu Thr Asp Pro Ser Val Ile Lys Ala Glu Glu Lys Arg Ser
    1775                          1780                        1785

Cys Asp Met Val Phe Gly Pro Ala Asn Leu Gly Glu Asp Ala Ile
    1790                          1795                        1800

Lys Asn Phe Arg Ala Lys His His Cys Asn Ser Cys Cys Arg Lys
    1805                          1810                        1815

Leu Lys Leu Pro Asp Leu Lys Arg Asn Asp Tyr Thr Pro Asp Lys
    1820                          1825                        1830

Ile Ile Phe Pro Gln Asp Glu Pro Ser Asp Leu Asn Leu Gln Pro
    1835                          1840                        1845

Gly Asn Ser Thr Lys Glu Ser Glu Ser Thr Asn Ser Val Arg Leu
    1850                          1855                        1860

Met Leu
    1865

<210> SEQ ID NO 29
<211> LENGTH: 4061
<212> TYPE: DNA
<213> ORGANISM: Homo sapiens

<400> SEQUENCE: 29

```
ggtctggaag cagagccggc ggagggagcg ccggggccct gggctgcagg aggttgcggc        60
ggccgcggca gcatggtggt gccggagaag gagcagagct ggatccccaa gatcttcaag       120
aagaagacct gcacgacgtt catagttgac tccacagatc cggagggac cttgtgccag        180
tgtgggcgcc cccggaccgc ccaccccgca gtggccatgg aggatgcctt cggggcagcc       240
gtggtgaccg tgtgggacag cgatgcacac accacggaga agcccaccga tgcctacgga       300
gagctggact tcacggggc cggccgcaag cacagcaatt cctccggct ctctgaccga        360
acggatccag ctgcagttta tagtctggtc acacgcacat ggggcttccg tgccccgaac       420
ctggtggtgt cagtgctggg gggatcgggg ggccccgtcc tccagacctg gctgcaggac       480
ctgctgcgtc gtgggctggt gcgggctgcc cagagcacag agcctggat tgtcactggg       540
ggtctgcaca cggcatcgg ccggcatgtt ggtgtggctg tacgggacca tcagatggcc       600
agcactgggg gcaccaaggt ggtggccatg gtgtgtgccc cctgggtgt ggtccggaat       660
agagacaccc tcatcaaccc caagggctcg ttccctgcga gtaccggtg gcgcggtgac       720
ccggaggacg gggtccagtt tcccctggac tacaactact cggccttctt cctggtggac       780
gacggcacac acggctgcct gggggggcgag aaccgcttcc gcttgcgcct ggagtcctac       840
atctcacagc agaagacggg cgtgggaggg actggaattg acatccctgt cctgctcctc       900
ctgattgatg tgatgagaa gatgttgacg cgaatagaga cgccacccca ggctcagctc       960
ccatgtctcc tcgtggctgg ctcaggggga gctgcggact gcctggcgga gaccctggaa      1020
gacactctgg ccccagggag tggggagcc aggcaaggcg aagcccgaga tcgaatcagg      1080
cgtttctttc ccaaggggga ccttgaggtc ctgcaggccc agtggagag gattatgacc      1140
cggaaggagc tcctgacagt ctattcttct gaggatgggt ctgaggaatt cgagaccata      1200
gttttgaagg cccttgtgaa ggcctgtggg agctcggagg cctcagccta cctggatgag      1260
```

```
ctgcgtttgg ctgtggcttg gaaccgcgtg gacattgccc agagtgaact ctttcggggg    1320
gacatccaat ggcggtcctt ccatctcgaa gcttccctca tggacgccct gctgaatgac    1380
cggcctgagt tcgtgcgctt gctcatttcc cacggcctca gcctgggcca cttcctgacc    1440
ccgatgcgcc tggcccaact ctacagcgcg gcgccctcca actcgctcat ccgcaacctt    1500
ttggaccagg cgtcccacag cgcaggcacc aaagccccag ccctaaaagg gggagctgcg    1560
gagctccggc ccctgacgt ggggcatgtg ctgaggatgc tgctggggaa gatgtgcgcg    1620
ccgaggtacc cctccggggg cgcctgggac cctcacccag ccagggcttc ggggagagc     1680 atgtatctgc tctcggacaa ggccaccctcg ccgctctcgc tggatgctgg cctcgggcag   1740 gcccctggα gcgacctgct tctttgggca ctgttgctga caggggcaca gatggccatg    1800
tacttctggg agatgggttc caatgcagtt tcctcagctc ttggggcctg tttgctgctc    1860
cgggtgatgg cacgcctgga gcctgacgct gaggaggcag cacggaggaa agacctggcg    1920
ttcaagtttg aggggatggg cgttgacctc tttggcgagt gctatcgcag cagtgaggtg    1980
agggctgccc gcctcctcct ccgtcgctgc ccgctctggg gggatgccac ttgcctccag    2040
ctggccatgc aagctgacgc ccgtgccttc tttgcccagg atggggtaca gtctctgctg    2100
acacagaagt ggtggggaga tatggccagc actacaccca tctgggccct ggttctcgcc    2160
ttcttttgcc ctccactcat ctacacccgc ctcatcacct tcaggaaatc agaagaggag    2220
cccacacggg aggagctaga gtttgacatg gatagtgtca ttaatgggga agggcctgtc    2280
gggacggcgg acccagccga gaagacgccg ctgggggtcc cgcgccagtc gggccgtccg    2340
ggttgctgcg ggggccgctg cggggggcgc cggtgcctac gccgctggtt ccacttctgg    2400
ggcgcgccgg tgaccatctt catgggcaac gtggtcagct acctgctgtt cctgctgctt    2460
ttctcgcggg tgctgctcgt ggatttccag ccggcgccgc ccggctccct ggagctgctg    2520
ctctatttct gggctttcac gctgctgtgc gaggaactgc gccagggcct gagcggaggc    2580
gggggcagcc tcgccagcgg gggcccgggg cctggccatg cctcactgag ccagcgcctg    2640
cgcctctacc tcgccgacag ctggaaccag tgcgacctag tggctctcac ctgcttcctc    2700
ctgggcgtgg gctgccggct gaccccgggt ttgtaccacc tgggccgcac tgtcctctgc    2760
atcgacttca tggttttcac ggtgcggctg cttcacatct tcacggtcaa caaacagctg    2820
gggcccaaga tcgtcatcgt gagcaagatg atgaaggacg tgttcttctt cctcttcttc    2880
ctcggcgtgt ggctggtagc ctatggcgtg gccacggagg ggctcctgag gccacgggac    2940
agtgacttcc caagtatcct gcgccgcgtc ttctaccgtc cctacctgca gatcttcggg    3000
cagattcccc aggaggacat ggacgtggcc ctcatggagc acagcaactg ctcgtcggag    3060
cccggcttct gggcacaccc tcctggggcc caggcgggca cctgcgtctc ccagtatgcc    3120
aactggctgg tggtgctgct cctcgtcatc ttcctgctcg tggccaacat cctgctggtc    3180
aacttgctca ttgccatgtt cagttacaca ttcgcaaag tacagggcaa cagcgatctc    3240
tactggaagg cgcagcgtta ccgcctcatc cgggaattcc actctcggcc cgcgctggcc    3300 ccgccctta tcgtcatctc ccacttgcgc ctcctgctca gcaattgtg caggcgaccc    3360 cggagccccc agccgtcctc cccggccctc gagcatttcc gggtttacct ttctaaggaa    3420
gccgagcgga agctgctaac gtgggaatcg gtgcataagg agaactttct gctgcacgc    3480 gctagggaca gcggggagag cgactccgag cgtctgaagc gcacgtccca gaaggtggac    3540
ttggcactga aacagctggg acacatccgc gagtacgaac agcgcctgaa agtgctggag    3600
cgggaggtcc agcagtgtag ccgcgtcctg gggtgggtgg ccgaggccct gagccgctct    3660
```

-continued

```
gccttgctgc cccaggtgg gccgccaccc cctgacctgc ctgggtccaa agactgagcc      3720
ctgctggcgg acttcaagga gaagccccca caggggattt tgctcctaga gtaaggctca      3780
tctgggcctc ggcccccgca cctggtggcc ttgtccttga ggtgagcccc atgtccatct      3840
gggccactgt caggaccacc tttgggagtg tcatccttac aaaccacagc atgcccggct      3900
cctcccagaa ccagtcccag cctgggagga tcaaggcctg gatcccgggc cgttatccat      3960
ctggaggctg cagggtcctt ggggtaacag ggaccacaga cccctcacca ctcacagatt      4020
cctcacactg gggaaataaa gccatttcag aggaaaaaaa a                         4061

<210> SEQ ID NO 30
<211> LENGTH: 1214
<212> TYPE: PRT
<213> ORGANISM: Homo sapiens

<400> SEQUENCE: 30

Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Val Val Thr Val Trp Asp Ser Asp
    50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Ser Gly Gly Pro
        115                 120                 125

Val Leu Gln Thr Trp Leu Gln Asp Leu Leu Arg Arg Gly Leu Val Arg
130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
    210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
            260                 265                 270

Val Leu Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
    290                 295                 300
```

-continued

```
Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
            325                 330                 335

Arg Phe Phe Pro Lys Gly Asp Leu Glu Val Leu Gln Ala Gln Val Glu
                340                 345                 350

Arg Ile Met Thr Arg Lys Glu Leu Leu Thr Val Tyr Ser Ser Glu Asp
            355                 360                 365

Gly Ser Glu Glu Phe Glu Thr Ile Val Leu Lys Ala Leu Val Lys Ala
        370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                405                 410                 415

Asp Ile Gln Trp Arg Ser Phe His Leu Glu Ala Ser Leu Met Asp Ala
            420                 425                 430

Leu Leu Asn Asp Arg Pro Glu Phe Val Arg Leu Leu Ile Ser His Gly
        435                 440                 445

Leu Ser Leu Gly His Phe Leu Thr Pro Met Arg Leu Ala Gln Leu Tyr
    450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
                485                 490                 495

Glu Leu Arg Pro Pro Asp Val Gly His Val Leu Arg Met Leu Leu Gly
            500                 505                 510

Lys Met Cys Ala Pro Arg Tyr Pro Ser Gly Gly Ala Trp Asp Pro His
        515                 520                 525

Pro Gly Gln Gly Phe Gly Glu Ser Met Tyr Leu Leu Ser Asp Lys Ala
    530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Asn Arg Ala Gln Met Ala Met
                565                 570                 575

Tyr Phe Trp Glu Met Gly Ser Asn Ala Val Ser Ala Leu Gly Ala
            580                 585                 590

Cys Leu Leu Leu Arg Val Met Ala Arg Leu Glu Pro Asp Ala Glu Glu
        595                 600                 605

Ala Ala Arg Arg Lys Asp Leu Ala Phe Lys Phe Glu Gly Met Gly Val
610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
                645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
        675                 680                 685

Pro Ile Trp Ala Leu Val Leu Ala Phe Phe Cys Pro Pro Leu Ile Tyr
    690                 695                 700

Thr Arg Leu Ile Thr Phe Arg Lys Ser Glu Glu Glu Pro Thr Arg Glu
705                 710                 715                 720
```

-continued

```
Glu Leu Glu Phe Asp Met Asp Ser Val Ile Asn Gly Glu Gly Pro Val
            725                 730                 735
Gly Thr Ala Asp Pro Ala Glu Lys Thr Pro Leu Gly Val Pro Arg Gln
            740                 745                 750
Ser Gly Arg Pro Gly Cys Cys Gly Gly Arg Cys Gly Arg Arg Cys
            755                 760                 765
Leu Arg Arg Trp Phe His Phe Trp Gly Ala Pro Val Thr Ile Phe Met
770                 775                 780
Gly Asn Val Val Ser Tyr Leu Leu Phe Leu Leu Leu Phe Ser Arg Val
785                 790                 795                 800
Leu Leu Val Asp Phe Gln Pro Ala Pro Pro Gly Ser Leu Glu Leu Leu
            805                 810                 815
Leu Tyr Phe Trp Ala Phe Thr Leu Leu Cys Glu Glu Leu Arg Gln Gly
            820                 825                 830
Leu Ser Gly Gly Gly Gly Ser Leu Ala Ser Gly Gly Pro Gly Pro Gly
            835                 840                 845
His Ala Ser Leu Ser Gln Arg Leu Arg Leu Tyr Leu Ala Asp Ser Trp
850                 855                 860
Asn Gln Cys Asp Leu Val Ala Leu Thr Cys Phe Leu Leu Gly Val Gly
865                 870                 875                 880
Cys Arg Leu Thr Pro Gly Leu Tyr His Leu Gly Arg Thr Val Leu Cys
            885                 890                 895
Ile Asp Phe Met Val Phe Thr Val Arg Leu Leu His Ile Phe Thr Val
            900                 905                 910
Asn Lys Gln Leu Gly Pro Lys Ile Val Ile Val Ser Lys Met Met Lys
            915                 920                 925
Asp Val Phe Phe Phe Leu Phe Phe Leu Gly Val Trp Leu Val Ala Tyr
930                 935                 940
Gly Val Ala Thr Glu Gly Leu Leu Arg Pro Arg Asp Ser Asp Phe Pro
945                 950                 955                 960
Ser Ile Leu Arg Arg Val Phe Tyr Arg Pro Tyr Leu Gln Ile Phe Gly
            965                 970                 975
Gln Ile Pro Gln Glu Asp Met Asp Val Ala Leu Met Glu His Ser Asn
            980                 985                 990
Cys Ser Ser Glu Pro Gly Phe Trp Ala His Pro Pro Gly Ala Gln Ala
            995                 1000                1005
Gly Thr Cys Val Ser Gln Tyr Ala Asn Trp Leu Val Val Leu Leu
    1010                1015                1020
Leu Val Ile Phe Leu Leu Val Ala Asn Ile Leu Leu Val Asn Leu
    1025                1030                1035
Leu Ile Ala Met Phe Ser Tyr Thr Phe Gly Lys Val Gln Gly Asn
    1040                1045                1050
Ser Asp Leu Tyr Trp Lys Ala Gln Arg Tyr Arg Leu Ile Arg Glu
    1055                1060                1065
Phe His Ser Arg Pro Ala Leu Ala Pro Pro Phe Ile Val Ile Ser
    1070                1075                1080
His Leu Arg Leu Leu Arg Gln Leu Cys Arg Arg Pro Arg Ser
    1085                1090                1095
Pro Gln Pro Ser Ser Pro Ala Leu Glu His Phe Arg Val Tyr Leu
    1100                1105                1110
Ser Lys Glu Ala Glu Arg Lys Leu Leu Thr Trp Glu Ser Val His
    1115                1120                1125
Lys Glu Asn Phe Leu Leu Ala Arg Ala Arg Asp Lys Arg Glu Ser
```

```
                    1130                1135                1140
Asp Ser Glu Arg Leu Lys Arg Thr Ser Gln Lys Val Asp Leu Ala
    1145                1150                1155

Leu Lys Gln Leu Gly His Ile Arg Glu Tyr Glu Gln Arg Leu Lys
    1160                1165                1170

Val Leu Glu Arg Glu Val Gln Gln Cys Ser Arg Val Leu Gly Trp
    1175                1180                1185

Val Ala Glu Ala Leu Ser Arg Ser Ala Leu Leu Pro Pro Gly Gly
    1190                1195                1200

Pro Pro Pro Pro Asp Leu Pro Gly Ser Lys Asp
    1205                1210

<210> SEQ ID NO 31
<211> LENGTH: 4646
<212> TYPE: DNA
<213> ORGANISM: Homo sapiens

<400> SEQUENCE: 31
tcgacccacg cgtccgccca cgcgtccgcc cacgcgtccg cccacgcgtc cgcccacgcg      60
tccgcccacg cgtccggggt gaaagmramy cmygcktsms aaaaaccgtc acttaggaaa     120
agatgtcctt tcgggcagcc aggctcagca tgaggaacag aaggaatgac actctggaca     180
gcacccggac cctgtactcc agcgcgtctc ggagcacaga cttgtcttac agtgaaagcg     240
acttggtgaa ttttattcaa gcaaatttta agaaacgaga atgtgtcttc tttaccaaag     300
attccaaggc cacggagaat gtgtgcaagt gtggctatgc ccagagccag cacatggaag     360
gcacccagat caaccaaagt gagaaatgga actacaagaa acacaccaag gaatttccta     420
ccgacgcctt tggggatatt cagtttgaga cactggggaa gaaggggaag tatatacgtc     480
tgtcctgcga cacggacgcg gaaatccttt acgagctgct gacccagcac tggcacctga     540
aaacacccaa cctggtcatt tctgtgaccg gggcgccaa gaacttcgcc ctgaagccgc     600
gcatgcgcaa gatcttcagc cggctcatct acatcgcgca gtccaaaggt gcttggattc     660
tcacgggagg cacccattat ggcctgatga agtacatcgg ggaggtggtg agagataaca     720
ccatcagcag gagttcagag gagaatattg tggccattgg catagcagct ggggcatgg      780
tctccaaccg ggacaccctc atcaggaatt gcgatgctga gggctatttt ttagcccagt     840
accttatgga tgacttcaca agagatccac tgtgtatcct ggacaacaac cacacacatt     900
tgctgctcgt ggacaatggc tgtcatggac atcccactgt cgaagcaaag ctccggaatc     960
agctagagaa gtatatctct gagcgcacta ttcaagattc caactatggt ggcaagatcc    1020
ccattgtgtg ttttgcccaa ggaggtggaa aagagacttt gaaagccatc aatacctcca    1080
tcaaaaataa aattccttgt gtggtggtgg aaggctcggg ccagatcgct gatgtgatcg    1140
ctagcctggt ggaggtggag gatgccctga catcttctgc cgtcaaggag aagctggtgc    1200
gcttttacc ccgcacggtg tcccggctgc ctgaggagga gactgagagt tggatcaaat    1260
ggctcaaaga aattctcgaa tgttctcacc tattaacagt tattaaaatg gaagaagctg    1320
gggatgaaat tgtgagcaat gccatctcct acgctctata caaagccttc agcaccagtg    1380
agcaagacaa ggataactgg aatgggcagc tgaagcttct gctggagtgg aaccagctgg    1440
acttagccaa tgatgagatt ttcaccaatg accgccgatg ggagtctgct gaccttcaag    1500
aagtcatgtt tacggctctc ataaaggaca gacccaagtt tgtccgcctc ttctgggaga    1560
atggcttgaa cctacggaag tttctcaccc atgatgtcct cactgaactc ttctccaacc    1620
```

-continued

```
acttcagcac gcttgtgtac cggaatctgc agatcgccaa gaattcctat aatgatgccc    1680
tcctcacgtt tgtctggaaa ctggttgcga acttccgaag aggcttccgg aaggaagaca    1740
gaaatggccg ggacgagatg gacatagaac tccacgacgt gtctcctatt actcggcacc    1800
ccctgcaagc tctcttcatc tgggccattc ttcagaataa gaaggaactc tccaaagtca    1860
tttgggagca gaccagggc tgcactctgg cagccctggg agccagcaag cttctgaaga    1920
ctctggccaa agtgaagaac gacatcaatg ctgctgggga gtccgaggag ctggctaatg    1980
agtacgagac ccgggctgtt gagctgttca ctgagtgtta cagcagcgat gaagacttgg    2040
cagaacagct gctggtctat tcctgtgaag ctttggggtgg aagcaactgt ctggagctgg    2100
cggtggaggc cacagaccag catttcatcg cccagcctgg ggtccagaat tttctttcta    2160
agcaatggta tggagagatt tcccgagaca ccaagaactg gaagattatc ctgtgtctgt    2220
ttattatacc cttggtgggc tgtggcttttg tatcatttag gaagaaacct gtcgacaagc    2280
acaagaagct gctttggtac tatgtggcgt tcttcacctc ccccttcgtg gtcttctcct    2340
ggaatgtggt cttctacatc gccttcctcc tgctgtttgc ctacgtgctg ctcatggatt    2400
tccattcggt gccacacccc cccgagctgg tcctgtactc gctggtcttt gtcctcttct    2460
gtgatgaagt gagacagtgg tacgtaaatg gggtgaatta ttttactgac ctgtggaatg    2520
tgatggacac gctgggcctt ttttacttca tagcaggaat tgtatttcgg ctccactctt    2580
ctaataaaag ctctttgtat tctggacgag tcattttctg tctggactac attattttca    2640
ctctaagatt gatccacatt tttactgtaa gcagaaactt aggacccaag attataatgc    2700
tgcagaggat gctgatcgat gtgttcttct tcctgttcct cttttgcggtg tggatggtgg    2760
cctttggcgt ggccaggcaa gggatcctta ggcagaatga gcagcgctgg aggtggatat    2820
tccgttcggt catctacgag ccctacctgg ccatgttcgg ccaggtgccc agtgacgtgg    2880
atggtaccac gtatgacttt gcccactgca ccttcactgg gaatgagtcc aagccactgt    2940
gtgtggagct ggatgagcac aacctgcccc ggttccccga gtggatcacc atcccctgg    3000
tgtgcatcta catgttatcc accaacatcc tgctggtcaa cctgctggtc gccatgtttg    3060
gctacacggt gggcaccgtc caggagaaca atgaccaggt ctggaagttc cagaggtact    3120
tcctggtgca ggagtactgc agccgcctca atatccccctt cccccttcatc gtcttcgctt    3180
acttctacat ggtggtgaag aagtgcttca gtgttgctg caaggagaaa acatggagt    3240
cttctgtctg ctgtttcaaa aatgaagaca atgagactct ggcatgggag ggtgtcatga    3300
aggaaaacta ccttgtcaag atcaacacaa aagccaacga cacctcagag gaaatgaggc    3360
atcgatttag acaactggat acaaagctta atgatctcaa gggtcttctg aaagagattg    3420
ctaataaaat caaataaaac tgtatgaact ctaatggaga aaaatctaat tatagcaaga    3480
tcatattaag gaatgctgat gaacaatttt gctatcgact actaaatgag agattttcag    3540
accccctgggt acatggtgga tgattttaaa tcacccctagt gtgctgagac cttgagaata    3600
aagtgtgtga ttggtttcat acttgaagac ggatataaag gaagaatatt tcctttatgt    3660
gtttctccag aatggtgcct gtttctctct gtgtctcaat gcctgggact ggaggttgat    3720
agtttaagtg tgttcttacc gcctcctttt tcctttaatc ttattttttga tgaacacata    3780
tataggagaa catctatcct atgaataaga acctggtcat gctttactcc tgtattgtta    3840
ttttgttcat ttccaattga ttctctactt ttccctttt tgtattatgt gactaattag    3900
ttggcatatt gtwaaaagtc tctcaaatta ggccagattc taaaacatgc tgcagcaaga    3960
ggaccccgct ctcttcagga aaagtgtttt catttctcag gatgcttctt acctgtcaga    4020
```

-continued

```
ggaggtgaca aggcagtctc ttgctctctt ggactcacca ggctcctatt gaaggaacca      4080
cccccattcc taaatatgtg aaaagtcgcc caaaatgcaa ccttgaaagg cactactgac      4140
tttgttctta ttggatactc ctcttattta ttattttttcc attaaaaata atagctggct     4200
attatagaaa atttagacca tacagagatg tagaaagaac ataaattgtc cccattacct      4260
taaggtaatc actgctaaca atttctggat ggttttttcaa gtctattttt tttctatgta    4320
tgtctcaatt ctctttcaaa attttacaga atgttatcat actacatata acttttttat     4380
gtaagctttt tcacttagta ttttatcaaa tatgttttta ttatattcat agccttctta     4440
aacattatat caataattgc ataataggca acctctagcg attaccataa ttttgctcat     4500
tgaaggctat ctccagttga tcattgggat gagcatcttt gtgcatgaat cctattgctg     4560
tatttgggaa aattttccaa ggttagattc caataaatat ctatttatta ttaaaaaaaa    4620
aaaaaaaagg gcggccgctc tagagt                                          4646
```

<210> SEQ ID NO 32
<211> LENGTH: 1104
<212> TYPE: PRT
<213> ORGANISM: Homo sapiens

<400> SEQUENCE: 32

```
Met Ser Phe Arg Ala Ala Arg Leu Ser Met Arg Asn Arg Arg Asn Asp
  1               5                  10                  15

Thr Leu Asp Ser Thr Arg Thr Leu Tyr Ser Ser Ala Ser Arg Ser Thr
             20                  25                  30

Asp Leu Ser Tyr Ser Glu Ser Asp Leu Val Asn Phe Ile Gln Ala Asn
         35                  40                  45

Phe Lys Lys Arg Glu Cys Val Phe Phe Thr Lys Asp Ser Lys Ala Thr
     50                  55                  60

Glu Asn Val Cys Lys Cys Gly Tyr Ala Gln Ser Gln His Met Glu Gly
 65                  70                  75                  80

Thr Gln Ile Asn Gln Ser Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Ser Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Ala Glu Gly Tyr Phe Leu Ala Gln Tyr
225                 230                 235                 240

Leu Met Asp Asp Phe Thr Arg Asp Pro Leu Cys Ile Leu Asp Asn Asn
                245                 250                 255
```

```
His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
            275                 280                 285

Thr Ile Gln Asp Ser Asn Tyr Gly Gly Lys Ile Pro Ile Val Cys Phe
            290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Glu Gly Ser Gly Gln Ile Ala
                325                 330                 335

Asp Val Ile Ala Ser Leu Val Glu Val Glu Asp Ala Leu Thr Ser Ser
            340                 345                 350

Ala Val Lys Glu Lys Leu Val Arg Phe Leu Pro Arg Thr Val Ser Arg
            355                 360                 365

Leu Pro Glu Glu Glu Thr Glu Ser Trp Ile Lys Trp Leu Lys Glu Ile
    370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Ser Glu Gln Asp Lys Asp Asn Trp Asn Gly Gln Leu Lys Leu
            420                 425                 430

Leu Leu Glu Trp Asn Gln Leu Asp Leu Ala Asn Asp Glu Ile Phe Thr
            435                 440                 445

Asn Asp Arg Arg Trp Glu Ser Ala Asp Leu Gln Glu Val Met Phe Thr
            450                 455                 460

Ala Leu Ile Lys Asp Arg Pro Lys Phe Val Arg Leu Phe Leu Glu Asn
465                 470                 475                 480

Gly Leu Asn Leu Arg Lys Phe Leu Thr His Asp Val Leu Thr Glu Leu
            485                 490                 495

Phe Ser Asn His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
            515                 520                 525

Ala Asn Phe Arg Arg Gly Phe Arg Lys Glu Asp Arg Asn Gly Arg Asp
            530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
            580                 585                 590

Gly Ala Ser Lys Leu Leu Lys Thr Leu Ala Lys Val Lys Asn Asp Ile
            595                 600                 605

Asn Ala Ala Gly Glu Ser Glu Glu Leu Ala Asn Glu Tyr Glu Thr Arg
            610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
```

-continued

```
                675                 680                 685
Asp Thr Lys Asn Trp Lys Ile Ile Leu Cys Leu Phe Ile Ile Pro Leu
690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
                740                 745                 750

Ala Tyr Val Leu Leu Met Asp Phe His Ser Val Pro His Pro Pro Glu
                755                 760                 765

Leu Val Leu Tyr Ser Leu Val Phe Val Leu Phe Cys Asp Glu Val Arg
770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
                820                 825                 830

Cys Leu Asp Tyr Ile Ile Phe Thr Leu Arg Leu Ile His Ile Phe Thr
                835                 840                 845

Val Ser Arg Asn Leu Gly Pro Lys Ile Ile Met Leu Gln Arg Met Leu
850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
                900                 905                 910

Gly Gln Val Pro Ser Asp Val Asp Gly Thr Thr Tyr Asp Phe Ala His
                915                 920                 925

Cys Thr Phe Thr Gly Asn Glu Ser Lys Pro Leu Cys Val Glu Leu Asp
930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
                980                 985                 990

Val Trp Lys Phe Gln Arg Tyr Phe Leu Val Gln Glu Tyr Cys Ser Arg
                995                 1000                1005

Leu Asn Ile Pro Phe Pro Phe Ile Val Phe Ala Tyr Phe Tyr Met
1010                1015                1020

Val Val Lys Lys Cys Phe Lys Cys Cys Cys Lys Glu Lys Asn Met
1025                1030                1035

Glu Ser Ser Val Cys Cys Phe Lys Asn Glu Asp Asn Glu Thr Leu
1040                1045                1050

Ala Trp Glu Gly Val Met Lys Glu Asn Tyr Leu Val Lys Ile Asn
1055                1060                1065

Thr Lys Ala Asn Asp Thr Ser Glu Glu Met Arg His Arg Phe Arg
1070                1075                1080

Gln Leu Asp Thr Lys Leu Asn Asp Leu Lys Gly Leu Leu Lys Glu
1085                1090                1095
```

```
Ile Ala  Asn Lys Ile Lys
    1100
```